(12) United States Patent
Eaves, III

(10) Patent No.: US 11,229,555 B2
(45) Date of Patent: Jan. 25, 2022

(54) REMOVABLE COVERING AND INTERACTIVE PACKAGING

(71) Applicant: EMRGE, LLC, Atlanta, GA (US)

(72) Inventor: Felmont F. Eaves, III, Atlanta, GA (US)

(73) Assignee: EMRGE, LLC, Atlanta, GA (US)

( * ) Notice: Subject to any disclaimer, the term of this patent is extended or adjusted under 35 U.S.C. 154(b) by 468 days.

(21) Appl. No.: 16/153,340

(22) Filed: Oct. 5, 2018

(65) Prior Publication Data
US 2019/0038474 A1 Feb. 7, 2019

Related U.S. Application Data

(63) Continuation of application No. 14/255,279, filed on Apr. 17, 2014, now Pat. No. 10,092,455, which is a
(Continued)

(51) Int. Cl.
*A61F 13/02* (2006.01)
*A61F 13/00* (2006.01)

(52) U.S. Cl.
CPC .... *A61F 13/0259* (2013.01); *A61F 13/00085* (2013.01); *Y10T 428/2486* (2015.01);
(Continued)

(58) Field of Classification Search
CPC ...... A61F 6/065; A61F 2006/041; A61F 6/06; A61F 6/20; A61F 6/08; A61F 6/14;
(Continued)

(56) References Cited

U.S. PATENT DOCUMENTS

| 815,264 A | 3/1906 | Chambers |
| 1,248,450 A | 12/1917 | Burke |

(Continued)

FOREIGN PATENT DOCUMENTS

| AU | 2012236205 B2 | 8/2016 |
| AU | 2016262734 | 12/2016 |

(Continued)

OTHER PUBLICATIONS

Office Action in counterpart Korean Application No. 10-2019-7026649 dated Sep. 26, 2019, pp. 1-5.
(Continued)

*Primary Examiner* — Ophelia A Hawthorne
(74) *Attorney, Agent, or Firm* — Additon, Pendleton & Witherspoon, P.A.

(57) ABSTRACT

A removable covering for an object includes an adhered section that is adhered to the object (e.g., adhered to a receiving surface of the object via an adhesive layer) and a free section that is not adhered to the object. The removable covering is sufficiently flexible to allow at least partial removal of the adhered section from the object by application of a force to the removable covering. Typically, the removable covering is adhered to the object such that resistance to removal of the covering from the object varies at different zones of attachment between the removable covering and the object. The resistance variation may be achieved, for example, by employing tabs, loops, folds, varying-strength adhesive strips, textures and/or release coatings. Exemplary packaging systems (e.g., containing removable coverings and/or objects) include features such that resistance to removal of the packaging system from an object varies at different phases of removal.

34 Claims, 38 Drawing Sheets

Related U.S. Application Data continuation of application No. PCT/US2012/061033, filed on Oct. 19, 2012.

(60) Provisional application No. 61/654,748, filed on Jun. 1, 2012, provisional application No. 61/561,522, filed on Nov. 18, 2011, provisional application No. 61/549,317, filed on Oct. 20, 2011.

(52) U.S. Cl.
CPC .................. Y10T 428/24355 (2015.01); Y10T 428/24612 (2015.01)

(58) Field of Classification Search
CPC .... A61F 6/00; A61F 6/04; A61F 5/451; A61F 5/453; A61M 25/0017; A41B 9/12; B29L 2031/4871
See application file for complete search history.

(56) References Cited

U.S. PATENT DOCUMENTS

| | | |
|---|---|---|
| 1,908,229 A | 5/1933 | Dyer |
| 2,254,620 A | 9/1941 | Miller |
| 2,341,121 A | 2/1944 | Schaaff |
| 2,371,978 A | 3/1945 | Perham |
| 2,421,193 A | 5/1947 | Gardner |
| 2,679,671 A | 6/1954 | Garber, Jr. |
| 2,912,735 A | 2/1957 | Johnson et al. |
| 3,014,483 A | 12/1961 | McCarthy |
| 3,068,870 A | 12/1962 | Levin |
| 3,082,773 A | 3/1963 | Renstrom et al. |
| 3,120,687 A | 2/1964 | Greening et al. |
| 3,487,836 A | 1/1970 | Niebel et al. |
| 3,625,220 A | 12/1971 | Engelsher |
| 3,695,271 A | 10/1972 | Chodorow |
| 3,831,608 A | 8/1974 | Kletschka et al. |
| 3,861,008 A | 1/1975 | Wannag |
| 3,901,239 A | 8/1975 | Tritsch |
| 4,011,639 A | 3/1977 | Koleske |
| 4,264,008 A * | 4/1981 | Kozlow ............. A61F 15/001 206/441 |
| 4,275,736 A | 6/1981 | Chodorow |
| D260,681 S | 9/1981 | Chodorow et al. |
| 4,506,669 A | 3/1985 | Blake, III |
| 4,539,990 A | 9/1985 | Stivala |
| 4,646,731 A | 3/1987 | Brower |
| 4,702,251 A | 10/1987 | Sheehan |
| D293,717 S | 1/1988 | Proulx et al. |
| 4,734,320 A | 3/1988 | Ohira et al. |
| 4,742,826 A | 5/1988 | McLorg |
| 4,815,468 A | 3/1989 | Annand |
| 4,825,866 A | 5/1989 | Pierce |
| 4,926,850 A | 5/1990 | Lott et al. |
| 5,074,293 A | 12/1991 | Lott et al. |
| 5,127,412 A | 7/1992 | Cosmetto et al. |
| 5,176,703 A | 1/1993 | Peterson |
| 5,230,701 A | 7/1993 | Meyer et al. |
| 5,366,480 A | 11/1994 | Corriveau et al. |
| D354,134 S | 1/1995 | Tanaka |
| 5,397,297 A | 3/1995 | Hunter |
| D359,144 S | 6/1995 | Healzer et al. |
| 5,489,083 A | 2/1996 | Rollor |
| 5,549,713 A | 8/1996 | Kim |
| 5,562,705 A | 10/1996 | Whiteford |
| 5,578,026 A | 11/1996 | Lavash et al. |
| 5,630,430 A | 5/1997 | Shultz et al. |
| 5,733,251 A | 3/1998 | Johns |
| 5,775,345 A | 7/1998 | Chou |
| D407,489 S | 3/1999 | Kalat |
| 5,947,917 A | 9/1999 | Carte et al. |
| 5,947,998 A | 9/1999 | Cartmell et al. |
| 6,117,111 A * | 9/2000 | Fleischmann ........ A61F 13/023 602/52 |
| 6,159,497 A * | 12/2000 | LaPrade ............... A61F 15/005 424/447 |
| 6,176,868 B1 | 1/2001 | Detour |
| 6,196,228 B1 | 3/2001 | Kreitzer et al. |
| 6,559,350 B1 | 5/2003 | Tetreault et al. |
| 6,573,421 B1 | 6/2003 | Lemaire |
| 6,894,204 B2 | 5/2005 | Dunshee |
| D530,420 S | 10/2006 | Chesnin |
| 7,332,641 B2 | 2/2008 | Lebner et al. |
| 7,683,234 B2 | 3/2010 | Gurtner et al. |
| 7,879,015 B2 | 2/2011 | Villefrance et al. |
| 8,157,839 B2 | 4/2012 | Riskin et al. |
| 8,183,428 B2 | 5/2012 | Gurtner et al. |
| 8,246,590 B2 | 8/2012 | Hu et al. |
| D667,167 S | 9/2012 | Stewart |
| D671,265 S | 11/2012 | Stewart |
| 8,323,313 B1 | 12/2012 | Belson et al. |
| D674,544 S | 1/2013 | Stewart |
| 8,395,011 B2 | 3/2013 | Zepeda et al. |
| 8,435,221 B2 | 5/2013 | Hu et al. |
| D683,860 S | 6/2013 | Quimby |
| D690,020 S | 9/2013 | Quimby |
| 8,562,576 B2 | 10/2013 | Hu et al. |
| 8,592,640 B2 | 11/2013 | Zepeda et al. |
| 8,674,164 B2 | 3/2014 | Zepeda et al. |
| 8,834,434 B2 | 9/2014 | Hu et al. |
| 8,915,942 B2 | 12/2014 | Zhang |
| 9,028,529 B2 | 5/2015 | Riskin et al. |
| 9,050,086 B2 | 6/2015 | Belson et al. |
| 9,089,328 B2 | 7/2015 | Belson et al. |
| 9,119,620 B2 | 9/2015 | Peterson et al. |
| 9,301,760 B2 | 4/2016 | Fox |
| 9,421,133 B2 | 8/2016 | Hu et al. |
| 9,492,171 B2 | 11/2016 | Petenaude |
| 9,517,163 B2 | 12/2016 | Goldman et al. |
| D780,317 S | 2/2017 | Vandervoort |
| 9,603,596 B2 | 3/2017 | Riskin et al. |
| 9,629,744 B2 | 4/2017 | Villefrance et al. |
| 9,649,226 B2 | 5/2017 | Zepeda et al. |
| D790,072 S | 6/2017 | Hiebert |
| D811,609 S | 2/2018 | Huff |
| 9,974,532 B2 | 5/2018 | Baas et al. |
| 10,064,616 B2 | 9/2018 | Lear et al. |
| D831,220 S | 10/2018 | Chase et al. |
| 10,092,455 B2 * | 10/2018 | Eaves, III ........... A61F 13/0259 |
| 10,213,350 B2 | 2/2019 | Jackson et al. |
| 10,327,774 B2 | 6/2019 | Eaves |
| D862,695 S | 10/2019 | Eaves, III et al. |
| 10,426,479 B2 | 10/2019 | Vold et al. |
| 10,517,768 B2 | 12/2019 | Zepeda et al. |
| D876,641 S | 2/2020 | Eaves, III et al. |
| 2002/0111641 A1 | 8/2002 | Peterson et al. |
| 2003/0120229 A1 | 6/2003 | de Jong et al. |
| 2003/0221700 A1 | 12/2003 | La Fauci |
| 2005/0080453 A1 | 4/2005 | Lebner |
| 2005/0177032 A1 | 8/2005 | Grossinger et al. |
| 2005/0193527 A1 | 9/2005 | Gould |
| 2006/0200198 A1 | 9/2006 | Riskin et al. |
| 2009/0125052 A1 | 5/2009 | Pinna et al. |
| 2009/0151128 A1 | 6/2009 | Gould |
| 2009/0240186 A1 | 9/2009 | Frang |
| 2009/0259203 A1 | 10/2009 | Hu et al. |
| 2010/0051046 A1 | 3/2010 | Stevenson et al. |
| 2010/0081983 A1 | 4/2010 | Zocher |
| 2010/0228287 A1 | 9/2010 | Jeekel |
| 2010/0236566 A1 | 9/2010 | Stachowski |
| 2010/0262126 A1 | 10/2010 | Hu et al. |
| 2011/0004173 A1 | 1/2011 | Hu et al. |
| 2011/0023906 A1 | 2/2011 | Tu |
| 2011/0040325 A1 | 2/2011 | Moehrle |
| 2011/0054547 A1 | 3/2011 | Anderson |
| 2011/0105963 A1 | 5/2011 | Hu et al. |
| 2011/0152738 A1 | 6/2011 | Zepeda et al. |
| 2012/0172779 A1 | 7/2012 | Spinelli et al. |
| 2012/0221044 A1 | 8/2012 | Archibald et al. |
| 2013/0150899 A1 | 6/2013 | Sixto, Jr. et al. |
| 2013/0178897 A1 | 7/2013 | Wu et al. |
| 2013/0282049 A1 | 10/2013 | Peterson et al. |
| 2014/0066943 A1 | 3/2014 | Sixto, Jr. et al. |

(56) References Cited

U.S. PATENT DOCUMENTS

| | | |
|---|---|---|
| 2014/0107597 A1 | 4/2014 | Hu et al. |
| 2014/0128819 A1 | 5/2014 | Eaves |
| 2014/0227483 A1 | 8/2014 | Eaves |
| 2014/0243901 A1 | 8/2014 | Mebarak et al. |
| 2014/0336701 A1 | 11/2014 | McLorg |
| 2015/0005722 A1 | 1/2015 | Hu et al. |
| 2015/0012037 A1 | 1/2015 | Goldman et al. |
| 2015/0112311 A1 | 4/2015 | Hammond et al. |
| 2015/0305739 A1 | 10/2015 | Rolandi et al. |
| 2016/0324693 A1 | 11/2016 | Hu et al. |
| 2017/0049630 A1 | 2/2017 | Goldman et al. |
| 2017/0071596 A1 | 3/2017 | Lear et al. |
| 2017/0333039 A1 | 11/2017 | Leung |
| 2018/0125492 A1 | 5/2018 | Eaves |
| 2018/0303483 A1 | 10/2018 | Zhang |
| 2018/0338757 A1 | 11/2018 | Lear et al. |
| 2018/0353335 A1 | 12/2018 | Walker |
| 2019/0038474 A1 | 2/2019 | Eaves |
| 2019/0133582 A1 | 5/2019 | Eaves et al. |
| 2019/0261989 A1 | 8/2019 | Eaves |

FOREIGN PATENT DOCUMENTS

| | | | |
|---|---|---|---|
| CA | 2830918 A1 | | 10/2012 |
| CN | 1889903 A | | 1/2007 |
| CN | 101606856 | | 12/2009 |
| CN | 101828939 B | | 9/2010 |
| CN | 201683935 U | | 12/2010 |
| CN | 201806846 U | | 4/2011 |
| CN | 103892877 A | | 7/2014 |
| CN | 105147344 A | | 12/2015 |
| CN | 205144638 U | | 4/2016 |
| CN | 103533900 A | | 12/2016 |
| EP | 0371808 | | 6/1990 |
| EP | 1496820 A1 | | 1/2005 |
| EP | 2691029 A2 | | 2/2014 |
| FR | 419096 | | 10/1910 |
| FR | 794710 | | 2/1936 |
| GB | 2311096 A | | 9/1997 |
| JP | H001-104122 | | 7/1969 |
| JP | 02-189147 A | | 7/1990 |
| JP | H002262515 A | | 10/1990 |
| JP | 2003-325575 | | 11/2003 |
| JP | 2011-500170 A | | 1/2011 |
| JP | 2014-516288 | | 7/2014 |
| KR | 10-2009-0066415 A | | 6/2009 |
| KR | 20110092900 A | | 8/2011 |
| KR | 2011009200 A | * | 10/2011 |
| KR | 10-2014-0020993 | | 2/2014 |
| TW | M340039 U | | 9/2008 |
| WO | 93/08777 A1 | | 5/1993 |
| WO | 96/28124 | | 9/1996 |
| WO | 00/10492 | | 3/2000 |
| WO | 02/26181 A1 | | 4/2002 |
| WO | 2006/124671 A2 | | 11/2006 |
| WO | 2009049232 A1 | | 4/2009 |
| WO | 2011/019859 A2 | | 2/2011 |
| WO | 2013188884 A1 | | 6/2012 |
| WO | 2012/135735 | | 10/2012 |
| WO | 2013/059600 | | 4/2013 |
| WO | 2013/059600 A1 | | 4/2013 |
| WO | 2018/075879 A1 | | 4/2014 |
| WO | 2016/0107897 A1 | | 7/2016 |
| WO | 2017/079782 A1 | | 5/2017 |
| WO | 2018/075879 | | 4/2018 |
| WO | 2021/072021 A1 | | 4/2021 |

OTHER PUBLICATIONS

Office Action in related Australian Application No. 2017208314 dated Sep. 11, 2018, pp. 1-5.
Office Action in counterpart Korean Application No. 10-2014-7011429 dated Dec. 13, 2018, pp. 1-6.
Office Action in counterpart Chinese Application No. 201610286609.9 dated Feb. 15, 2019, pp. 1-5.
International Search Report and Written Opinion issued in PCT/US12/61033 dated Mar. 29, 2013; 13 pages.
Australian Exam Report No. 1 in related AU Application No. 2012325922; dated May 18, 2016; 3 pages.
Australian Examination report No. 2 for standard patent application in counterpart AU Application 2012325922, dated Apr. 27, 2017, 4 pages.
European Search Report in Related EP Application No. 12841812.3, dated May 27, 15, 7 pages.
Canadian Office Action in Related CA Application No. 2850521, dated Aug. 6, 2018, 4 pages.
Japanese Office Action in related Application No. 2014-537290, dated Sep. 2, 2016, 12 pages.
First Chinese Office Action in related CN Application No. 201611102500.1, dated Aug. 20, 2018, 21 pages (including English Translation).
Summons to attend oral proceedings in related European Application No. 12762897.2 dated Mar. 22, 2021, pp. 1-11.
Partial Supplementary European Search Report in related European Application No. 17861546.4 dated Apr. 22, 2020, pp. 1-12.
Search Report in related European Application No. 17861546.4 dated Jul. 31, 2020, pp. 1-10.
Extended Search Report in related EP Application 12762897.2, dated May 27, 2015, 11 pages.
Japanese Office Action in related JP Application No. 2014-502866, dated Dec. 10, 2015, Translation provided, 11 pages.
Chinese First Office Action in related CN Application No. 201280017051.4, dated Jun. 1, 2015, Translation provided, 13 pages.
Chinese Second Office Action in related CN Application No. 201280017051.4, dated Dec. 31, 2015, Translation provided, 8 pages.
Australian Patent Examination Report No. 1 in related Australian Patent Application No. 201226205, dated Aug. 28, 2015, 5 pages.
International Search Report and Written Opinion issued in commonly owned PCT/US2012/031638 dated Nov. 29, 2012; 10 pages.
Supplementary Partial European Search Report in commonly owned EP Application No. 12762897, dated Dec. 23, 2014, 7 pages.
Japanese Notice of Reasons for Rejection in related JP Application No. 2014-502866, dated Oct. 3, 2016; 9 pages.
Southmedic Inc., SutureSafe Instructions for Use, 2 pages [Downloaded Jul. 25, 2017 from http://dynamictissuesystems.com/wp-content/uploads/2015/09/IFU0251_E.pdf].
SutureSafe Inc., Product Brochure SutureSafe Support closed wounds and provide stability; 2 pages [Downloaded Jul. 25, 2017 from http://dynamictissuesystems.com/wp-content/uploads/2015/09/SutureSafe-SS-lr2.pdf].
Search Report in related PCT Application No. PCT/2018/057569, dated Feb. 2, 2018, pp. 1-6.
Written Opinion in related PCT Application No. PCT/2018/057569, dated Apr. 26, 2018, pp. 1-5.
International Preliminary Report on Patentability in commonly owned International Application No. PCT/US2017/057569, dated May 2, 2019, pp. 1-6.
Amazon, "Elastic Bandage Wrap Compression Tape", Review by Maria A. Dec. 18, 2017, <URL:https://www.amazon.com/Elastic-Bandage-Wrap-Compression-Tape/dp/B06XQ8BY8?th=1> (Year 2017) 12 pages.
Supplementary Partial European Search Report in related EP Application No. 12762897, dated Dec. 23, 2014, 7 pages.
Examination Report No. 1 in related Australian Application No. 2016262734, dated Jan. 14, 2019, 3 pages.
International Search Report and Written Opinion in related International Application No. PCT/US20/54702 dated Mar. 11, 2021, pp. 1-28.
Ruckel, U.S. Pat. No. 765,793 issued Jul. 26, 1904, pp. 1-3.
Knott et al., "Curved bistable composite slit tubes with positive Gaussian curvature", University of Surrey, Guilford, United Kingdom, pp. 1-22.

(56) References Cited

OTHER PUBLICATIONS

Jiang et al., "Snapping of bistable, prestressed cylindrical shells", A Letters Journal Exploring, www.epljournal.org, Jun. 2018, EPL, 122 (2018) 64003, pp. 1-8.

Kebadze, et al., "Bistable prestressed shell structures", International Journal of Solids and Structures, www.elsevier.com/locate/ijsolstr, 41 (2004) pp. 2801-2820.

Kim et al., "Flytrap-inspired robot using structurally integrated actuation based on bistability and developable surface", Bioinspiration & Miomimetics, 9 (2014) 036004, pp. 1-15.

Seffen, "Morphing bistable orthotropic elliptical shallow shells", Proceedings of the Roayl Society, (2007) 463, 67-83, pp. 1-17.

\* cited by examiner

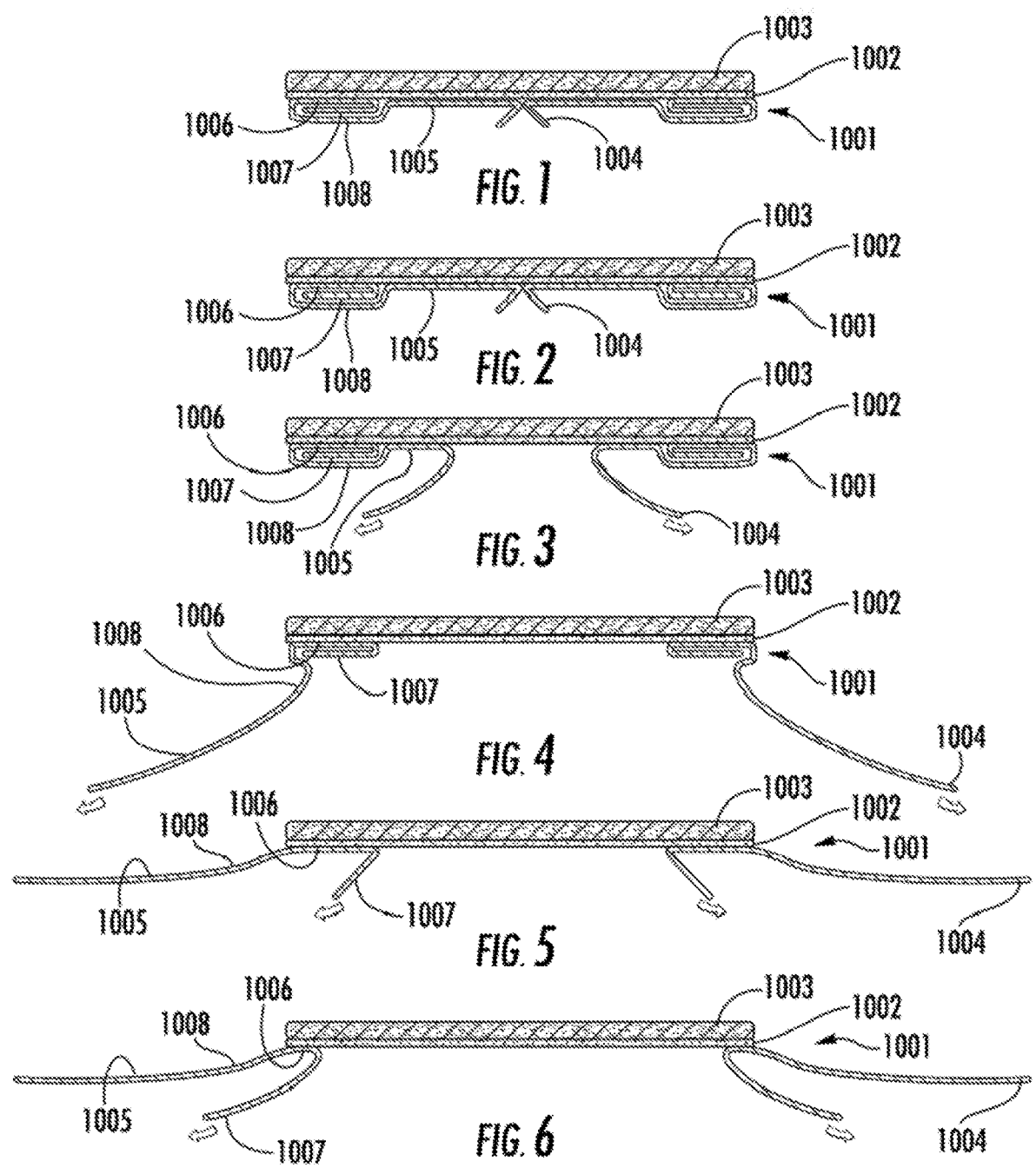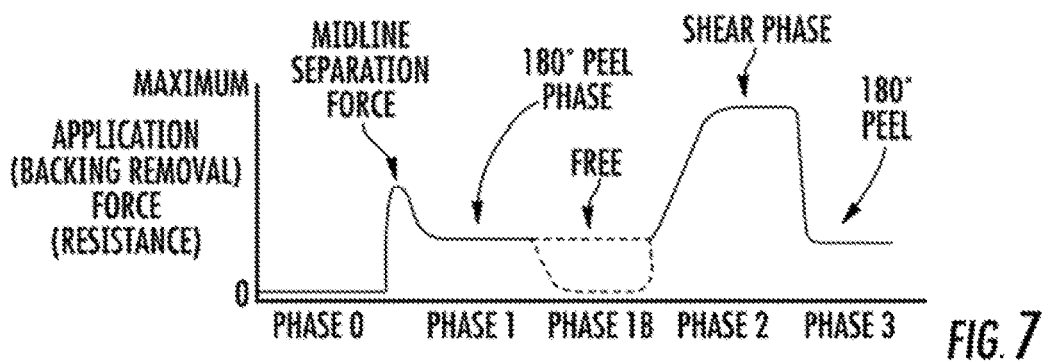

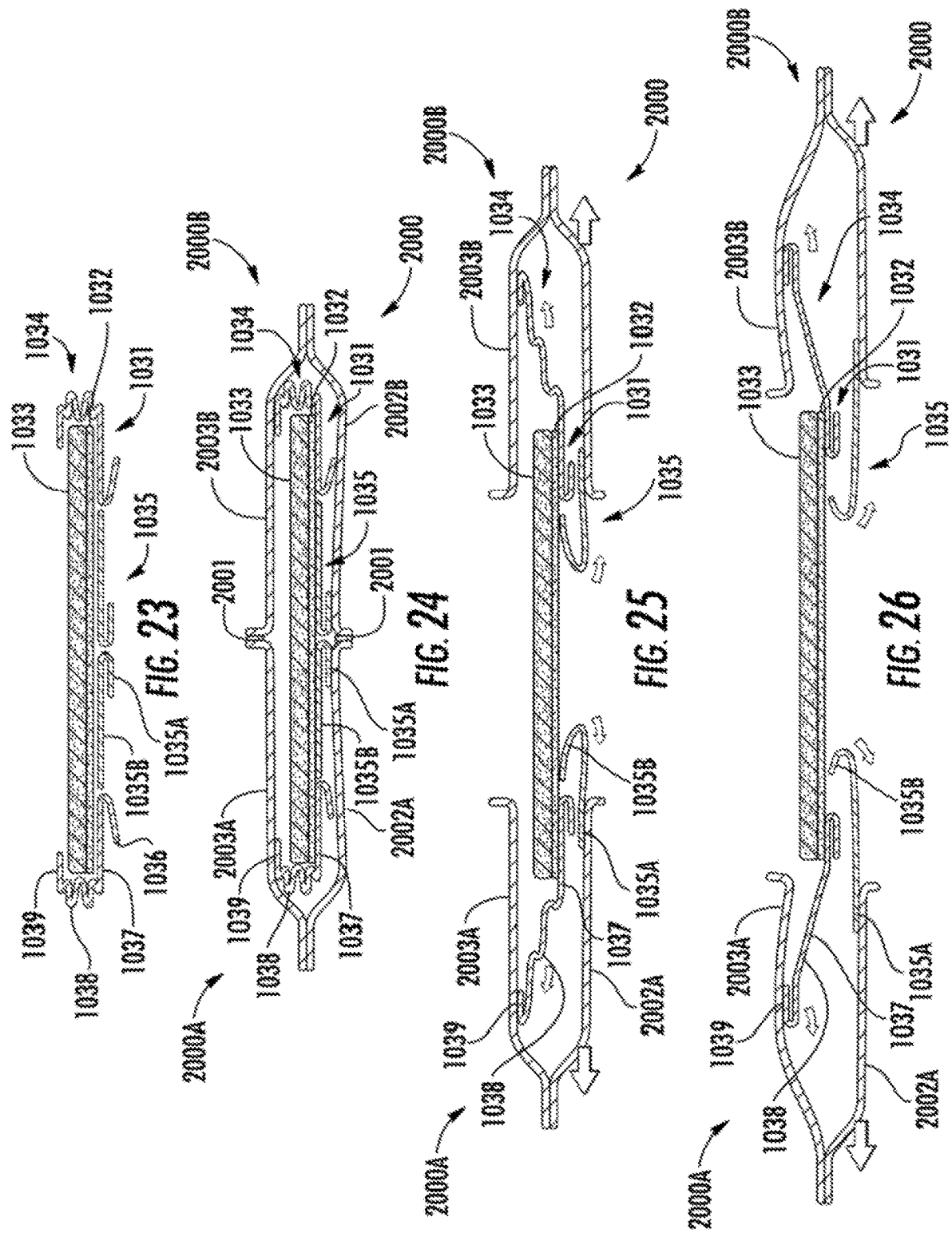

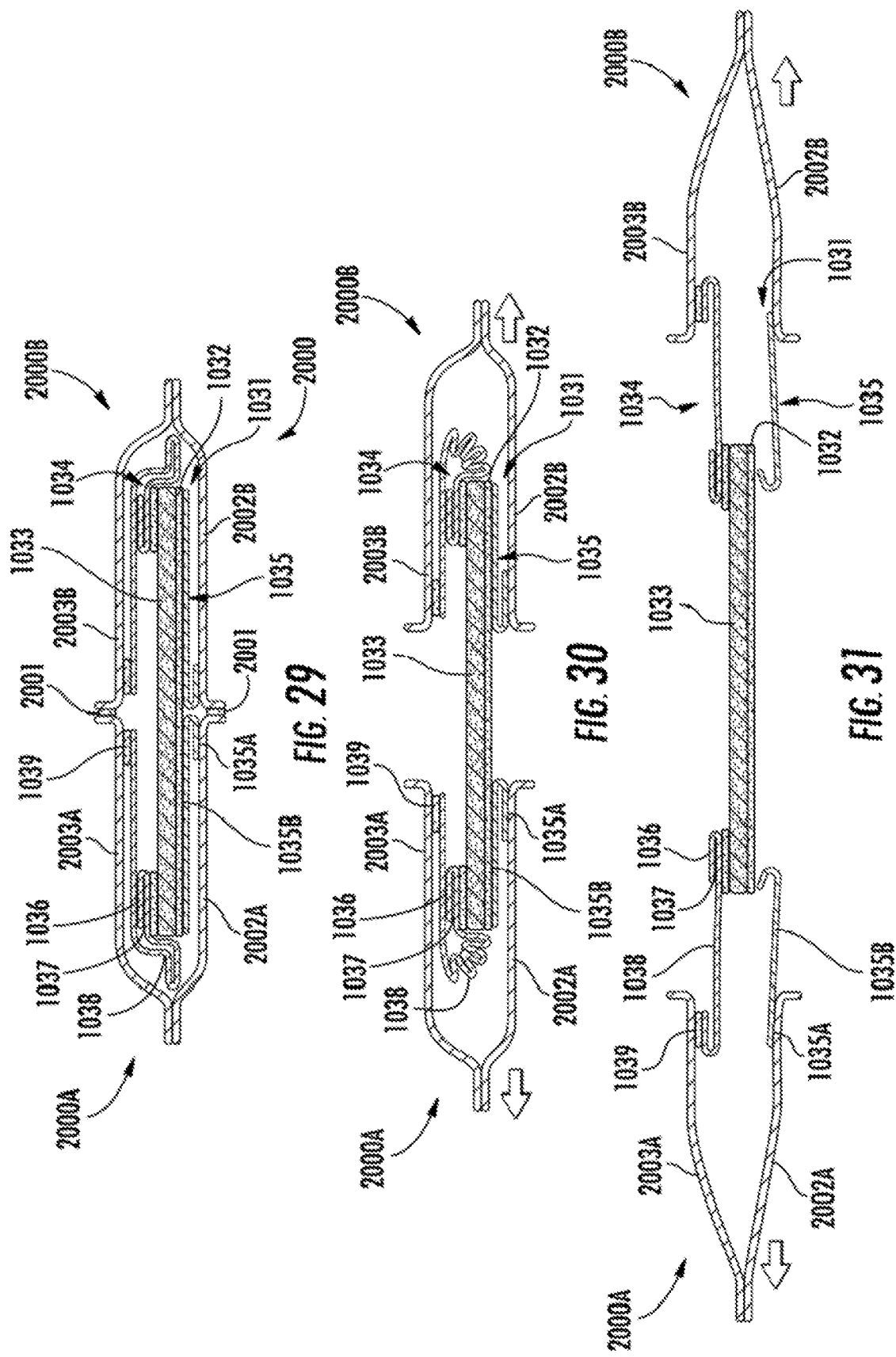

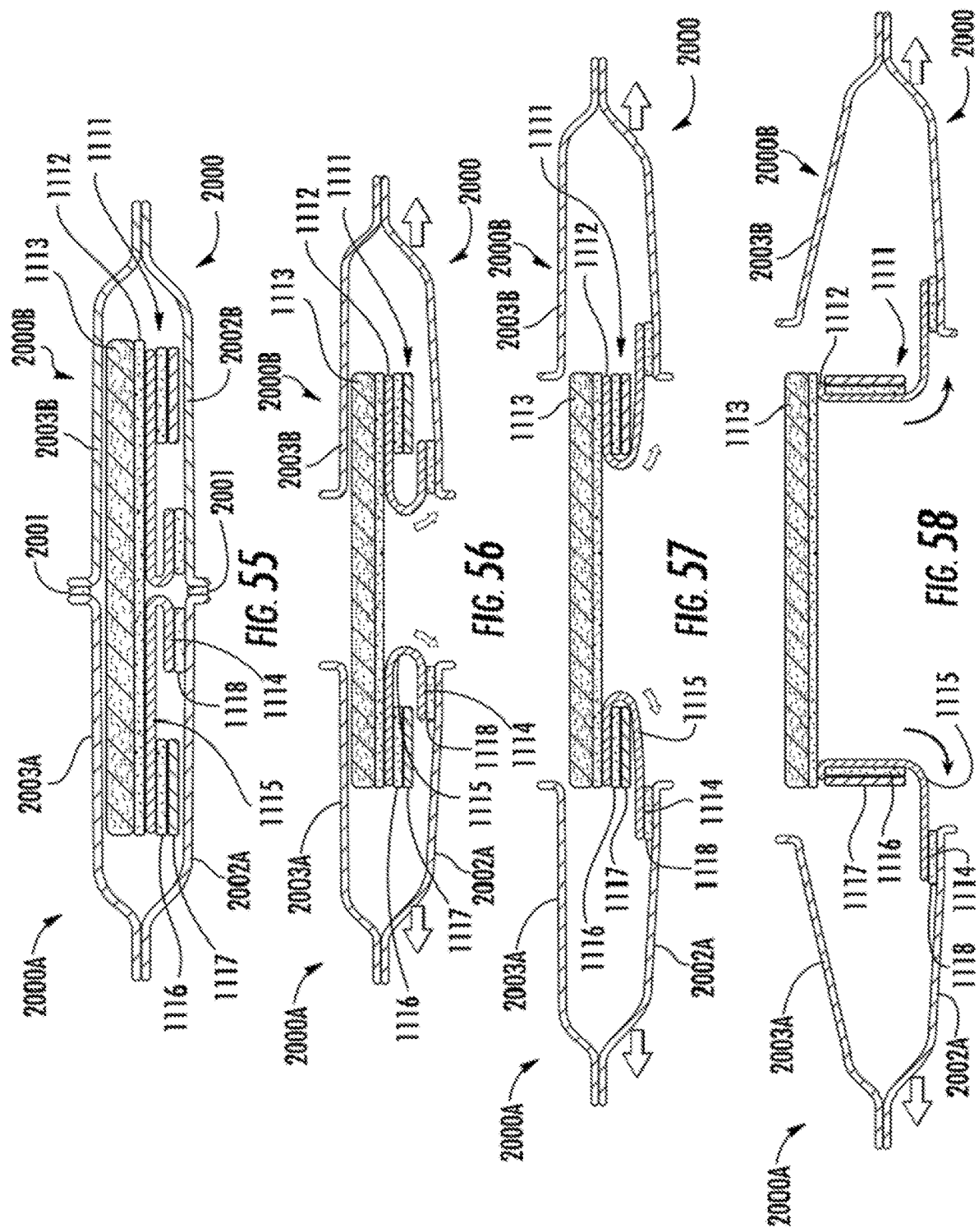

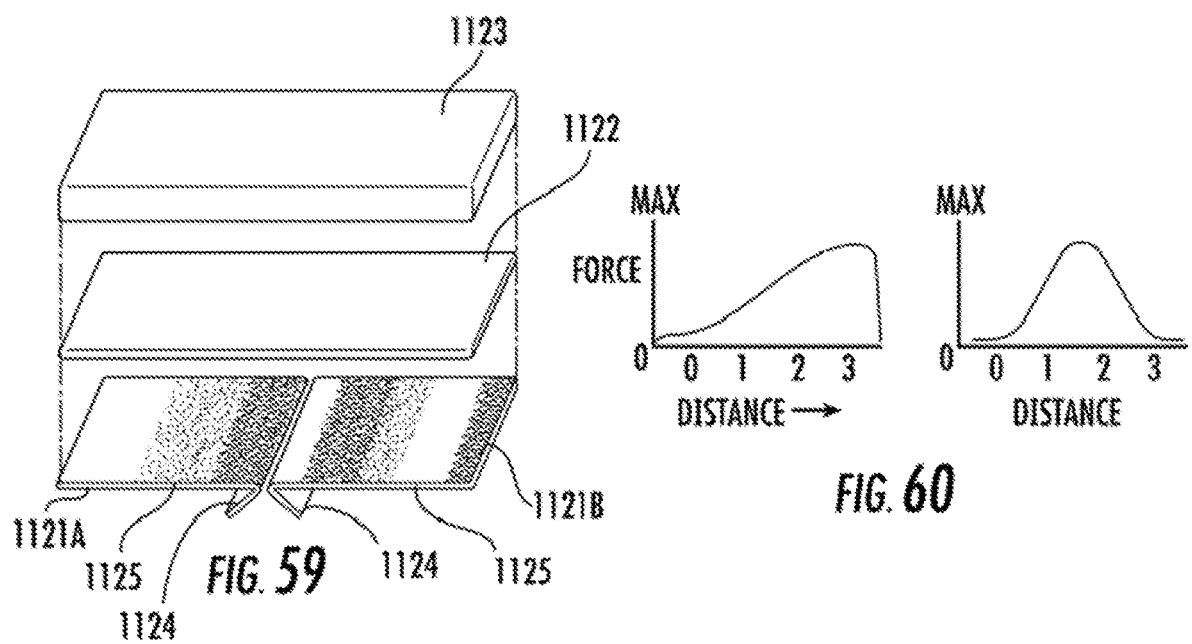
FIG. 59
FIG. 60
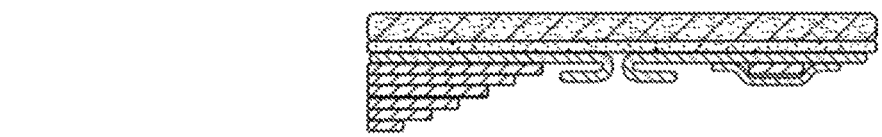
FIG. 61
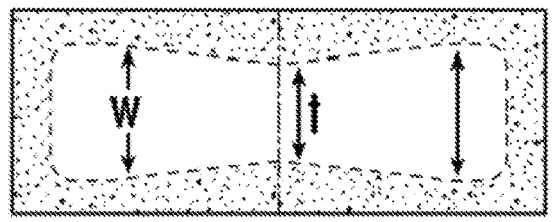
FIG. 62
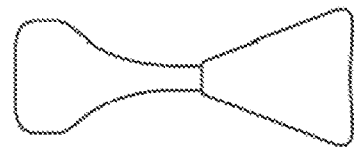
FIG. 63
FIG. 64
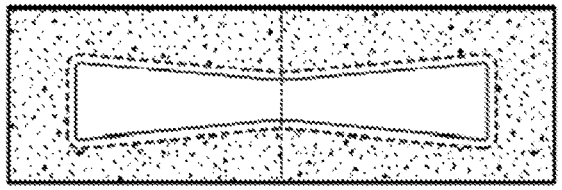
FIG. 65

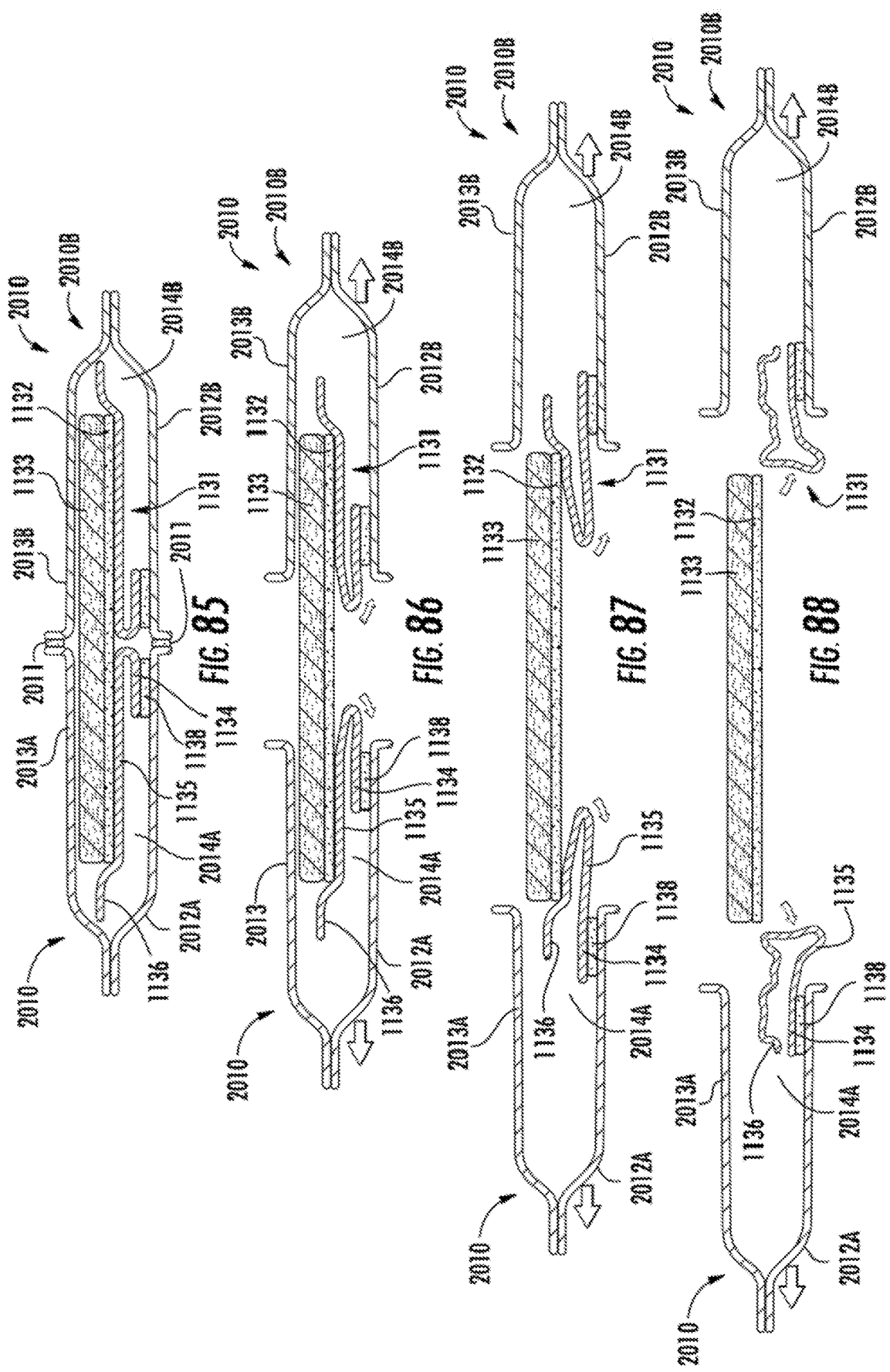

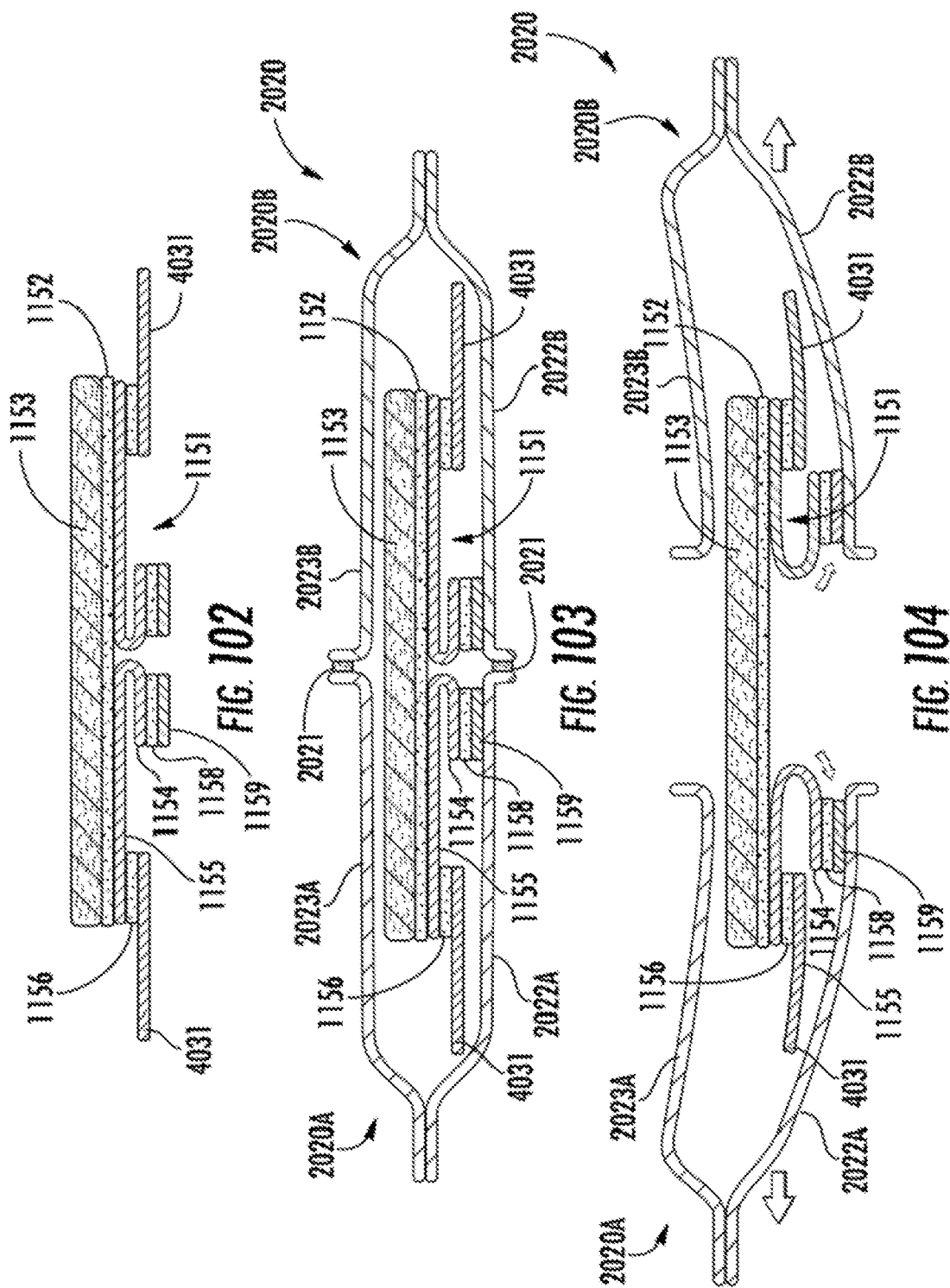

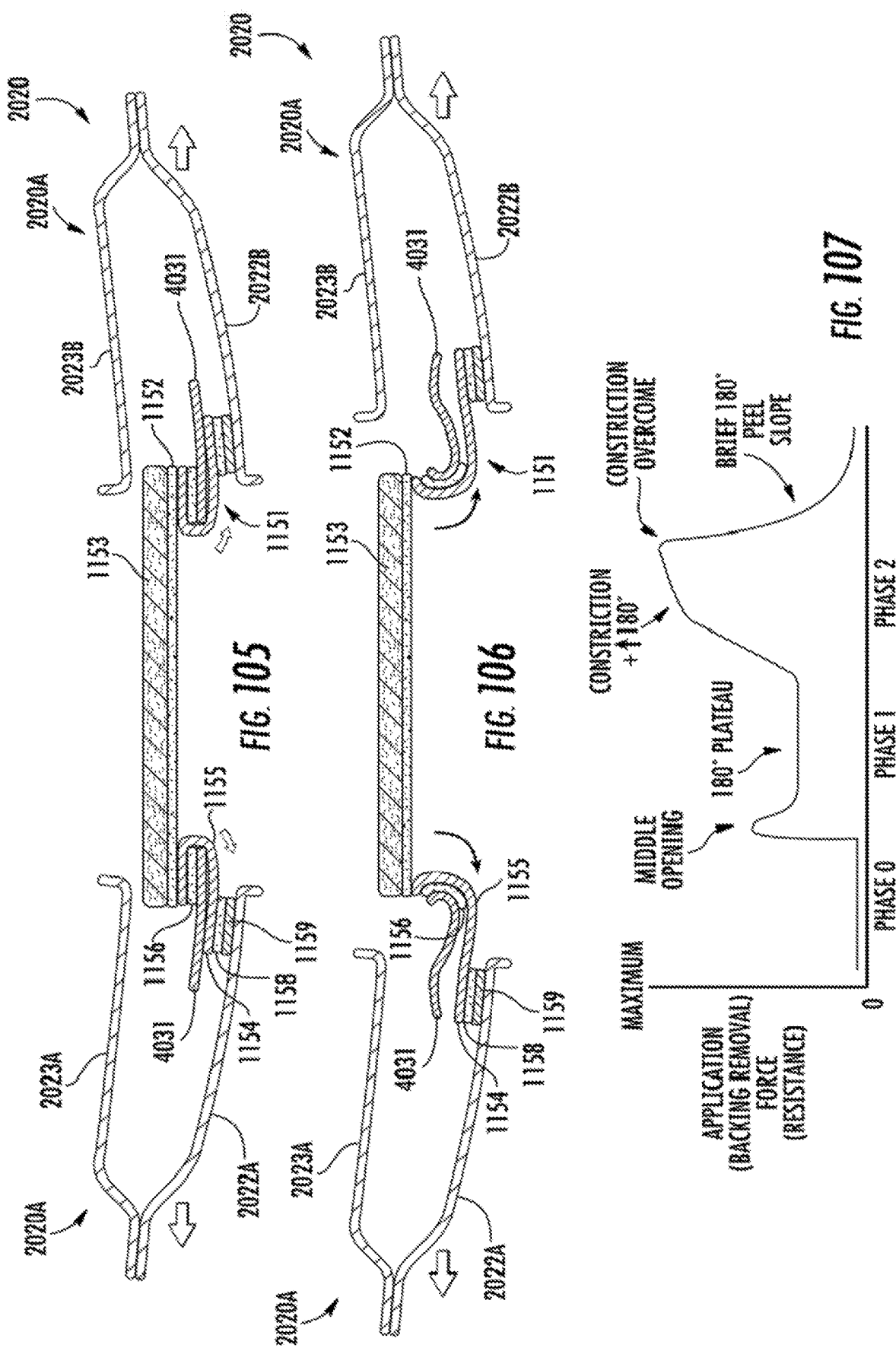

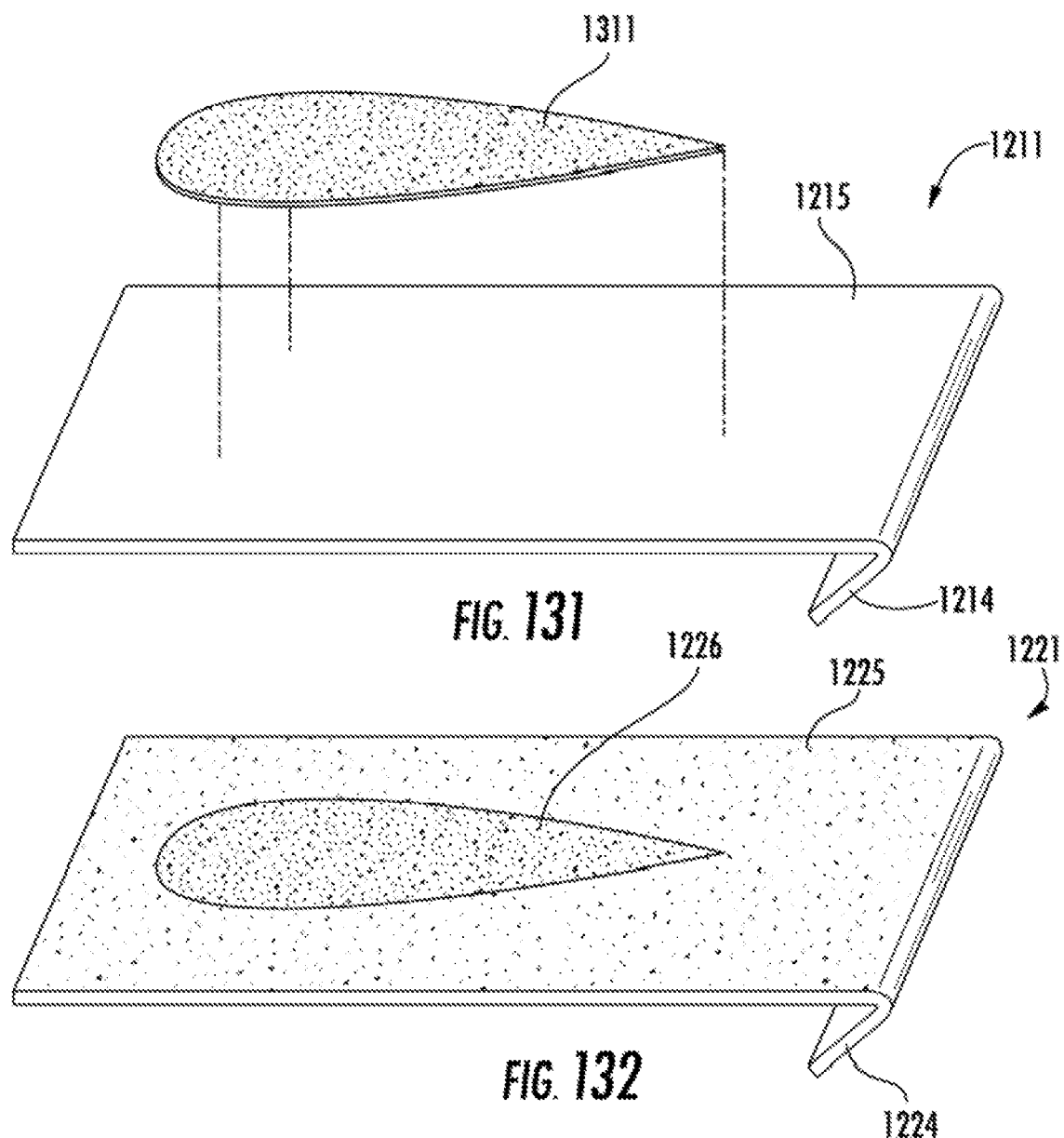

REMOVABLE COVERING AND INTERACTIVE PACKAGING

CROSS-REFERENCE TO PRIORITY APPLICATIONS

This application is a continuation of U.S. patent application Ser. No. 14/255,279 for Removable Covering and Interactive Packaging filed Apr. 17, 2014 (and published Aug. 14, 2014, as Patent Application Publication No. US 2014/0227483), which claims the benefit of International Application No. PCT/US12/61033 for a Removable Covering and Interactive Packaging filed Oct. 19, 2012 (and published Apr. 25, 2013 as WIPO Publication No. WO 2013/059600), which claims the benefit of U.S. Patent Application No. 61/549,317 for a Protective Covering for Adhesive Backed Articles and Methods of Applying the Same (filed Oct. 20, 2011), U.S. Patent Application No. 61/561,522 for a Protective Packaging for Adhesive Backed Articles (filed Nov. 18, 2011), and U.S. Patent Application No. 61/654,748 for a Removable Covering and Interactive Packaging (filed Jun. 1, 2012). Each of the foregoing patent applications and patent publications is hereby incorporated by reference in its entirety.

FIELD OF THE INVENTION

The invention relates to the field of protective layers (e.g., bandages, thin films, sheets, tapes) that are placed over another object, including the human body, and adhered thereto, at least temporarily, via an adhesive.

BACKGROUND

In manufacturing, construction, medicine and other fields there is a frequent requirement to provide a protective barrier on the surface of an object in order to prevent damage or trauma, exposure (e.g., to air to prevent oxidation), contamination (e.g., by infectious agents or hand-borne contaminants), or premature interaction (e.g., adhesion to an unintended object or with undesired alignment). In addition protective barriers can help to align, fix, adhere, or otherwise control an interface between two surfaces. Examples would include the application of laminates or veneers to cover a base structure, tiles or insulation layers to a building feature, a protective layer over sensitive electronic components, or in the application of elastic bandages. A removable covering may itself bear an adhesive layer as a means of temporary fixation to a non-adhesive bearing device. In applications where the protected object itself exhibits an adhesive layer that is intended to adhere the object to another surface, the removable covering is placed over the adhesive layer and is removed as part of the application process. Generally the adherent object must be turned and rotated out of its intended application orientation in order for the covering to be removed. The subsequent need to align the unprotected adhesive surface may lead to mal-position or misapplication. The process of covering exposure for removal can impede effective placement and/or alignment of the surfaces to be adhered. Several examples can illustrate the potential problems with such a maneuver.

In the application of adhesive bandages, the undersurface (adhesive surface) of the bandage must be turned upwards so that the grasping tabs of the backing, typically near the center (pad) of the bandage, can be accessed or visualized. As the covering is removed, the bandage must then be again rotated 180 degrees so that the undersurface can be applied to the skin, and during this reorientation an inadvertent adhesion of one portion of the bandage to another can occur, thus potentially making the bandage unusable. If, during the course of application, the covering is initially only partially removed, the bandage must be rotated without inadvertently removing the remaining attachments, thereby again potentially allowing elements of the bandage to adhere to other parts of the bandage and making the bandage unusable, or by potentially contaminating the bandage. If the covering is totally removed prior to application, this requires that the adhesive surfaces be grasped by the fingers and risks contamination of the central pad of the bandage or poor adherence of the adhesive zone that has been previously grasped prior to attachment to the wound site. Grasping and releasing the bandage at the adhesive surface is particularly difficult when the user is wearing gloves. If the user wishes to apply the bandage under tension so as to create an elastic force within the bandage prior to application, this requires the entire bandage covering to be removed and the adhesive surfaces to be grasped with the users hands, again potentially affecting sterility or adherence of the device. In addition, removal of the covering can be a challenge for patients with limited dexterity, for example in the case in the case of severe arthritis or where one hand may have poor function due to injury. In such instances, removal of the bandage packaging represents an additional step in preparing and positioning the bandage.

Another example representing the potential issues involved when removing a covering can be illustrated in the adherence of decorative coverings or devices to a flat surface, whether these coverings be stiff (e.g., veneers) or flexible (e.g., elastic or woven sheets). When the decorative coverings or devices are stiff, the adhesive layer on the decorative covering or device must be exposed without adherent surfaces being already in alignment, as the devices to be adhered to each other (e.g., a decorative covering and a surface) are brought into proximity it is very easy to have the surfaces inadvertently adhere in a malaligned orientation. In this instance, removal and repositioning of the decorative covering or device is necessitated, and in instances where the strength of the adhesion is great due to either large adhesed surface areas or to the inherent strength of the adhesive, this may lead to damage to either or both of the adhesed surfaces. If the decorative covering is flexible this same issue of alignment after covering removal is encountered, and in addition folds can be created during the course of application that may not be correctable, an damage to either of the adhesed surfaces can occur.

While many other examples exist, it is seen that a covering or covering device (e.g., a protective covering) that can assist in the alignment and placement of one device to be adhered to another surface is desirable. Similarly, combining such a covering device and integrated packaging can help control the position, orientation, application, and use of devices without direct manipulation of the device itself and can assist in removal of the backing. In both these types of uses, if packaging devices are configured to function as either an integral part of a covering device or to facilitate application of said covering device, this may lead to reduced materials and waste and improved ease of use.

SUMMARY

In one aspect, the present invention embraces a substantially planar removable covering for an object. The removable covering typically includes a first free section that is not adhered to the object, a first adhered section that is adhered to the object, and a second adhered section that is adhered to the object. The first adhered section and the second adhered section may be connected to opposite ends of the first free section. The removable covering is typically sufficiently flexible to allow at least partial removal of the first adhered section from the object by application of a force to the removable covering.

In an exemplary embodiment, the force required to remove the removable covering from the object varies at different zones of attachment between the removable covering and the object.

In another exemplary embodiment, the removable covering is adhered to the object such that resistance to removal of the removable covering from the object varies at different zones of attachment between the removable covering and the object.

In another aspect, the present invention embraces a substantially planar removable cover for an object that includes a first adhered section that is adhered to the object, a tab section that is not adhered to the object, a first free section that is not adhered to the object, and a second free section that is not adhered to the object. Typically, the first free section and the second free section are connected to opposite ends of the first adhered section and the same end of the tab section. The removable covering is typically sufficiently flexible to allow at least partial removal of the first adhered section from the object by application of a force to the removable covering.

In an exemplary embodiment, the force required to remove the removable covering from the object varies at different zones of attachment between the removable covering and the object.

In another exemplary embodiment, the removable covering is adhered to the object such that resistance to removal of the removable covering from the object varies at different zones of attachment between the removable covering and the object.

In yet another aspect, the present invention embraces a packaging system for an object and a removable covering that interacts with the removable covering (e.g., via adhesive layers or a constriction mechanism) to facilitate the application of the object. Typically, the packaging system may be removed from the object by applying forces in opposite directions to opposite ends of the packaging system.

In an exemplary embodiment, the packaging system interacts with the removable covering such that the removable covering is removed from the object at the same time the packaging system is removed from the object.

In another exemplary embodiment, the packaging system includes visible design elements that are related in such a way as to convey a story as the packaging system is removed from the object.

In another exemplary embodiment, the packaging system includes visible design elements that present a message or information as the packaging system is removed from the object.

The foregoing illustrative summary, as well as other exemplary objectives and/or advantages of the invention, and the manner in which the same are accomplished, are further explained within the following detailed description and its accompanying drawings.

BRIEF DESCRIPTION OF THE FIGURES

FIG. 1 depicts a side view of an exemplary removable covering and object.

FIG. 2 depicts a side view of an exemplary removable covering and object.

FIG. 3 depicts a side view of the exemplary removable covering and object of FIGS. 1 and 2 in a phase of removal.

FIG. 4 depicts a side view of the exemplary removable covering and object of FIGS. 1 and 2 in a phase of removal.

FIG. 5 depicts a side view of the exemplary removable covering and object of FIGS. 1 and 2 in a phase of removal.

FIG. 6 depicts a side view of the exemplary removable covering and object of FIGS. 1 and 2 in a phase of removal.

FIG. 7 graphically depicts the application force or resistance necessary to remove the exemplary removable covering of FIGS. 1 and 2 from the object as a function of time.

FIG. 23 depicts a side view of an exemplary removable covering and object.

FIG. 24 depicts a side view of the exemplary removable covering and object of FIG. 23 and an exemplary packaging system.

FIG. 25 depicts a side view of the exemplary removable covering, object, and packaging system of FIG. 24 in a phase of removal.

FIG. 26 depicts a side view of the exemplary removable covering, object, and packaging system of FIG. 24 in a phase of removal.

FIG. 29 depicts a perspective view of an exemplary packaging system, removable covering, and object.

FIG. 30 depicts a side view of the exemplary removable covering, object, and packaging system of FIG. 29 in a phase of removal.

FIG. 31 depicts a side view of the exemplary removable covering, object, and packaging system of FIG. 29 in a phase of removal.

FIG. 55 depicts a side view of an exemplary packaging system, removable covering, and object.

FIG. 56 depicts a side view of the exemplary packaging system, removable covering, and object of FIG. 55 in a phase of removal.

FIG. 57 depicts a side view of the exemplary packaging system, removable covering, and object of FIG. 55 in a phase of removal.

FIG. 58 depicts a side view of the exemplary packaging system, removable covering, and object of FIG. 55 in a phase of removal.

FIG. 59 a perspective view of an exemplary object, adhesive layer, and two exemplary removable coverings.

FIG. 60 graphically depicts the force required to remove the left-side removable coverings of FIGS. 59 and 61 and the right-side removable covering of FIG. 61 as a function of distance from the midpoint of the adhesive layer.

FIG. 61 depicts a side view of a two exemplary removable coverings and an object.

FIG. 62 depicts an overhead view of an exemplary packaging system.

FIG. 63 depicts an overhead view of an exemplary removable covering and/or object.

FIG. 64 graphically depicts the force required to remove the packaging system of FIG. 62 from the removable covering of FIG. 63 for the left and ride sides of the removable covering of FIG. 63 as a function of distance from the midpoint of the packaging system.

FIG. 65 depicts an overhead view of an exemplary removable covering and/or object within an exemplary packaging system.

FIG. 85 depicts a side view of an exemplary packaging system, removable coverings, and object.

FIG. 86 depicts a side view of an exemplary packaging system, removable covering, and object in a phase of removal.

FIG. 87 depicts a side view of the exemplary packaging system, removable covering, and object of FIG. 86 in a phase of removal.

FIG. 88 depicts a side view of the exemplary packaging system, removable covering, and object of FIG. 86 in a phase of removal.

FIG. 102 depicts a side view of an exemplary removable covering, exemplary extension sections, and an object.

FIG. 103 depicts a side view of the exemplary removable covering, exemplary extension sections, and object of FIG. 102 in an exemplary packaging system.

FIG. 104 depicts a side view of the exemplary removable covering, exemplary extension sections, object, and exemplary packaging system of FIG. 103 in a phase of removal.

FIG. 105 depicts a side view of the exemplary removable covering, exemplary extension sections, object, and exemplary packaging system of FIG. 103 in a phase of removal.

FIG. 106 depicts a side view of the exemplary removable covering, exemplary extension sections, object, and exemplary packaging system of FIG. 103 in a phase of removal.

FIG. 107 graphically depicts the application force or resistance necessary to remove the packaging system and exemplary removable covering of FIG. 103 from the object as a function of time.

FIG. 119 depicts a perspective view of yet another exemplary packaging system.

FIG. 120 depicts an overhead view of an exemplary packaging system.

FIG. 121 depicts an overhead view of the exemplary packaging system of FIG. 120 in a phase of removal.

FIG. 122 depicts an overhead view of the exemplary packaging system of FIG. 120 in another phase of removal.

FIG. 123 depicts an overhead view of the exemplary packaging system of FIG. 120 in yet another phase of removal.

FIG. 124 depicts an overhead view of another exemplary packaging system.

FIG. 125 depicts an overhead view of the exemplary packaging system of FIG. 120 in a phase of removal.

FIG. 126 depicts an overhead view of the exemplary packaging system of FIG. 120 in another phase of removal.

FIG. 127 depicts a perspective view of an exemplary packaging system, removable covering, and object in a phase of manufacture.

FIG. 128 depicts a perspective view of an exemplary removable covering.

FIG. 129 depicts a perspective view of the exemplary removable covering of FIG. 128 and an adhesive strip in a phase of manufacture.

FIG. 130 depicts a perspective view of the exemplary removable covering and adhesive strip of FIG. 129 as configured after manufacturing.

FIG. 131 depicts a perspective view of an exemplary removable covering and an adhesive strip in a phase of manufacture.

FIG. 132 depicts a perspective view of the exemplary removable covering and adhesive strip of FIG. 131 as configured after manufacturing.

Figure 133:
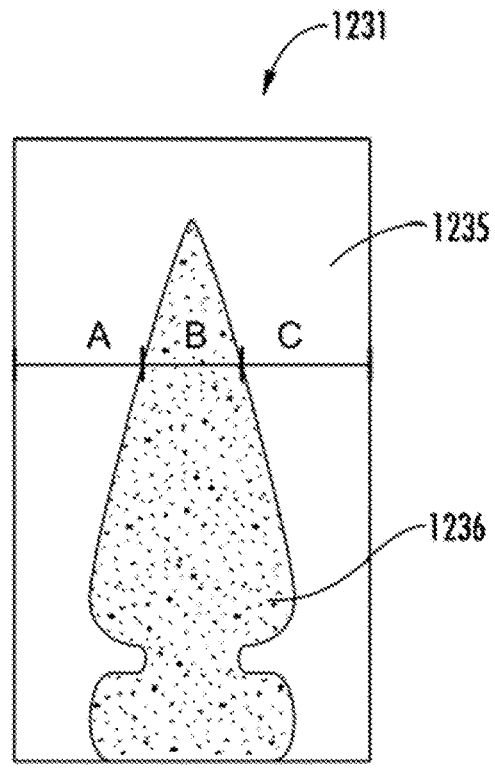

FIG. 133 depicts an overhead view of an exemplary removable covering including a varied adhesion zone.

Figure 134:
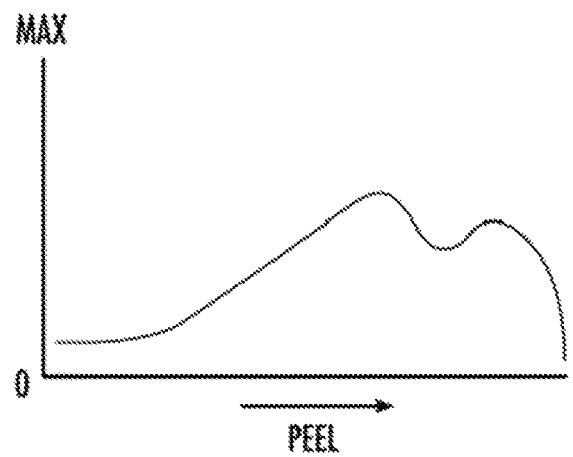

FIG. 134 graphically depicts the application force or resistance necessary to remove the exemplary removable covering of FIG. 133 from an object as a function of time.

Figure 135:
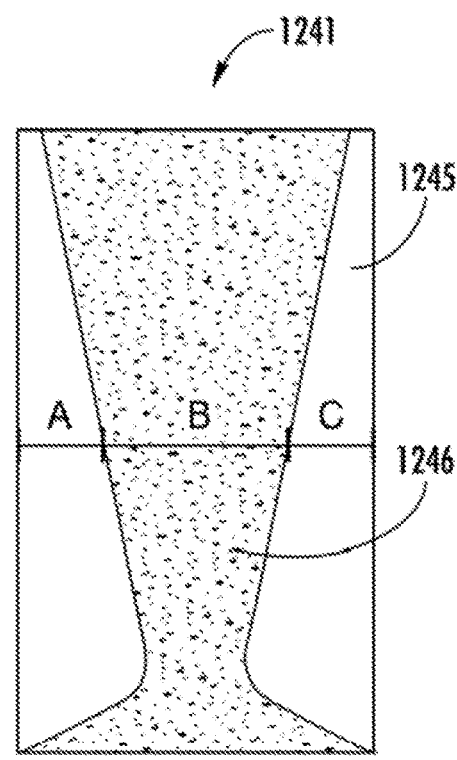

FIG. 135 depicts an overhead view of another exemplary removable covering including a varied adhesion zone.

Figure 136:
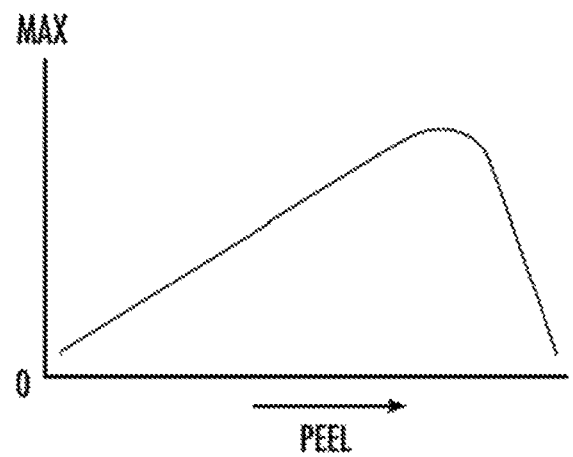

FIG. 136 graphically depicts the application force or resistance necessary to remove the exemplary removable covering of FIG. 135 from an object as a function of time.

Figure 137:
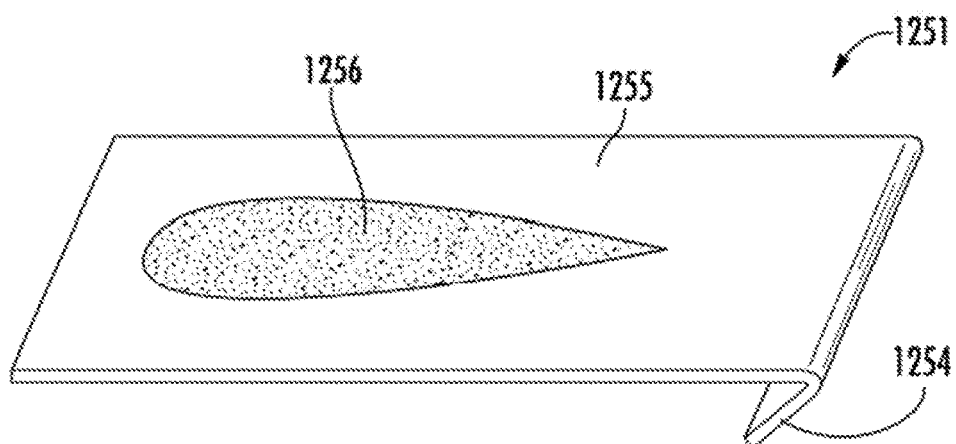

FIG. 137 depicts a perspective view of an exemplary removable covering including a varied adhesion zone.

Figure 138:
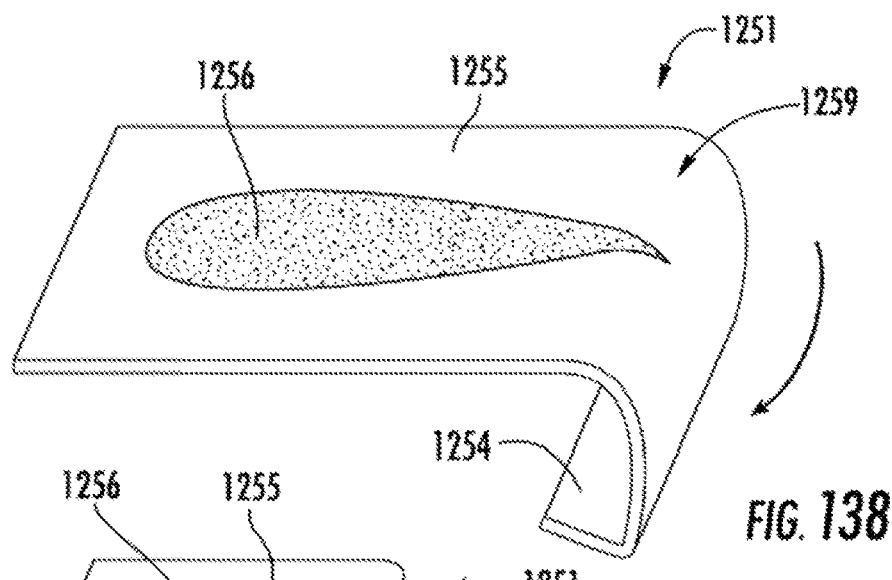

FIG. 138 depicts a perspective view of the exemplary removable covering of FIG. 137 in a phase of removal.

Figure 139:
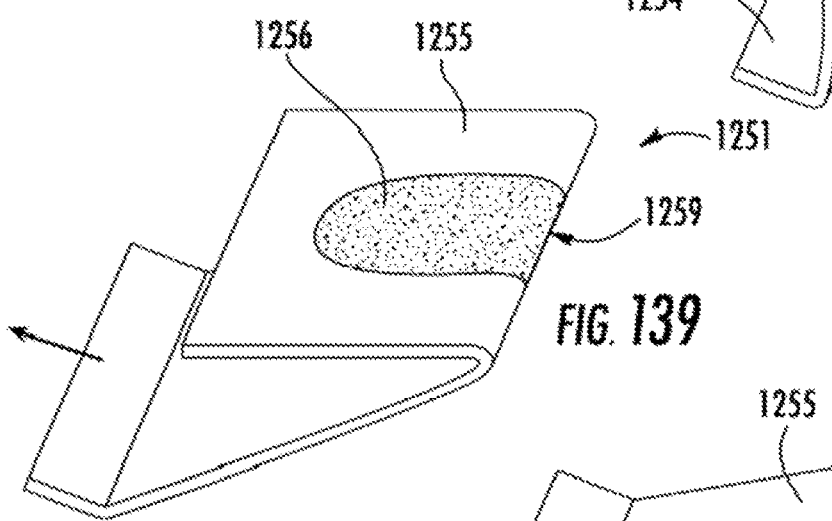

FIG. 139 depicts a perspective view of the exemplary removable covering of FIG. 137 in another phase of removal.

Figure 140:
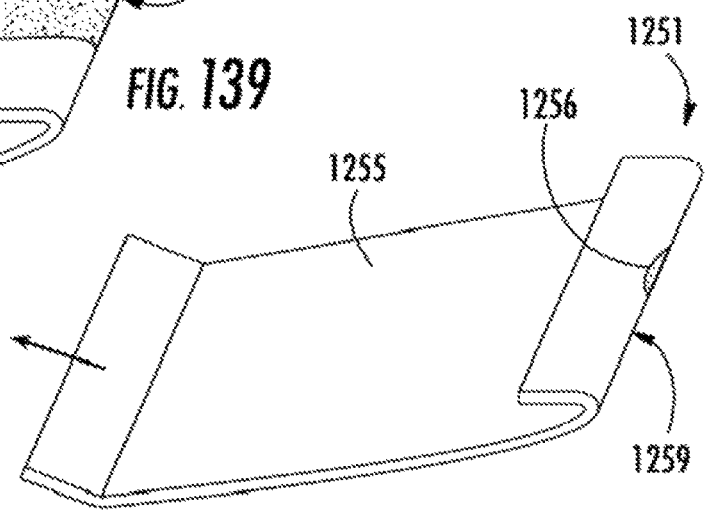

FIG. 140 depicts a perspective view of the exemplary removable covering of FIG. 137 in yet another phase of removal.

Figure 141:
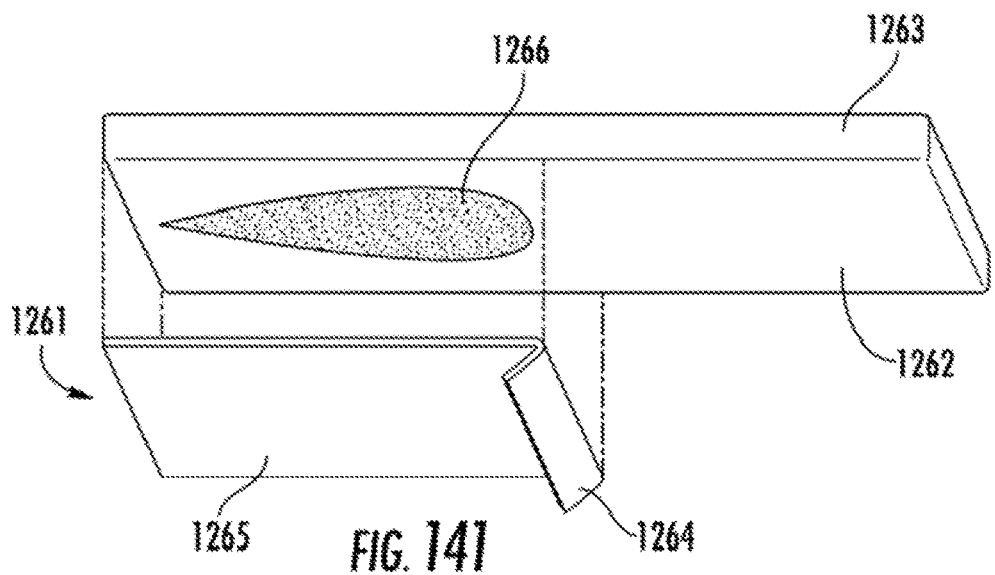

FIG. 141 depicts a perspective view of an exemplary removable covering before application to an object that includes a varied adhesion zone.

Figure 142:
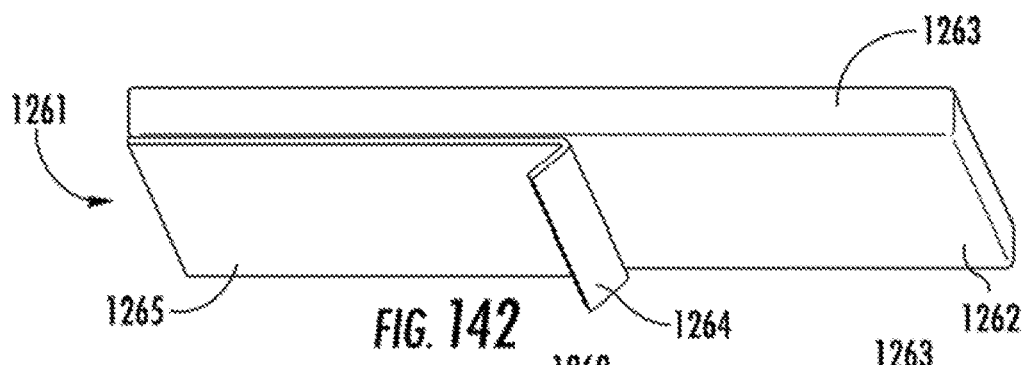

FIG. 142 depicts a perspective view of the exemplary removable covering of FIG. 141 as applied to the object.

Figure 143:
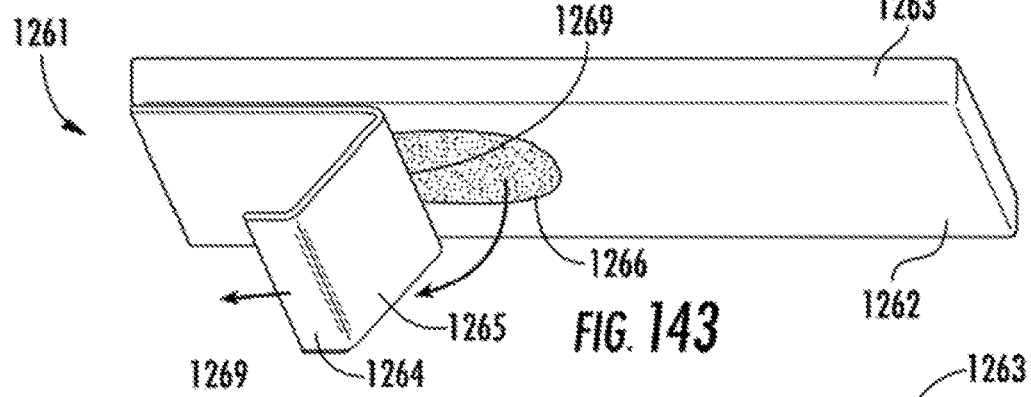

FIG. 143 depicts a perspective view of the exemplary removable covering of FIG. 141 in a phase of removal from the object.

Figure 144:
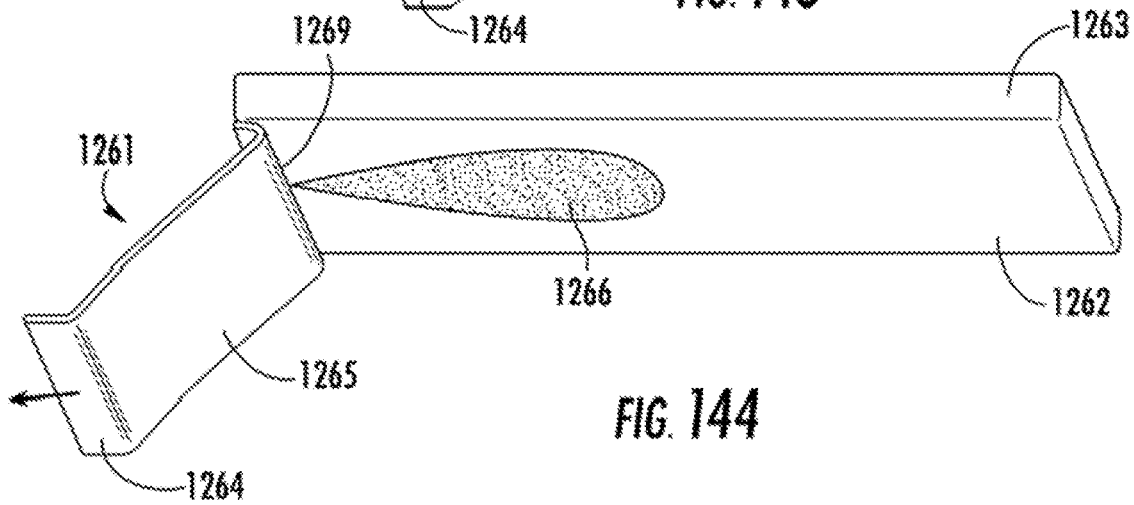

FIG. 144 depicts a perspective view of the exemplary removable covering of FIG. 141 in another phase of removal from the object.

Figure 145:
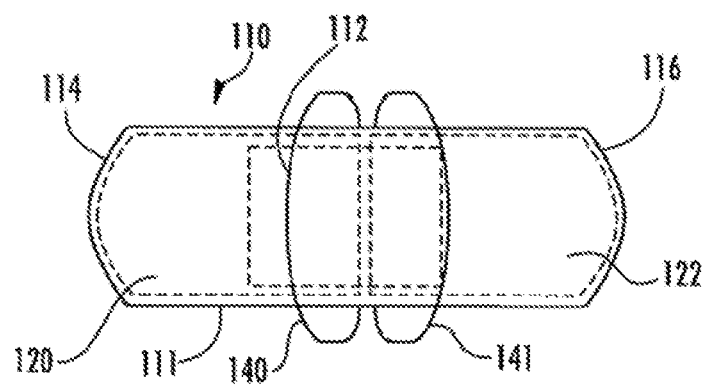

FIG. 145 depicts an overhead view of an exemplary removable covering and an object.

Figure 146:
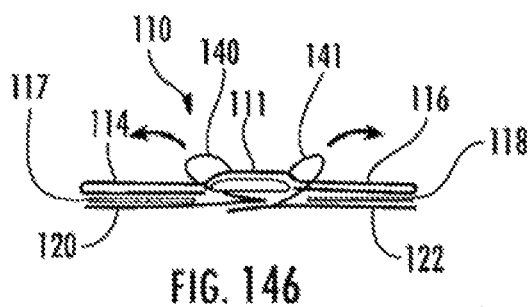

FIG. 146 depicts a side view of the exemplary removable covering of FIG. 145.

Figure 147:
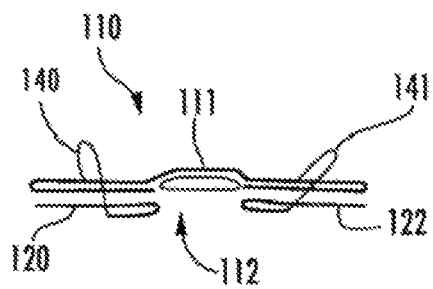

FIG. 147 depicts a side view of the exemplary removable covering of FIG. 145 in a phase of removal from an object.

Figure 148:
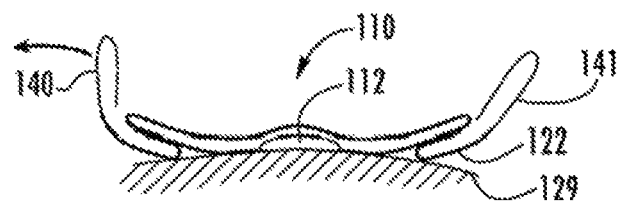

FIG. 148 depicts a side view of the exemplary removable covering of FIG. 145 in a phase of removal from an object and a phase of applying the object to a surface.

Figure 149:
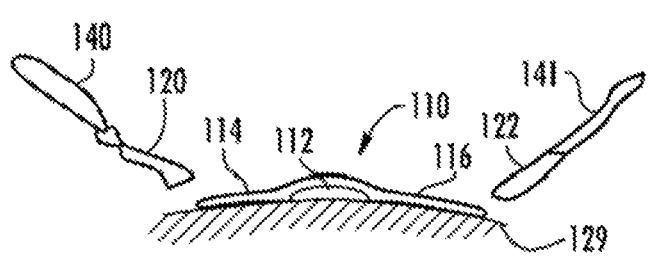

FIG. 149 depicts a side view of the exemplary removable covering of FIG. 145 in a phase of removal from an object and a phase of applying the object to a surface.

Figure 150:
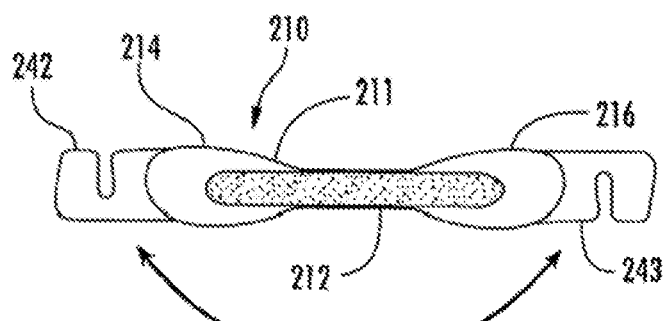

FIG. 150 depicts an overhead view of an exemplary removable covering and an object.

Figure 151:
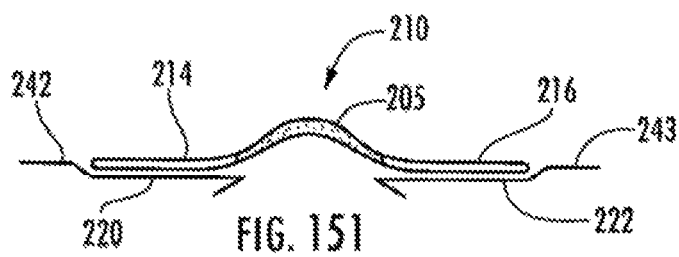

FIG. 151 depicts a side view of the exemplary removable covering of FIG. 150.

Figure 152:
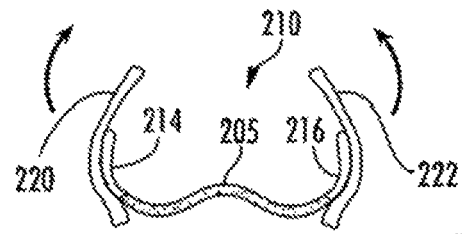

FIG. 152 depicts a side view of the exemplary removable covering of FIG. 150 in a phase of preparing the removable covering and object for application to a surface.

Figure 153:
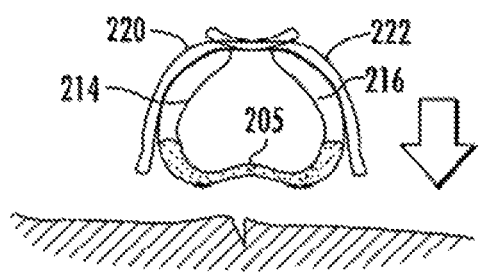

FIG. 153 depicts a side view of the exemplary removable covering of FIG. 150 in a phase of preparing the removable covering and object for application to a surface and applying the removable covering and object to a surface.

Figure 154:
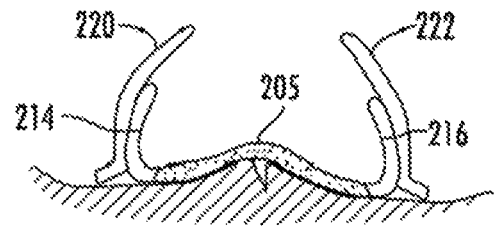

FIG. 154 depicts a side view of the exemplary removable covering of FIG. 150 in a phase of applying the removable covering and object to a surface.

DETAILED DESCRIPTION

In one aspect, the present invention embraces a removable covering (e.g., a backing or backing device) for a receiving surface (e.g., an object having an adhesive layer). The removable covering facilitates the positioning, orientation, application, and use of the receiving surface as well as the removal of the removable covering.

In particular, the invention relates to removable coverings that peel away from objects (e.g., protected devices) to expose an adhesive that may then be applied to a receiving surface that is covered by the object upon application. In a particular embodiment, the invention relates to the construction of the removable covering and the level of resistance to peeling that the construction of the removable covering brings to the object. The resistance to peeling may vary along the peeling path to allow for proper placement of the removable covering onto the receiving surface before final application of the entire covering. Typically, the removable covering comprises a material of sufficient flexibility to allow at least partial removal from a protected device or object by application of a peel force vector applied to a section or structural feature of the removable covering (e.g., backing).

As described herein, the protected devices and/or objects are typically substantially planar, rectangular-shaped, and symmetrical. That said, exemplary embodiments of the present invention may include objects, removable coverings, and packaging systems that are not planar, rectangular, or symmetrical. For example, a circular-shaped object, removable covering, and/or packaging system is within the scope of the present invention. Furthermore, for particularly long objects (e.g., having significantly greater lengths than widths), the removable coverings and/or packaging systems may be removed in a direction parallel to the width of the object, rather than the length as disclosed herein.

The disclosure of this invention includes use of numerous mechanisms for changing the resistance of the peel strength of the removable covering attached to a protective layer to be applied to a receiving surface. Each of these mechanisms is conducive to mixing and interchanging on any given device. The construction of the removable covering is disclosed with certain portions shown as a continuous layer, but such disclosure is not limiting of the invention. The invention encompasses embodiments in which any layer comprises multiple portions. This disclosure often refers to an adhesive layer from which the removable covering is peeled. The adhesive layer may peel away while remaining on the removable layer (i.e., leaving the receiving surface free of adhesive) or the removable covering may peel away and leave the adhesive layer on the receiving surface.

Aspects of exemplary removable coverings and packaging systems are described herein with reference to numerous figures. In the description, a single side of a removable covering or packaging system may be described (e.g., only the left or right side). The removable covering or packaging system typically includes left and right sides that are mirror images of each other (i.e., the left and right sides have the same components), unless otherwise noted. Thus, the description of a single side of a removable covering or packaging system may be equally applied to the other side. That said, it is within the scope of the present invention to employ single-sided removable coverings and/or packaging systems.

Furthermore, aspects of exemplary removable coverings and packaging systems are described herein with reference to phases of removal. As will be recognized, these phases of removal generally correspond to zones of attachment between the removable covering and the object.

FIG. 1 depicts a side view of an exemplary removable covering 1001 and an object 1003 having a receiving surface 1002. Each side (i.e., the left and right sides) of the exemplary removable covering 1001 includes a primary tab 1004 (e.g., a central terminus or free section), a lateral free section 1008, and a secondary tab 1007 (e.g., a lateral terminus or free section) that are not adhered to the receiving surface 1002 of the object 1003. The removable covering 1001 also includes a central section 1005 (e.g., an adhered section) and a lateral section 1006 (e.g., an adhered section) that are adhered to the receiving surface 1002.

FIG. 2 depicts a side view of another exemplary removable covering wherein the receiving surface 1002 is an adhesive layer. In this regard, the adhesive layer 1002, which may be on the object 1003 or the removable covering 1001, is positioned between the removable covering 1001 and the object 1003. FIGS. 3-6 depict side views of the exemplary removable covering 1001 and object 1003 in different phases of removal, while FIG. 7 graphically depicts the application force or resistance necessary to remove the exemplary removable covering 1001 from the object 1003 as a function of time. In FIG. 7, "Phase 0" corresponds to FIGS. 1 and 2; "Phase 1" corresponds to FIG. 3; "Phase 1B" corresponds to FIG. 4; "Phase 2" corresponds to FIG. 5; and "Phase 3" corresponds to FIG. 6.

Figure 8:
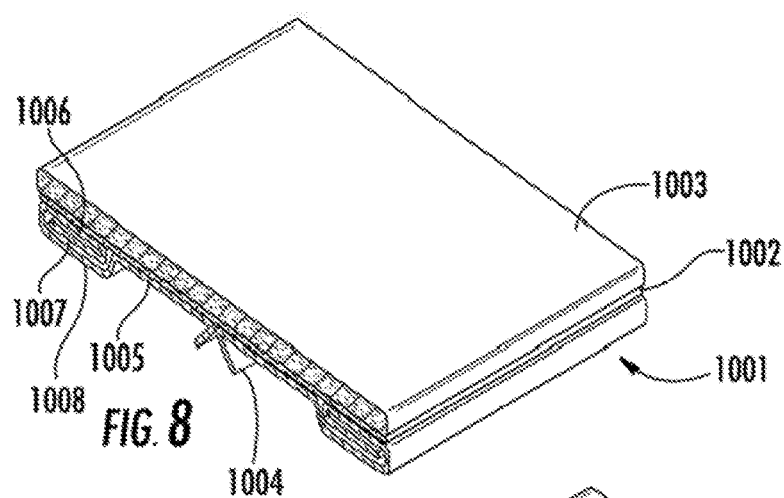
FIG. 8 depicts a perspective view of the exemplary removable covering and object of FIGS. 1 and 2.
Figure 9:
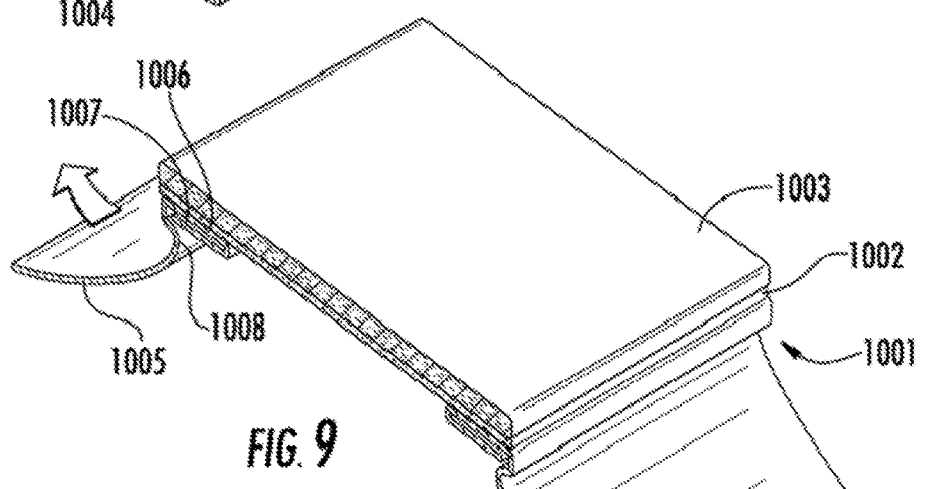
FIG. 9 depicts a perspective view of the exemplary removable covering and object of FIGS. 1 and 2 in the same phase of removal as shown in FIG. 4.
Figure 10:
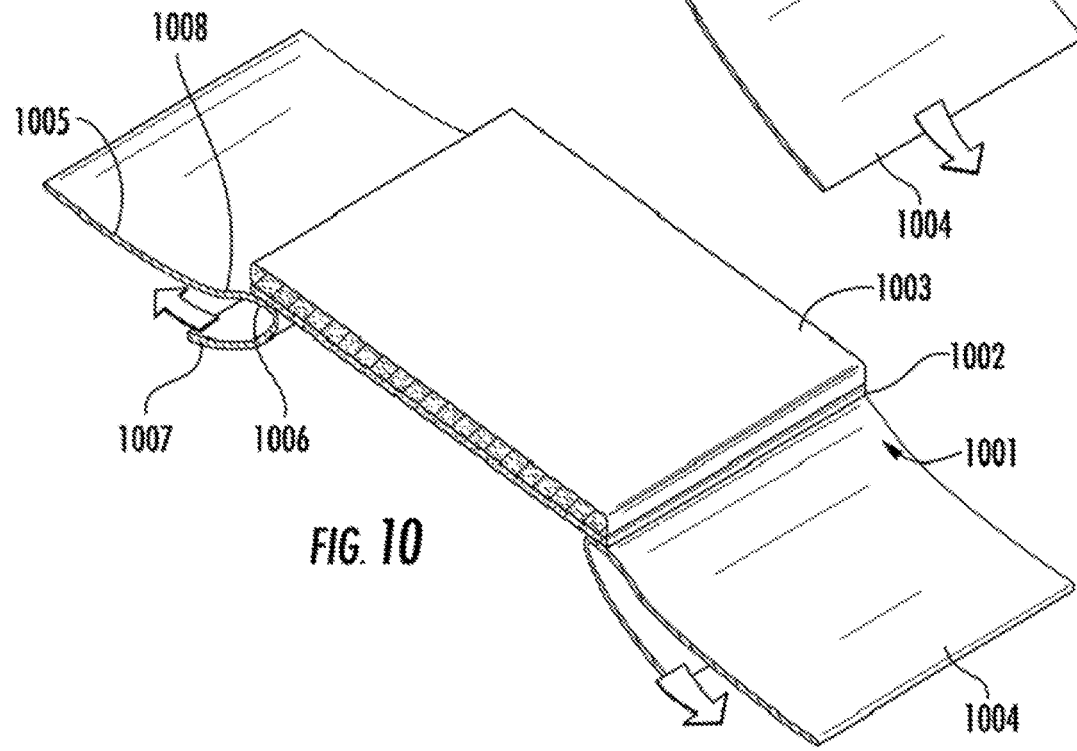
FIG. 10 depicts a perspective view of the exemplary removable covering and object of FIGS. 1 and 2 in the same phase of removal as shown in FIG. 6.

FIG. 8 depicts a perspective view of the exemplary removable covering 1001, receiving surface 1002, object 1003 of FIGS. 1 and 2 (i.e., Phase 0). FIG. 9 depicts a perspective view of the exemplary removable covering 1001, receiving surface 1002, and object 1003 of FIGS. 1 and 2 in the same phase of removal as shown in FIG. 4 (i.e., Phase 1B). FIG. 10 depicts a perspective view of the exemplary removable covering 1001, receiving surface 1002, and object 1003 of FIGS. 1 and 2 in the same phase of removal as shown in FIG. 6 (i.e., Phase 3).

In this exemplary embodiment, Phase 0 is followed by the grasping of a primary tab 1004 which requires the application of a midline separation force. Phase 1 requires a force to overcome a 180 degree peel strength resistance. Phase 1B may require a force to overcome a 180 degree peel strength resistance (e.g., if the lateral free section 1008 is adhered to the secondary tab 1007) or no force (e.g., if the lateral free section 1008 is not adhered to the secondary tab 1007). During Phase 2, there is a shear resistance to removal, but the secondary tab 1007 is exposed. See e.g., FIG. 5. Thus, the secondary tab 1007 may be pulled during Phase 3 to overcome a second 180 degree peel strength resistance.

In this regard, exemplary embodiments of the present invention embrace a removable covering so constructed and oriented that when applied to a receiving surface said removable covering exhibits a fold such that portions of both flat surfaces of the removable covering are adhered to different sections of the receiving surface. A central terminus does not adhere to the receiving surface and functions as a primary tab for peeling a central section of the removable covering from the receiving surface at a peel angle that is between 90 and 180 degrees. Upon completion of the 90 to 180 degree peel with the same force vector, the peel angle transitions to a 0 degree peel angle (shear) with a higher peel resistance within a lateral section that is continuous with the central section. A second embodiment incorporates a secondary tab continuous with the lateral section and not adhered to the receiving surface to allow a secondary peel angle between 90 and 180 degrees to be applied to the lateral section.

Figure 11:
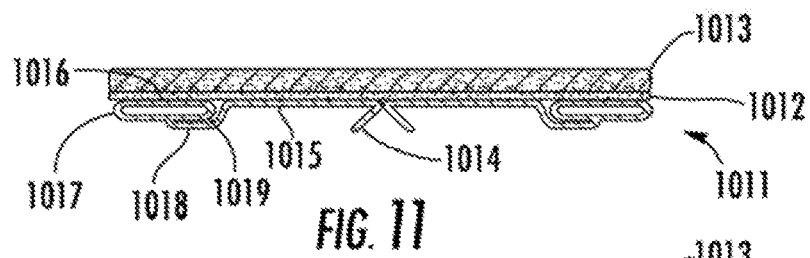
FIG. 11 depicts a side view of an exemplary removable covering and object.
Figure 12:
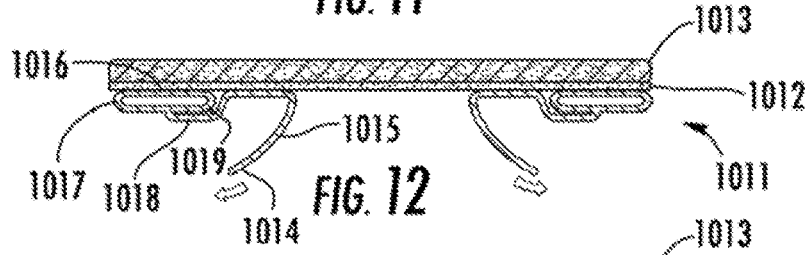
FIG. 12 depicts a side view of the exemplary removable covering and object of FIG. 11 in a phase of removal.
Figure 13:
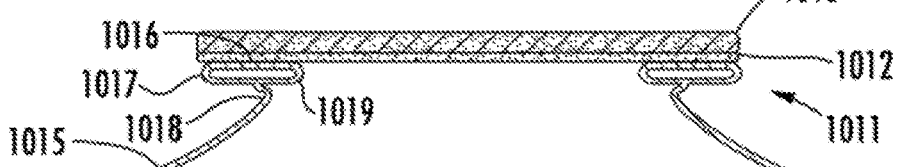
FIG. 13 depicts a side view of the exemplary removable covering and object of FIG. 11 in a phase of removal.

FIG. 11 depicts a side view of an exemplary removable covering 1011 and an object 1013 having a receiving surface 1012. Each side (i.e., the left and right sides) of the exemplary removable covering 1011 includes a primary tab 1014 (e.g., a central terminus or free section), a first free section 1017, a tab section 1018, and a second free section 1019 that are not adhered to the receiving surface 1012 of the object 1013. The removable covering 1011 also includes a central section 1015 (e.g., an adhered section) and a lateral section 1016 (e.g., a first adhered section) that are adhered to the receiving surface 1012.

As shown, the first free section 1017 and second free section 1019 are connected to opposite ends of the lateral section 1016. Additionally, the first free section 1017 and second free section 1019 are connected to the same end of the tab section 1018. In this regard, the first free section 1017, second free section 1019, and the later section 1016 form a loop connected to tab section 1018.

Figure 16:
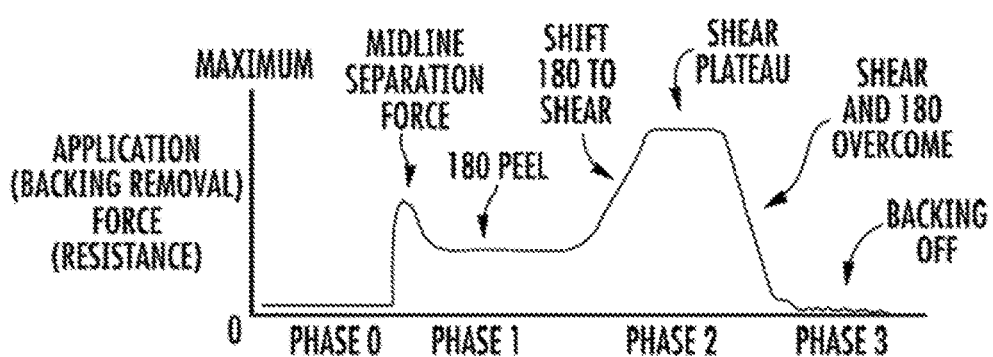
FIG. 16 graphically depicts the application force or resistance necessary to remove the exemplary removable covering of FIG. 11 from the object as a function of time.

FIGS. 12-15 depict side views of the exemplary removable covering 1011 and object 1013 in different phases of removal, while FIG. 16 graphically depicts the application force or resistance necessary to remove the exemplary removable covering 1011 from the object 1013 as a function of time. In FIG. 16, "Phase 0" corresponds to FIG. 11; "Phase 1" corresponds to FIGS. 12 and 13; "Phase 2" corresponds to FIG. 14; and "Phase 3" corresponds to FIG. 15. FIG. 16 illustrates, for example, that the force required to remove the removable covering 1011 from the object 1013 is greatest at the second to last zone of attachment.

Figure 14:
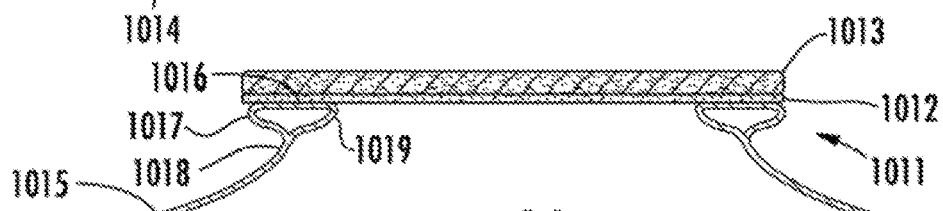
FIG. 14 depicts a side view of the exemplary removable covering and object of FIG. 11 in a phase of removal.
Figure 15:
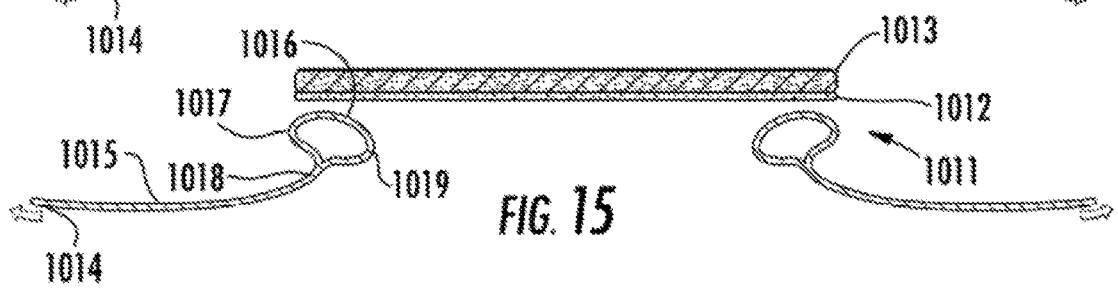
FIG. 15 depicts a side view of the exemplary removable covering and object of FIG. 11 in a phase of removal.
Figure 17:
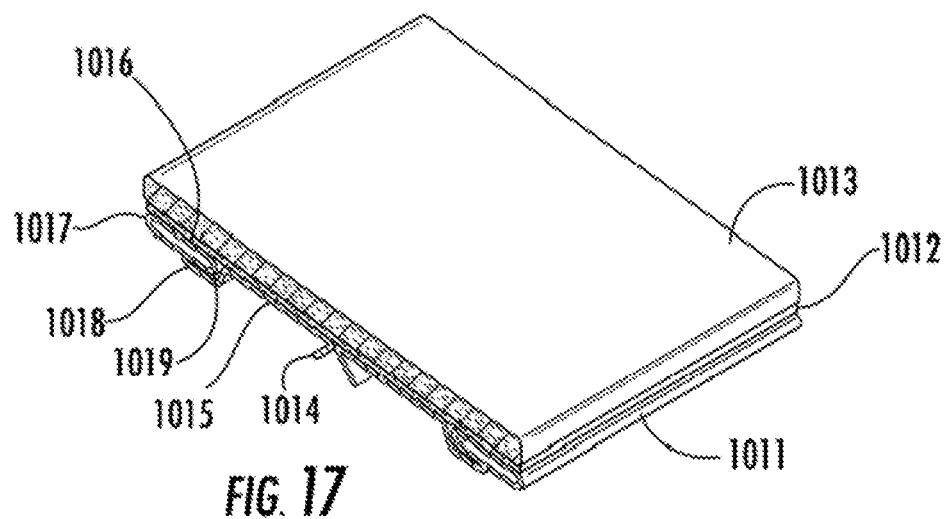
FIG. 17 depicts a perspective view of the exemplary removable covering and object of FIG. 11.
Figure 18:
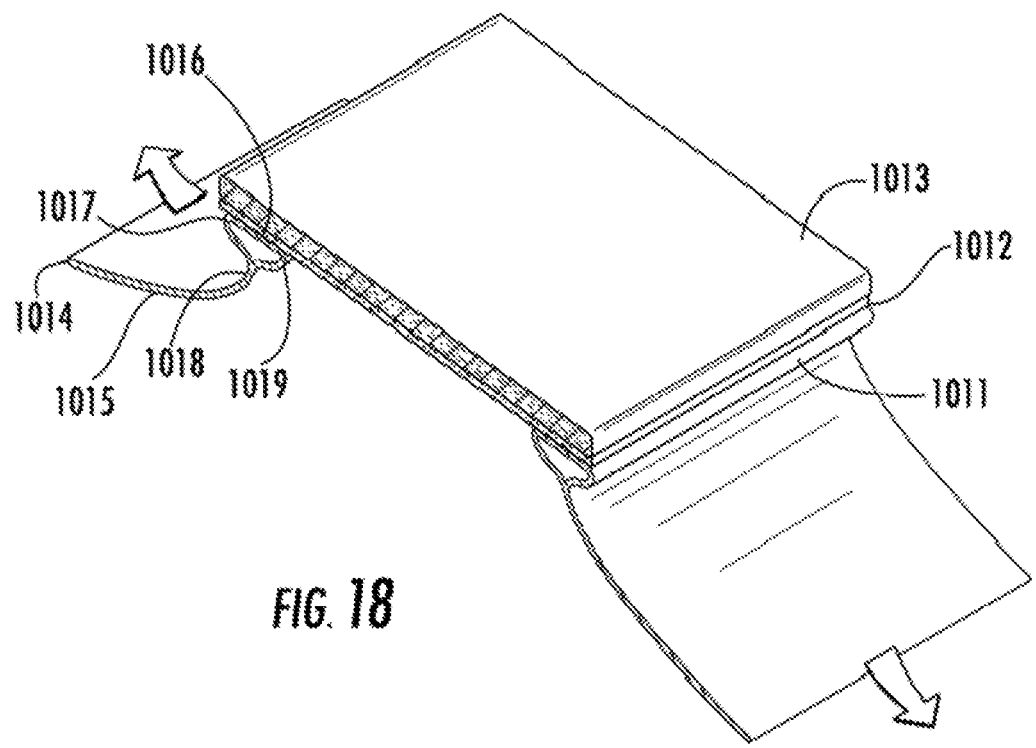
FIG. 18 depicts a perspective view of the exemplary removable covering and object of FIG. 11 in the same phase of removal as shown in FIG. 14.

FIG. 17 depicts a perspective view of the exemplary removable covering 1011, receiving surface 1012, and object 1013 of FIG. 11 (i.e., Phase 0). FIG. 18 depicts a perspective view of the exemplary removable covering 1011, receiving surface 1012, and object 1013 of FIG. 1 in the same phase of removal as shown in FIG. 14 (i.e., Phase 2).

In this exemplary embodiment, Phase 0 is followed by the grasping of a primary tab 1014 which requires the application of a midline separation force. Phase 1 requires a force to overcome a 180 degree peel strength resistance. The early portion of Phase 2 (i.e., the shift from a 180 degree peel strength resistance to a shear peel strength resistance) occurs after reaching the orientation shown in FIG. 14. The later portion of Phase 2 (i.e., the shear plateau) occurs when the pulling force is primarily lateral. During Phase 3, the loop releases from the receiving surface 1012.

In such exemplary removable coverings including a loop, the degree of transfer between 180 degree peel strength resistance and shear peel strength resistance may be adjusted by varying the junction point of the tab section 1018 and the loop. For example, if the first free section 1017 is closer to the outer edge of the receiving surface 1012 (i.e., the tab section 1018 connects to the loop further from the center of the receiving surface), the resistance to removal will shift from a 180 degree peel strength resistance to a shear peel strength resistance more quickly. In other words, the slope of the force/resistance curve in the early portion of Phase 2 in FIG. 16 will be greater (i.e., a steeper slope).

In this regard, exemplary embodiments of the present invention embrace a removable covering so constructed and oriented that when applied to a receiving surface said removable covering exhibits a lateral section defining a loop such that portions of both flat surfaces of the removable covering are adhered to different sections of the receiving surface. The lateral section is continuous with a central section along the non-adhered surface of the lateral section. The connection between the lateral and central sections can be in any position along the length of the lateral section. A central terminus does not adhere to the receiving surface and functions as a primary tab for peeling a central section of the removable covering from the receiving surface at a peel angle that is between 90 and 180 degrees. Upon completion of the 90 to 180 degree peel with the same force vector, the peel angle transitions to at least a partial 0 degree peel angle (shear) with a higher peel resistance within a lateral section that is continuous with the central section. With an increasing force vector and no change in direction, the peel resistance is overcome, and the covering is removed from the receiving surface.

Figure 19:
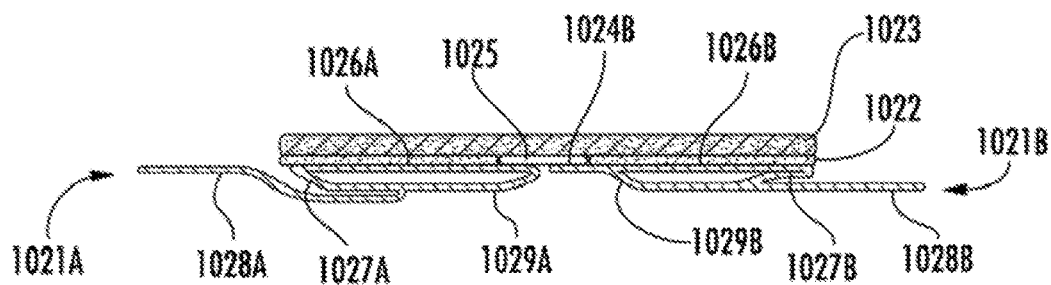
FIG. 19 depicts a side view of two exemplary removable coverings and object.

FIG. 19 depicts a side view of two exemplary removable coverings 1021A and 1021B and an object 1023 having a receiving surface 1022 and a central feature 1025 (e.g., an absorbent pad or non-adhesive surface). The removable covering on the left 1021A includes a tab section 1028A, a first free section 1027A, and a second free section 1029A that are not adhered to the receiving surface 1022 of the object 1023. The removable covering on the left 1021A also includes a lateral section 1026A that is adhered to the receiving surface 1022 and covers at least a portion of the central feature 1025.

The removable covering on the right 1021B includes a tab section 1028B, a first free section 1027B, and a second free section 1029B that are not adhered to the receiving surface 1022 of the object 1023. The removable covering on the right 1021B also includes a lateral section 1026B that is adhered to the receiving surface 1022. Additionally, the removable covering on the right 1021B includes a central tab 1024B that may be adhered to the receiving surface 1022 and covers at least a portion of the central feature 1025.

As shown with respect to the removable covering on the left 1021A, the first free section 1027A, the second free section 1029A, and the lateral section 1026A are connected to form a loop that is further connected to the tab section 1028A.

As shown with respect to the removable covering on the right 1021B, the first free section 1027B, the second free section 1029B, and the lateral section 1026B are connected to form a loop that is further connected to the tab section 1028B. The loop is also connected to central tab 1024B.

The tab sections 1028A and 1028B of the removable coverings 1021A and 1021B are connected to their respective loops at different locations.

Figure 20:
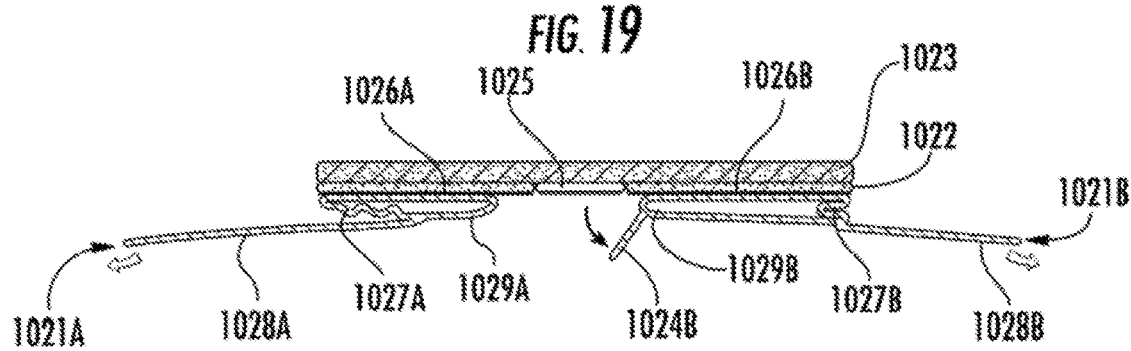
FIG. 20 depicts a side view of the exemplary removable coverings and object of FIG. 19 in a phase of removal.
Figure 21:
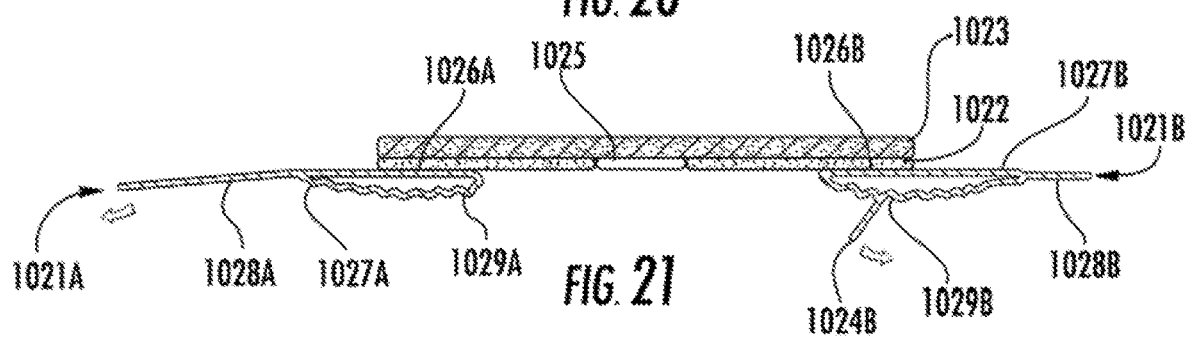
FIG. 21 depicts a side view of the exemplary removable coverings and object of FIG. 19 in a phase of removal.
Figure 22:
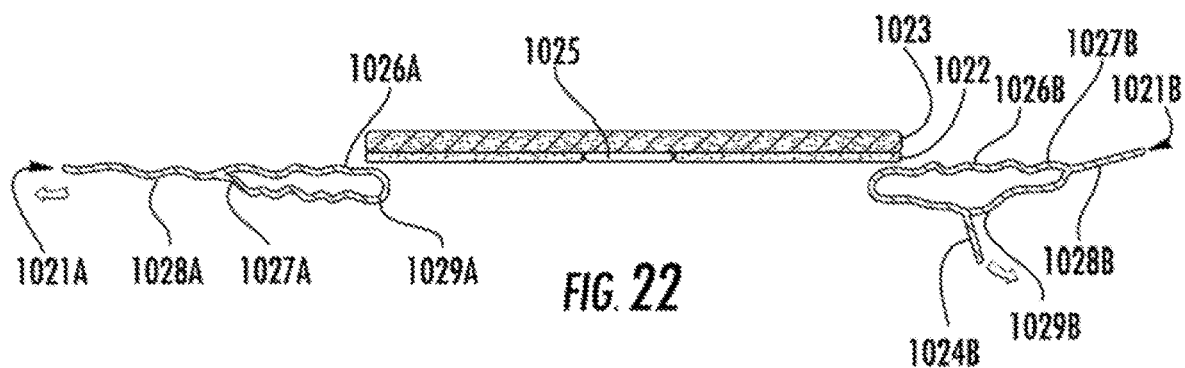
FIG. 22 depicts a side view of the exemplary removable coverings and object of FIG. 19 in a phase of removal.

FIGS. 20-22 depict perspective views of the two exemplary removable coverings 1021A and 102B in different phases of removal. As shown, the connection point of the tab sections 1028A and 1028B of the removable coverings 1021A and 1021B alters the removal process and changes the resistance at each of the phases of removal.

In this regard, exemplary embodiments of the present invention embrace a removable covering wherein the length of the loop may be varied to change the point on the lateral section at which the peel resistance approaches a shearing force at which point a non-adhered central section (e.g., central tab 1024B) becomes a tab for a secondary force vector to provide a peel angle that is between 90 and 180 degrees.

FIG. 23 depicts a side view of an exemplary removable covering 1031 and an object 1033 that includes a receiving surface 1032. Each side (i.e., the left and right sides) of the exemplary removable covering 1031 has the same components. The exemplary removable covering 1031 includes a lateral backing section 1034 and a central backing section 1035. The central backing section 1035 includes a central tab 1035A that is not adhered to the receiving surface 1032 and a first adhered section 1035B that is adhered to the receiving surface 1032.

The lateral backing section 1034 includes a first free section 1036, a second free section 1038, and an attachment section 1039 that are not adhered to the receiving surface 1032. The lateral backing section 1034 also includes a first adhered section 1037 that is adhered to the receiving surface 1032. As shown, the lateral backing section 1034 wraps around the outer edge of the object 1033.

FIG. 24 depicts a side view of the exemplary removable covering 1031 and object 1033 of FIG. 23 within an exemplary packaging system 2000. The packaging system 2000 includes two pieces, a left-side sleeve 2000A and a right-side sleeve 2000B, that may or may not be joined by an adhesive layer 2001. The sleeves 2000A and 2000B each include a top side 2003A and 2003B and a bottom side 2002A and 2002B, respectively.

The exemplary removable covering 1031 and packaging system 2000 function together to facilitate placement of the object 1033 and its receiving surface 1032. In this regard, each lateral backing section's attachment section 1039 (i.e., on the left and right portions of the removable covering 1031) is typically adhered to each respective top side 2003A or 2003B of the packaging system 2000. Additionally, each central backing section's central tab 1035A (i.e., on the left and right portions of the removable covering 1031) is typically adhered to each respective bottom side 2002A or 2002B of the packaging system 2000.

FIGS. 25 and 26 depict side views of the exemplary removable covering 1031, object 1033, and packaging system 2000 of FIG. 24 in different phases of removal. As shown in FIG. 25, when a user pulls the left and right side sleeves 2000A and 2000B away from each other the removable covering 1031 is removed as well. Initially, there is a 180 degree peel strength resistance as the central backing section's first adhered section 1035B is removed from the receiving surface 1032. At some point during the removal process, the lateral backing section 1034 will become fully extended (See FIG. 26) and there will be a shear peel strength resistance. To complete the removal process, the lateral backing section's first free section 1036 may be engaged by a force that overcomes a 180 degree peel strength resistance.

Figure 27:
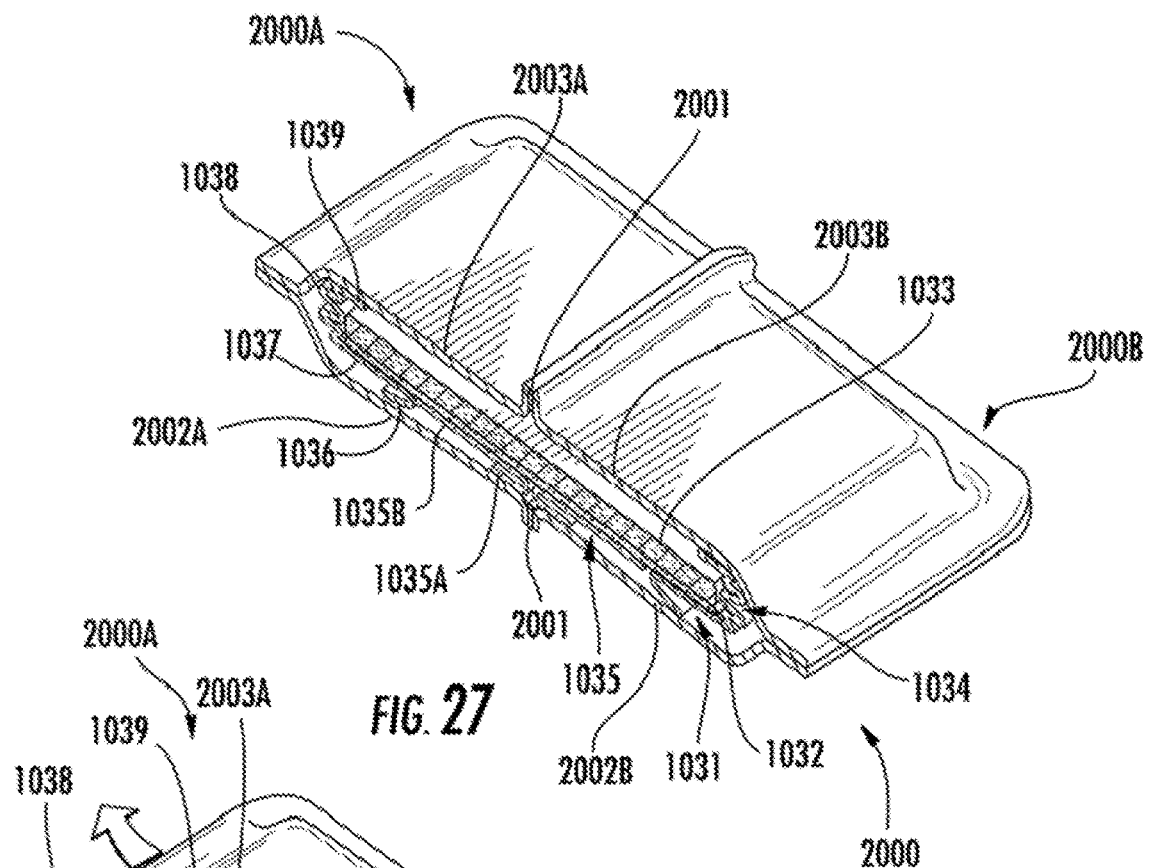
FIG. 27 depicts a perspective view of an exemplary packaging system, removable covering, and object.
Figure 28:
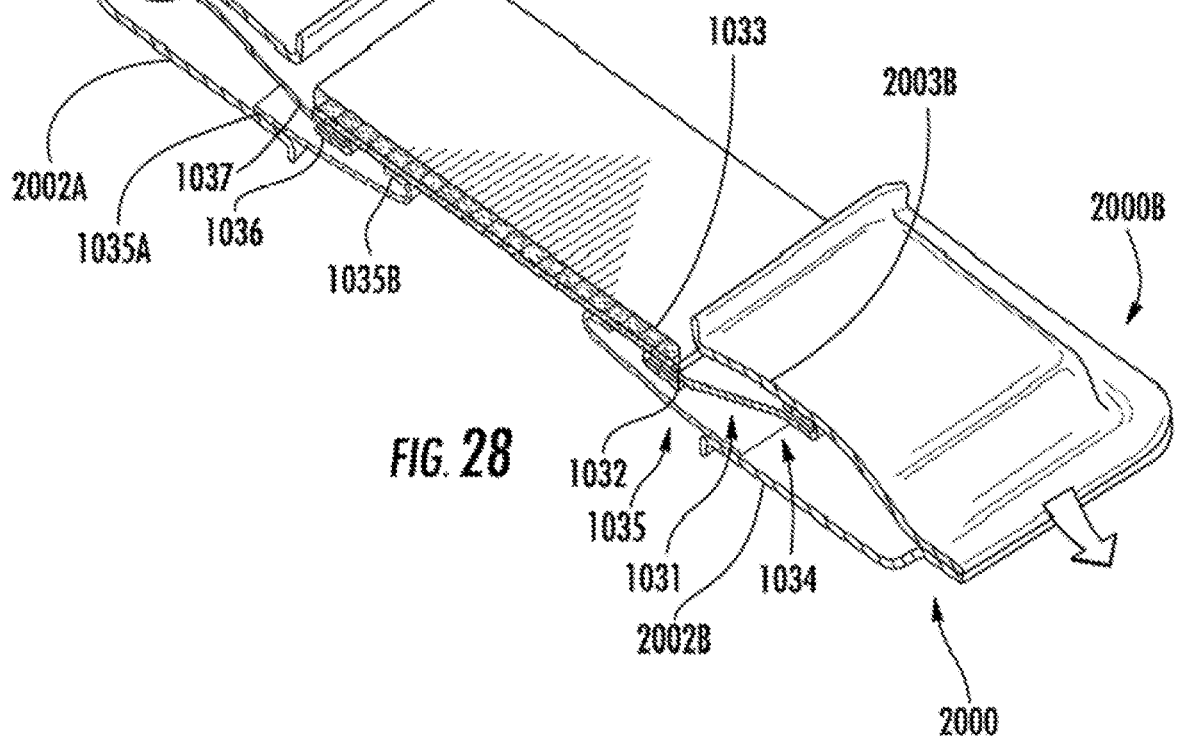
FIG. 28 depicts a perspective view of an exemplary packaging system, removable covering, and object in a phase of removal.

FIG. 27 depicts a perspective view of the exemplary removable covering 1031, object 1033, and packaging system 2000 of FIG. 24. FIG. 28 depicts a perspective view of the exemplary removable covering 1031, object 1033, and packaging system 2000 in the same phase of removal as shown in FIG. 26.

FIG. 29 depicts a side view of an exemplary removable covering 1031 and object 1033 within an exemplary packaging system 2000. The primary differences between the exemplary removable covering 1031 of FIG. 29 and that of FIGS. 23-26 are the locations of attachment of the exemplary removable covering 1031 to (i) the object 1033 and (ii) the packaging system 2000. In FIG. 29, the lateral backing section's first adhered section 1037 is adhered to the top surface of the object 1033 (e.g., via an adhesive layer) rather than the receiving surface 1032 as in FIGS. 23-26. Additionally, each lateral backing section's attachment section 1039 (i.e., on the left and right portions of the removable covering 1031) is adhered to each respective top side 2003A or 2003B at a location that is closer to the central portion of the packaging system 2000 than in FIGS. 23-26.

FIGS. 30-31 depict side views of the exemplary removable covering 1031, object 1033, and exemplary packaging system 2000 of FIG. 29 in different phases of removal. As shown in FIG. 30, when a user pulls the left and right side sleeves 2000A and 2000B away from each other the removable covering 1031 is removed as well. Initially, there is a 180 degree peel strength resistance as the central backing section's first adhered section 1035B is removed from the receiving surface 1032. At some point during the removal process, the lateral backing section 1034 will become fully extended (See FIG. 31) and there will be a shear peel strength resistance. To complete the removal process, the lateral backing section's first free section 1036 may be engaged by a force that overcomes a 180 degree peel strength resistance. As compared to FIGS. 23-26, however, the exemplary embodiment shown in FIGS. 29-31 includes a first free section 1036 that may be engaged while the receiving surface 1032 has been placed because the first free section 1036 is on top of the object 1033.

In this regard, exemplary embodiments of the present invention embrace a removable covering that provides a change in resistance to covering removal along a force vector by means of separate, noncontiguous sections of the removable covering applied to different zones of a primary or secondary receiving surface. By separating the packaging, the user peels a central section at a peel angle that is between 90 and 180 degrees. A lateral section applied to either a primary or secondary receiving surface is subject to a shear force that creates an increased peel resistance compared to the central section. The lateral section may be removed via a secondary tab (e.g., a first free section) which is non-adhered to the primary or secondary receiving surface.

The exemplary removable coverings depicted in and described with respect to FIGS. 23-31 employ free sections, adhered sections, and tabs but may also include loops as depicted in and described with respect to FIGS. 11-22.

Figure 32:
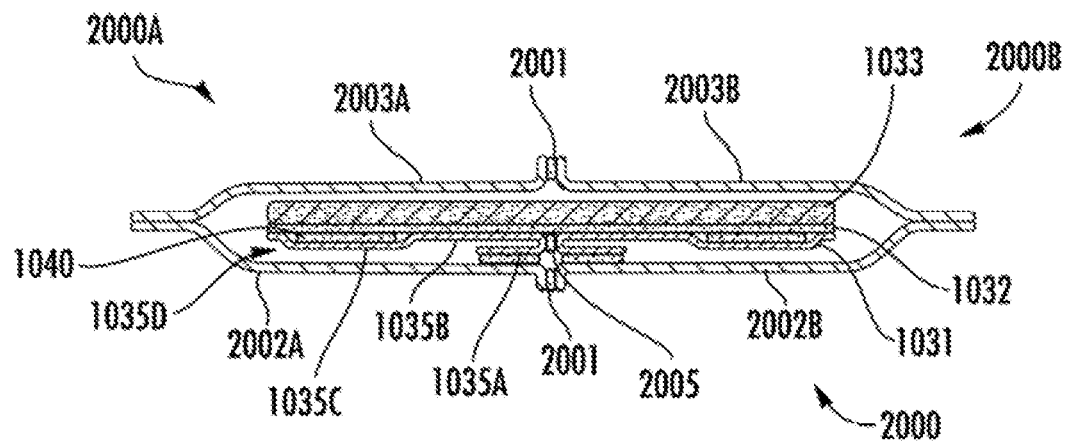
FIG. 32 depicts a side view of an exemplary packaging system, removable covering, and object.

Furthermore, all of the exemplary removable coverings may include zones of altered adhesive strength. For example, FIG. 32 depicts a side view of an exemplary removable covering 1031 and object 1033 within an exemplary packaging system 2000. The exemplary removable covering 1031 and packaging system 2000 of FIG. 32 are similar to those of FIGS. 29-31, but the removable covering 1031 does not include a lateral backing section. Additionally, the exemplary removable covering a includes a central tab 1035A that is not adhered to the receiving surface 1032 and a first adhered section 1035B that is adhered to the receiving surface 1032, but also includes a second adhered section 1035C and a third adhered section 1035D. The second adhered section 1035C is adhered to an extra adhesive layer 1040 that is adhered to the receiving surface 1032. The third adhered section 1035D is adhered to the receiving surface 1032. The second adhered section 1035C and extra adhesive layer 1040 increase the peel strength resistance during removal. The third adhered section 1035D provides a reduction in peel strength resistance at the last phase of removal.

The extra adhesive layer 1040 may be part of the removable covering 1031 or the receiving surface 1032. Alternatively, rather than having an extra adhesive layer 1040 at the shown position, a different strength adhesive could be used at the shown position to increase or decrease peel strength resistance.

As shown in FIG. 32, a central adhesive layer 2005 may adhere the left and right sides of the removable covering 1031 to each other. The central adhesive layer 2005 may provide increased protection against contamination of or damage to the receiving surface 1032 (e.g., an adhesive layer).

Figure 33:
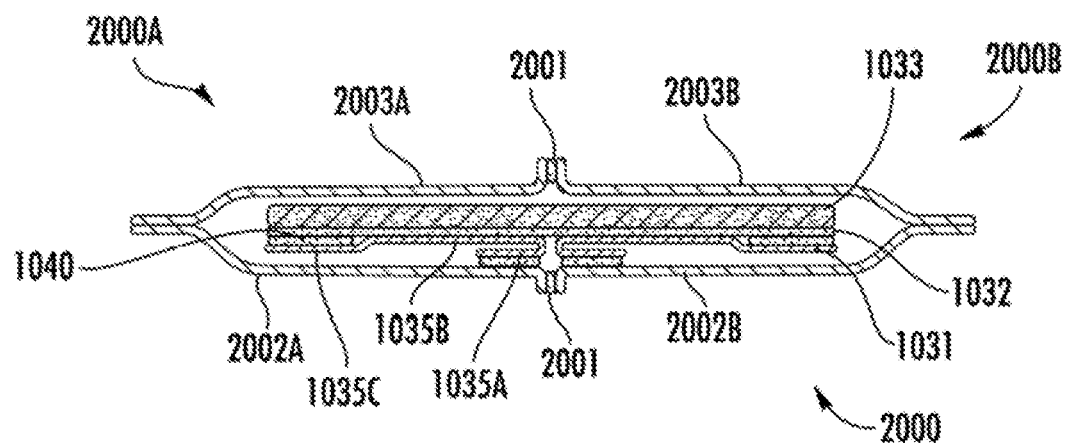
FIG. 33 depicts a side view of an exemplary packaging system, removable covering, and object.

FIG. 33 depicts a side view of an exemplary removable covering 1031 and object 1033 within an exemplary packaging system 2000. The exemplary removable covering 1031 of FIG. 33 is similar to that of FIG. 32, but the removable covering 1031 does not include a third adhered section 1035D at the outer edge of the receiving surface. In this regard, the second adhered section 1035C and extra adhesive layer 1040 increase the peel strength resistance during removal during the last phase of removal.

In this regard, exemplary embodiments of the present invention embrace a removable covering that provides a change in resistance to covering removal along a force vector by means of a change in adhesive strength between the removable covering and the receiving surface to which it is attached. The adhesive strength may be adjusted in zones of varied adhesive strength.

Figure 34:
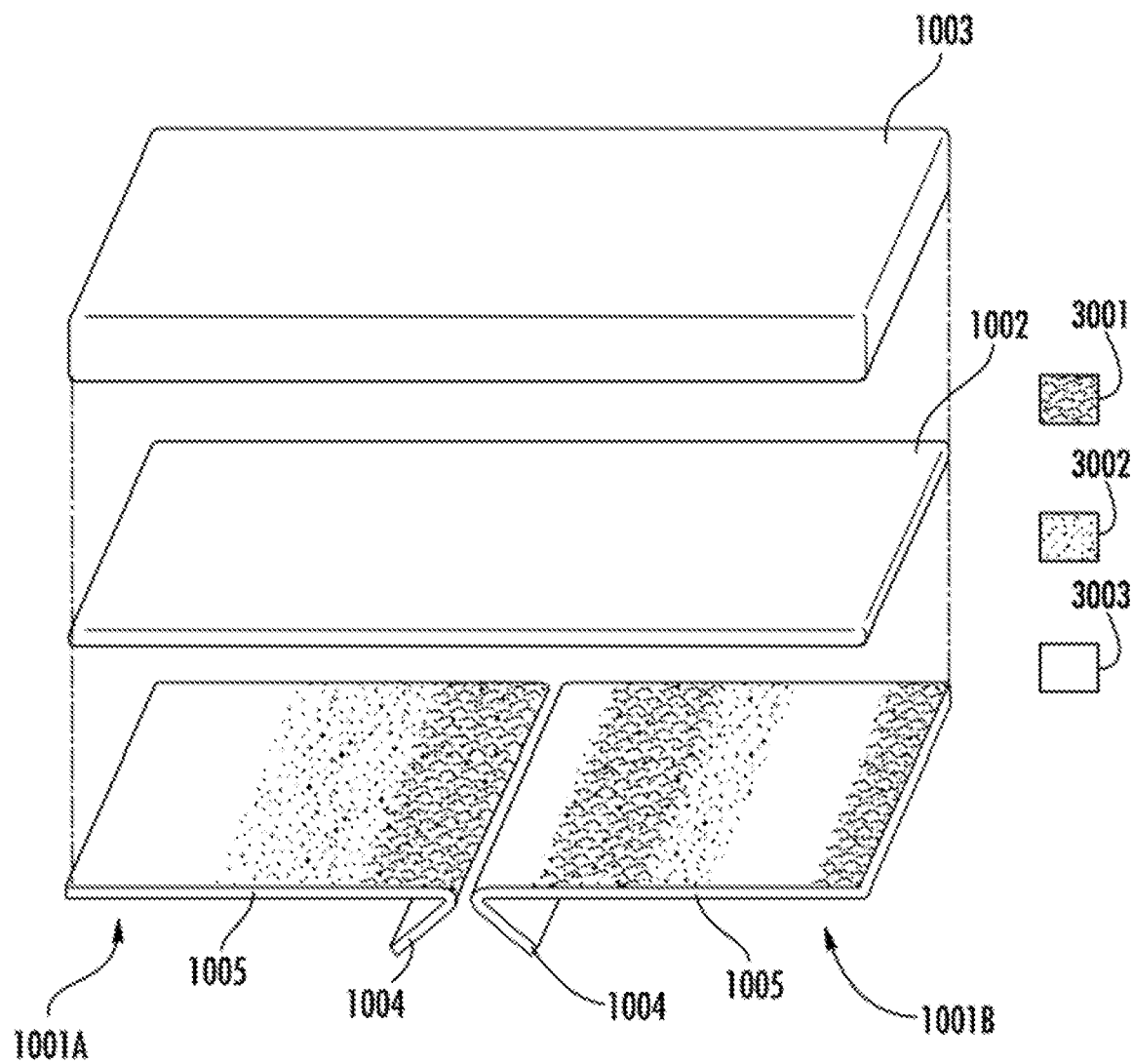
FIG. 34 depicts a perspective view of an exemplary object, adhesive layer, and removable covering.

FIG. 34 depicts a perspective view of an exemplary object 1003, adhesive layer 1002, and two exemplary removable coverings 1001A and 1001B. The exemplary removable coverings 1001A and 1001B each include a primary tab 1004 (e.g., a central terminus or free section) and a central section 1005.

Legend 3001 shows a pattern identifying an area of low peel strength resistance. Legend 3002 shows a pattern identifying an area of medium peel strength resistance. Legend 3003 shows a pattern identifying an area of high peel strength resistance. These peel strength resistances may be achieved by varying the texture or surface of the central section's side that faces the adhesive layer 1002.

Accordingly, as the removable covering 1001A is removed by pulling the primary tab 1004, initially there is a low peel strength resistance, followed by a medium peel strength resistance, and finally a high peel strength resistance. In other words, it requires an increasingly greater force to remove the removable covering 1001A during the removal process.

As the removable covering 1001B is removed by pulling the primary tab 1004, initially there is a high peel strength resistance, followed by a low peel strength resistance, then a medium peel strength resistance, then a high peel strength resistance, and finally a low peel strength resistance.

In this regard, exemplary embodiments of the present invention embrace a covering that provides a change in resistance to covering removal along a force vector by means of a change the surface texture characteristics of the removable covering along zones at which it is attached to the receiving surface. Typically, zones of more coarse texture are less adherent, and smoother zones are more adherent.

Figure 35:
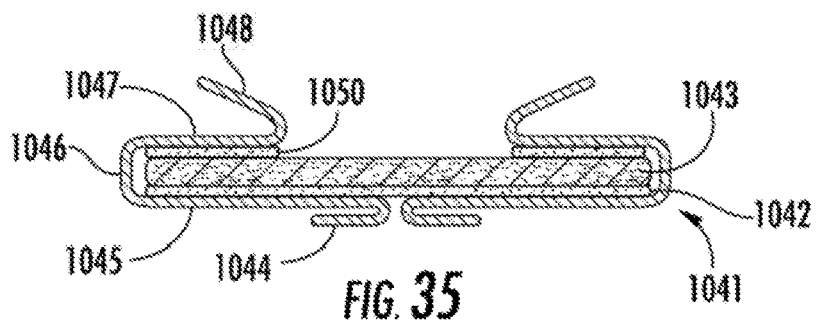
FIG. 35 depicts a side view of an exemplary removable covering and object.

FIG. 35 depicts an exemplary removable covering 1041 and object 1043 that includes a receiving surface 1042 (e.g., an adhesive layer). The removable covering 1041 includes a primary tab 1044 (e.g., a central terminus or free section), a first free section 1046, and a second free section 1048 (e.g., a secondary tab) that are not adhered to the receiving surface 1042 or the object 1043. The removable covering 1041 also includes a first adhered section 1045 (e.g., a lateral section) that is adhered to the receiving surface 1042 and a second adhered section 1047 that is adhered to the top surface of the object 1043 (e.g., via an adhesive layer 1050.

Figure 36:
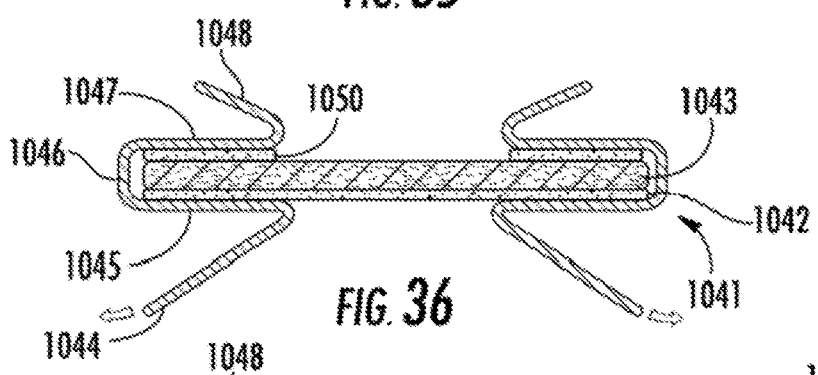
FIG. 36 depicts a side view of the exemplary removable covering and object of FIG. 35 in a phase of removal.
Figure 37:
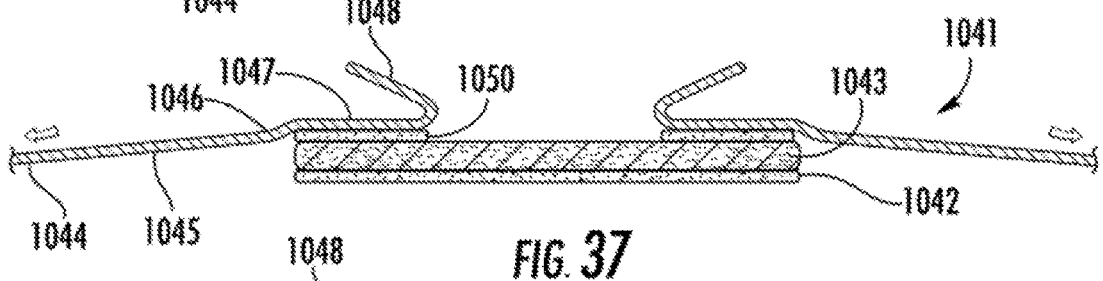
FIG. 37 depicts a side view of the exemplary removable covering and object of FIG. 35 in a phase of removal.
Figure 38:
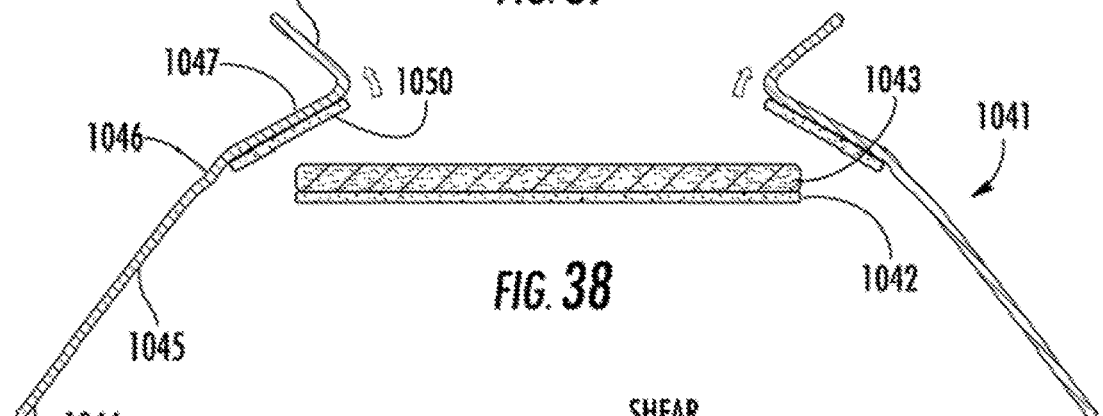
FIG. 38 depicts a side view of the exemplary removable covering and object of FIG. 35 in a phase of removal.
Figure 39:
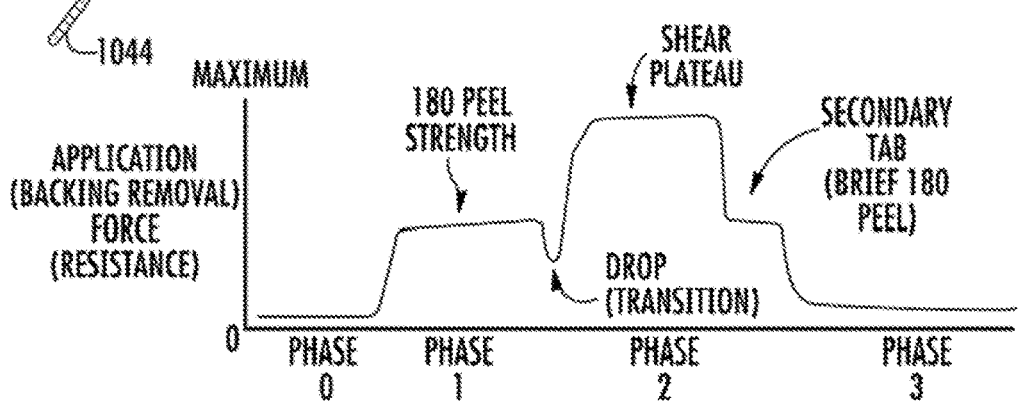
FIG. 39 graphically depicts the application force or resistance necessary to remove the exemplary removable covering of FIG. 35 from the object as a function of time.

FIGS. 36-38 depict side views of the exemplary removable covering 1041 and object 1043 in different phases of removal, while FIG. 39 graphically depicts the application force or resistance necessary to remove the exemplary removable covering 1041 from the object 1043 as a function of time. In FIG. 39, "Phase 0" corresponds to FIG. 35; "Phase 1" corresponds to FIG. 36; "Phase 2" corresponds to FIG. 37; and "Phase 3" corresponds to FIG. 38.

In this regard, exemplary embodiments of the present invention embrace a removable covering that provides a change in resistance to covering removal along a force vector by means of an extension that interfaces with more than one surface of the attached receiving surface. A central section includes a tab that is non-adhered and is available for peeling the central section at a peel angle between 90 and 180 degrees. A lateral section is contiguous with the central section and is adhered to a secondary receiving surface exhibiting a shear resistance to the same force vector that peeled the central section. The lateral section may exhibit a secondary tab that is non-adhered to the secondary receiving surface such that the lateral section peels at an angle between 90 and 180 degrees.

Figure 40:
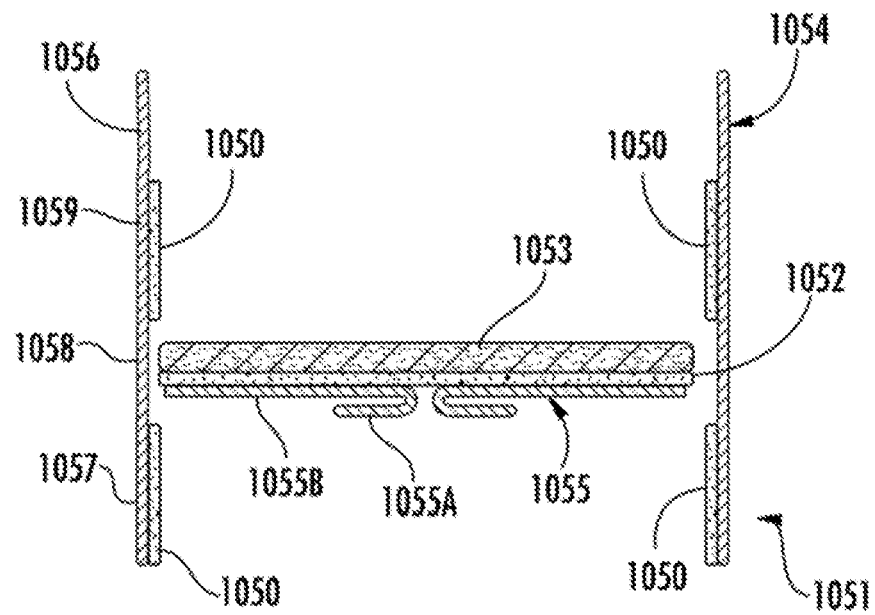
FIG. 40 depicts a side view of an exemplary removable covering and object.
Figure 41:
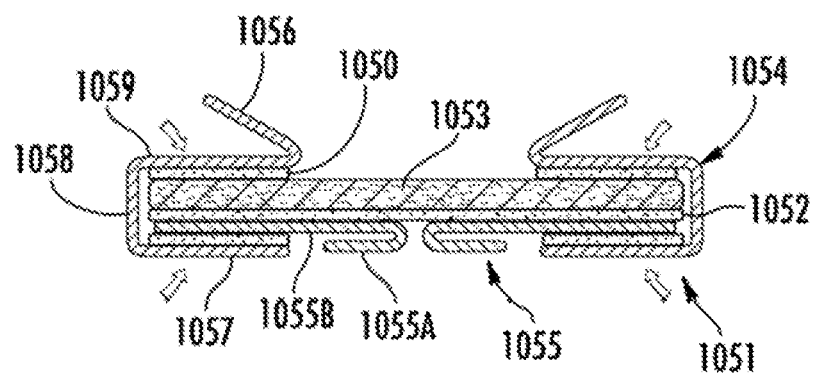
FIG. 41 depicts a side view of the exemplary removable covering of FIG. 40 positioned on the object.

FIG. 40 depicts a side view of an exemplary removable covering 1051 and object 1053, and FIG. 41 depicts a side view of the exemplary removable covering 1051 of FIG. 40 positioned on the object 1053. The object 1053 includes a receiving surface 1052 (e.g., an adhesive layer). Each side (i.e., the left and right sides) of the exemplary removable covering 1051 has the same components. The removable covering 1051 includes a lateral backing section 1054 and a central backing section 1055. The central backing section 1055 includes a central tab 1055A that is not adhered to the receiving surface 1052 and a first adhered section 1055B that is adhered to the receiving surface 1052.

The lateral backing section 1054 includes a first free section 1056 (e.g., a secondary tab) and a second free section 1058 that are not adhered to the receiving surface 1052. The lateral backing section 1054 also includes a first adhered section 1057 that is adhered to the central backing section's first adhered section 1055B (e.g., via an adhesive layer 1050) and a second adhered section 1059 that is adhered to the top surface of the object 1053 (e.g., via an adhesive layer 1050). As shown, the lateral backing section 1054 wraps around the outer edge of the object 1053.

Figure 42:
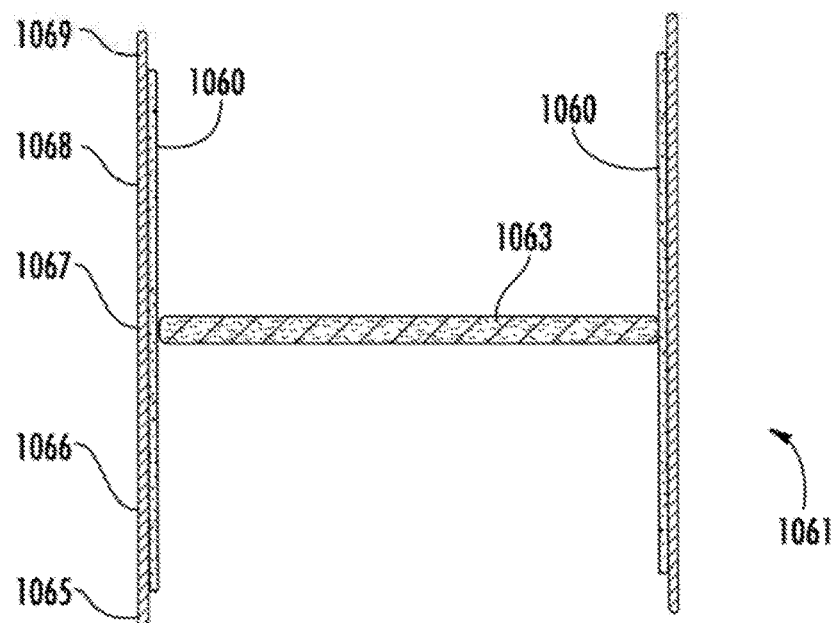
FIG. 42 depicts a side view of an exemplary removable covering and object.
Figure 43:
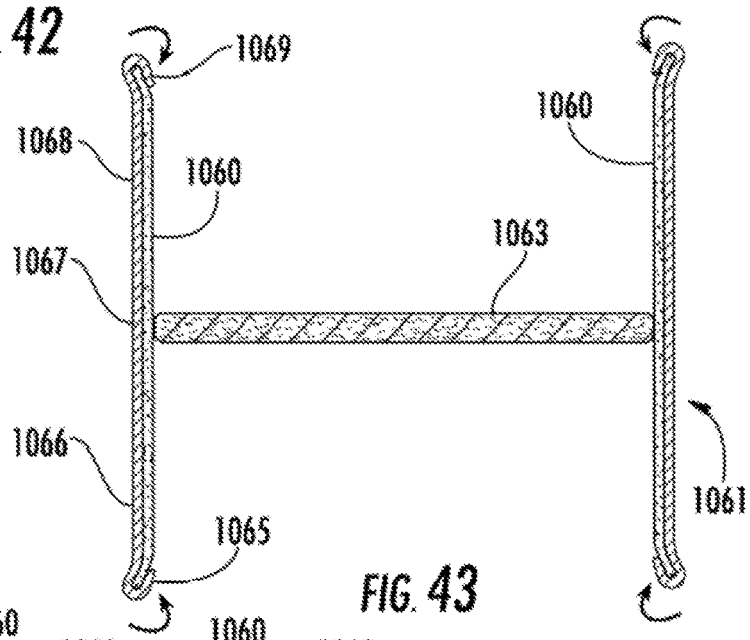
FIG. 43 depicts a side view of the exemplary removable covering and object of FIG. 42 in a phase of application.
Figure 44:
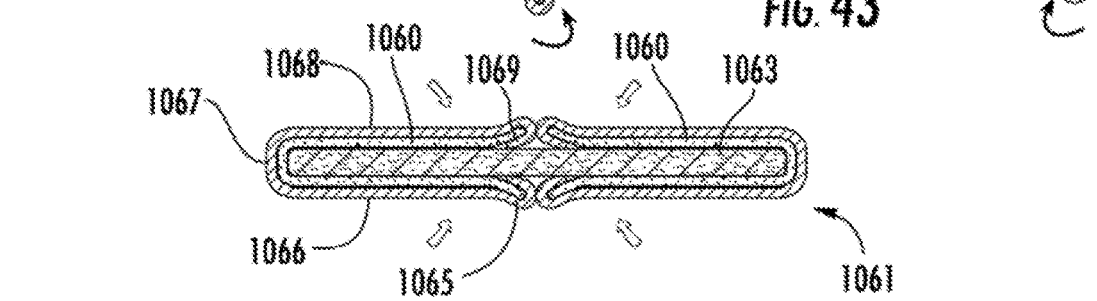
FIG. 44 depicts a side view of the exemplary removable covering and object of FIG. 42 in a phase of application.

FIG. 42 depicts a side view of an exemplary removable covering 1061 and object 1063. Each side (i.e., the left and right sides) of the exemplary removable covering 1061 has the same components. The exemplary removable covering 1061 includes an adhesive layer 1060. The exemplary removable covering 1061 also includes a first adhered section 1066, a second adhered section 1067, and a third adhered section 1068 that adhere to the object 1063 via adhesive layer 1060. See FIG. 44. Additionally, the exemplary removable covering 1061 includes a first free section 1065 and a second free section 1069. As shown in FIG. 43, the first free section 1065 and second free section 1069 may be folded or wrapped onto adhesive layer 1060 to create tabs. By folding the first free section 1065 and second free section 1069 onto adhesive layer 1060, when the exemplary removable covering 1061 is applied to the object 1063, the first free section 1065 and second free section 1069 are not adhered to the object 1063. See FIG. 44. As shown in FIG. 44 the removable covering 1061 may protect the object 1063 until it needs to be placed on a surface.

Figure 45:
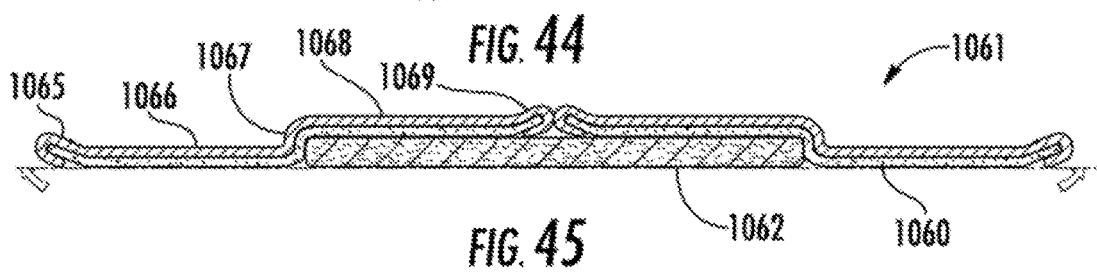
FIG. 45 depicts a side view of the exemplary removable covering and object of FIG. 42 as applied to a surface.

For example, FIG. 45 depicts a side view of the exemplary removable covering 1061 and object 1063 of FIGS. 42-44 as applied to a surface 1062. Starting with the configuration shown in FIG. 44, the first free section 1065 of the left and right sides of the removable covering 1061 may be grasped and pulled to remove the first adhered section 1066 from the bottom surface of the object 1063. The bottom surface of the object 1063 may then be placed on the surface 1062. To hold down or secure the object 1063 to the surface 1062 (e.g., to allow an adhesive, such as glue or cement, to dry or harden), the first adhered section 1066 may be adhered to the portion of the surface 1062 adjacent to the object 1063 (e.g., via adhesive layer 1060).

In exemplary embodiments, the removable covering 1061 may include markings (e.g., grid lines, guidelines, and/or alignment markings) that facilitate application or placement of the object 1603 on the surface 1062. The markings may be printed on the outer surface of the removable covering 1061 (i.e., the surface that does not face the object 1063). Although described with respect to the exemplary embodiment of FIG. 45, such markings may be included on any of the exemplary removable coverings and/or objects disclosed herein. Typically, the markings are printed on a surface of the removable covering that is visible from above the removable covering during the removal process. In this regard, the markings may facilitate a user's alignment of the removable covering and/or object on a surface during the removal process by providing visual guidance.

Thus, exemplary embodiments of the present invention embrace a removable covering that includes a lateral section and a central section that may be made of one or more than one components. As shown, when the central section of the removable covering (over the primary receiving surface) includes a respective adhesive layer, that same adhesive layer (removed with a 90 to 180 degree peel) may be re-adhered to a third receiving surface.

Figure 46:
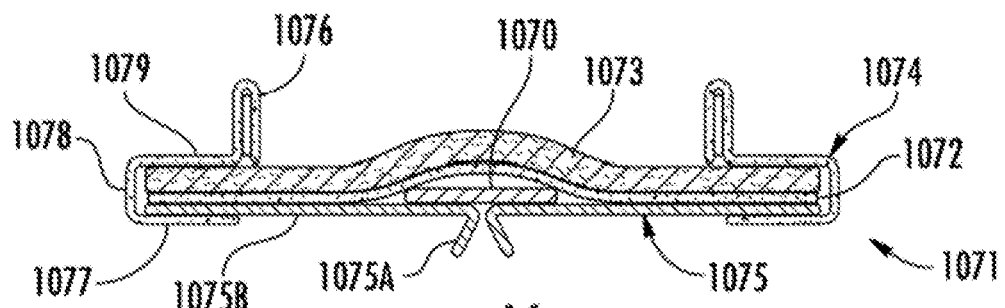
FIG. 46 depicts a side view of an exemplary removable covering and object.

FIG. 46 depicts a side view of an exemplary removable covering 1071 and object 1073 that includes a receiving surface 1072 (e.g., an adhesive layer) and a central pad 1070. Each side (i.e., the left and right sides) of the exemplary removable covering 1071 has the same components. The removable covering 1071 includes a lateral backing section 1074 and a central backing section 1075. The central backing section 1075 includes a central tab 1075A that is not adhered to the receiving surface 1072 and a first adhered section 1075B that is adhered to the receiving surface 1072. The lateral backing section 1074 includes a first free section 1076 (e.g., a secondary tab) and a second free section 1078 that are not adhered to the receiving surface 1072. The depicted first free section 1076 is formed of a section folded on itself and joined by an adhesive layer. The lateral backing section 1074 also includes a first adhered section 1077 that is adhered to the central backing section's first adhered section 1075B (e.g., via an adhesive layer) and a second adhered section 1079 that is adhered to the top surface of the object 1073 (e.g., via an adhesive layer). As shown, the lateral backing section 1074 wraps around the outer edge of the object 1073.

Figure 47:
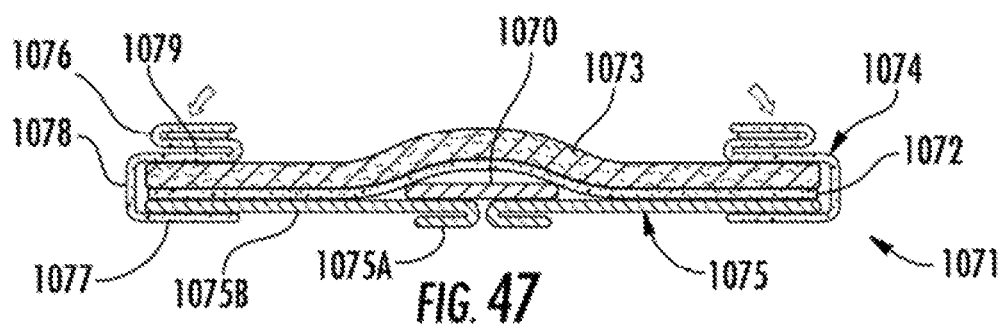
FIG. 47 depicts a side view of the exemplary removable covering and object of FIG. 46 in a phase of folding.

FIG. 47 depicts a side view of the exemplary removable covering 1071 and object 1073 of FIG. 46 in a phase of folding. In particular, the first free section 1076 (e.g., a secondary tab) has been folded onto the top surface of the second adhered section 1079. Additionally, the left and right central tab 1075A has been folded onto the bottom or outer surface of the first adhered section 1075B.

Figure 48:
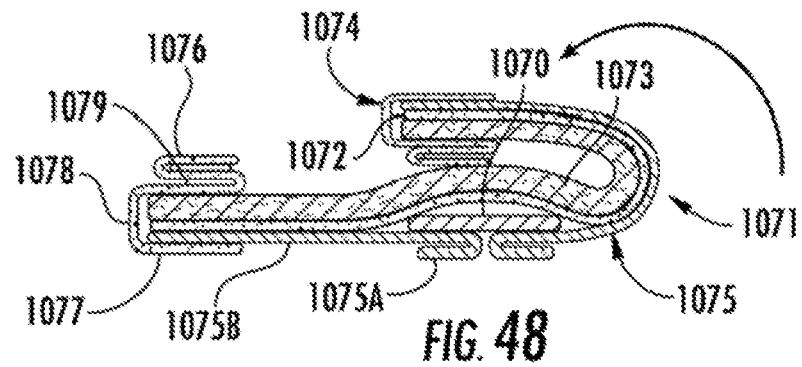
FIG. 48 depicts a side view of the exemplary removable covering and object of FIG. 46 in a phase of folding.

FIG. 48 depicts a side view of the exemplary removable covering 1071 and object 1073 of FIG. 46 in a further phase of folding. In particular, the right side of the removable covering 1071 and object 1073 have been folded upward around a folding axis located approximately at the right edge of the pad 1070 such that the first free section 1076 is over the central portion of the object 1073.

Figure 49:
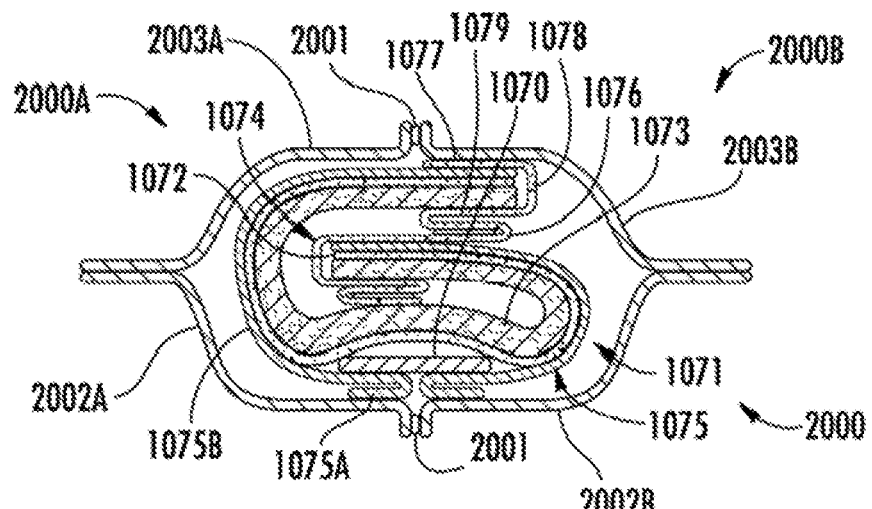
FIG. 49 depicts a side view of the exemplary removable covering and object of FIG. 46 as folded and within an exemplary packaging system.

FIG. 49 depicts a side view of the exemplary removable covering 1071 and object 1073 of FIG. 46 in a further phase of folding and within an exemplary packaging system 2000. In particular, the left side of the removable covering 1071 and object 1073 have been folded upward around a folding axis located approximately at the left edge of the pad 1070 such that the first free section 1076 is over (i) the right side of the removable covering 1071 and (ii) the central portion of the object 1073. In other exemplary embodiments, the left side of the removable covering 1071 and object 1073 may be folded before the right side of the removable covering 1071 and object 1073. The folded removable covering 1071 and object 1073 are within the packaging system 2000.

The packaging system 2000 includes two pieces, a left-side sleeve 2000A and a right-side sleeve 2000B, that may or may not be joined by an adhesive layer 2001. The sleeves 2000A and 2000B each include a top side 2003A and 2003B and a bottom side 2002A and 2002B, respectively.

The exemplary removable covering 1071 and packaging system 2000 function together to facilitate placement of the object 1073 and its receiving surface 1072. In this regard, each central backing section's central tab 1075A (i.e., on the left and right portions of the removable covering 1071) is typically adhered to each respective bottom side 2002A or 2002B of the packaging system 2000. When a user pulls the left and right side sleeves 2000A and 2000B away from each other the removable covering's central backing section 1075 is at least partially removed as well. Additionally, natural spring tension unfolds the left and right sides of the removable covering 1071 and object 1073 as the top sides 2003A and 2003B move apart. After the object 1073 and is receiving surface 1072 are placed, the first free section 1076 of each side may be engaged to remove the lateral backing section 1074 and the removable covering 1071.

In this regard, exemplary embodiments of the present invention embrace a removable covering that provides a change in resistance to removal along a force vector by a variety of mechanisms may be attached to a receiving surface along a flexible object and surrounded by a connected packaging. The flexible object and the removable covering may be folded for smaller package dimensions and materials. Removal of the integrated packaging simultaneously unfolds the flexible object and removes the covering by peeling as noted above. Any mechanism that increases the peel resistance is available for integration into this embodiment.

Figure 50:
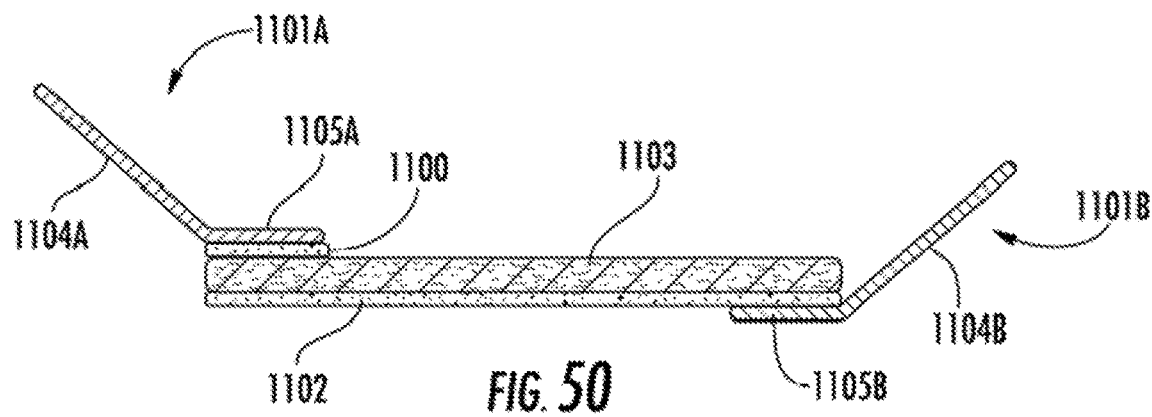
FIG. 50 depicts a side view of two exemplary removable coverings and an object.

FIG. 50 depicts a side view of two exemplary removable coverings 1101A and 1101B and an object 1103 having a receiving surface 1102 (e.g., an adhesive layer). As shown, exemplary removable coverings in accordance with the present invention may adhere to the top of an object 1103 (e.g., via an adhesive layer 1000) as does the exemplary removable covering 1101A on the left or to the bottom of an object 1103 (e.g., when the receiving surface 1102 is an adhesive layer or via an adhesive layer) as does the exemplary removable covering 1101B on the right. As shown, the exemplary removable coverings 1101A and 1101B each include a first free section 1104A and 1104B, respectively, that are not adhered to the object 1103 or receiving surface 1102. The exemplary removable coverings 1101A and 1101B also each include a first adhered section 1105A and 1105B, respectively, which are adhered to the object 1103 and the receiving surface 1102, respectively. By altering the adhesion location (i.e., top or bottom of the object) in relation to the relative elastic quality of the removable covering or the relative elasticity of the object, the release mechanism of the removable covering may be controlled.

Figure 51:
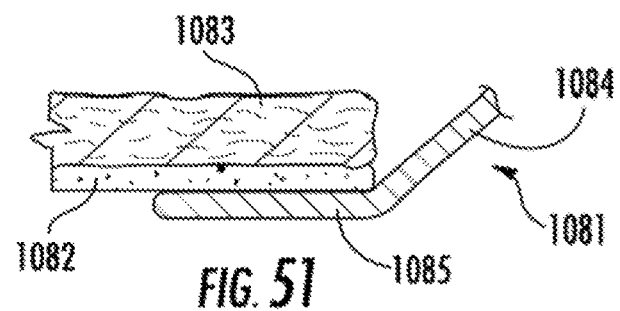
FIG. 51 depicts a side view of the exemplary removable covering and object depicted on the left side of FIG. 50.
Figure 52:
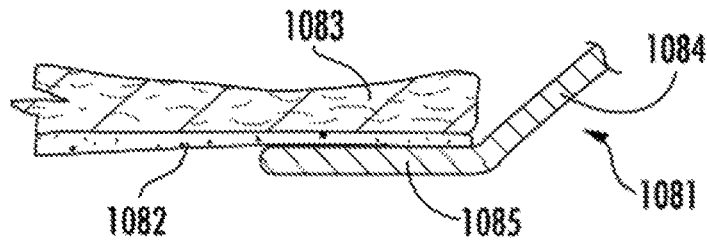
FIG. 52 depicts a side view of the exemplary removable covering and object depicted on the left side of FIG. 50 in a phase of removal.

For example, FIGS. 51 and 52 depict an exemplary removable covering 1081 that is less elastic (i.e., less flexible, less expandable, and/or more rigid) than the object 1083 and its adhesive layer 1082. The exemplary removable covering 1081 includes a first free section 1084 that is not adhered to the object 1083 and a first adhered section 1085 that is adhered to the bottom surface (i.e., receiving surface 1102) of the object 1083.

In FIG. 52, a tension is applied to the first free section 1084. Because the object 1083 and its adhesive layer 1082 are more elastic (i.e., more flexible, more expandable, and/or less rigid) than the removable covering 1081, they deform. The combination of this deformation and the difference in elasticity causes the free end of the first adhered section 1085 (i.e., the end opposite the connection to the first free section 1084 or the left end as depicted) to release from the adhesive layer 1082 before the rest of the first adhered section 1085. In other words, the shear pull strength resistance from the adhesive layer 1082 is first overcome at the portion of the removable covering 1081 that is furthest from the location at which the removal force is applied (i.e., at the free end of the first free section 1084). Typically, the adhesive layer 1082 remains on the object 1083 after removal in this exemplary embodiment.

Figure 53:
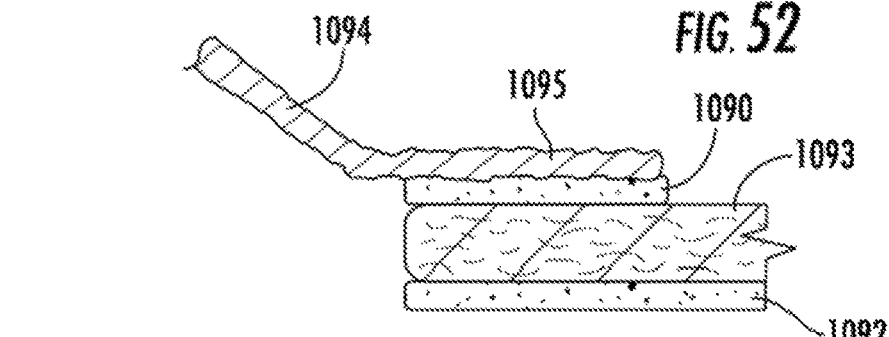
FIG. 53 depicts a side view of the exemplary removable covering and object depicted on the right side of FIG. 50.
Figure 54:
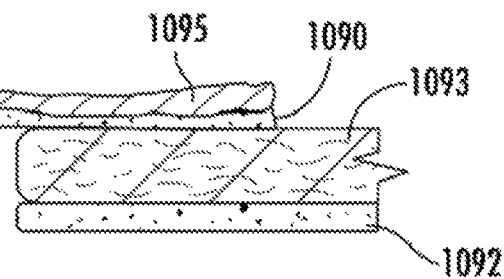
FIG. 54 depicts a side view of the exemplary removable covering and object depicted on the right side of FIG. 50 in a phase of removal.

As another example, FIGS. 53 and 54 depict an exemplary removable covering that is more elastic (i.e., more flexible, more expandable, and/or less rigid) than the object 1093 and the adhesive layer 1090. The exemplary removable covering includes a first free section 1094 that is not adhered to the object 1093 and a first adhered section 1095 that is adhered to the top surface of the object 1083 by adhesive layer 1090.

In FIG. 54, a tension is applied to the first free section 1094. Because the removable covering 1091 is more elastic (i.e., more flexible, more expandable, and/or less rigid) than the object 1093, the removable covering 1091 deforms (e.g., stretches). The combination of this deformation and the difference in elasticity causes the end of the first adhered section 1095 that is connected to the first free section 1094 (i.e., the left end as depicted or the end opposite the free end) to release from the object 1093 before the rest of the first adhered section 1095. In other words, the shear pull strength resistance from the adhesive layer 1090 is first overcome at the portion of the removable covering 1091 that is closest to the location at which the removal force is applied (i.e., at the free end of the first free section 1094). Typically, the adhesive layer 1090 remains on the removable covering 1091 after removal and deforms similarly to the removable covering 1091 in this exemplary embodiment.

In this regard, exemplary embodiments of the present invention embrace a removable covering that provides a change in resistance to covering removal along a force vector by means of different expandability characteristics between the removable covering and the attached receiving surface. Any mechanism that increases the peel resistance is available for integration into this embodiment and may incorporate the expansion feature on the covering or on the object having a receiving surface. If the lateral section of the removable covering (subject to shear force) is more elastic than the receiving surface, then the force vector will cause a progressive shear failure beginning at the lateral terminus of the receiving surface and advancing centrally. If the lateral section of the removable covering (subject to shear force) is less elastic than the receiving surface, then the force vector will cause a progressive shear failure beginning at the central terminus of the receiving surface and advancing laterally.

A removable covering's resistance to removal from an object may be altered by varying the stiffness or flexibility of the removable covering at different locations along an adhered section. For example, FIG. 55 depicts a side view of an exemplary packaging system 2000, removable covering 1111, and object 1113 having a receiving surface 1112 (e.g., an adhesive layer). Each side (i.e., the left and right sides) of the exemplary removable covering 1111 includes a primary tab 1114 (e.g., a central terminus or free section), a lateral stiffening section 1117, and an adhesive layer 1116 that are not adhered to the receiving surface 1112 of the object 1113. The removable covering 1111 also includes a central section 1115 (e.g., an adhered section) that is adhered to the receiving surface 1112. The lateral stiffening section 1117 is adhered to the bottom surface of the central section 1115 via the adhesive layer 1116.

The packaging system 2000 includes two pieces, a left-side sleeve 2000A and a right-side sleeve 2000B, that may or may not be joined by an adhesive layer 2001. The sleeves 2000A and 2000B each include a top side 2003A and 2003B and a bottom side 2002A and 2002B, respectively.

The exemplary removable covering 1111 and packaging system 2000 function together to facilitate placement of the object 1113 and its receiving surface 1112. In this regard, each primary tab 1114 (i.e., on the left and right portions of the removable covering 1111) is typically adhered to each respective bottom side 2002A or 2002B of the packaging system 2000 (e.g., via the adhesive layer 1118 as shown).

FIGS. 56-58 depict side views of the exemplary removable covering 1111, object 1113, and packaging system 2000 of FIG. 55 in different phases of removal. As shown in FIG. 56, when a user pulls the left and right side sleeves 2000A and 2000B away from each other the removable covering 1111 is removed as well. Initially, there is a 180 degree peel strength resistance as the central section 1115 is removed from the receiving surface 1112. After the first portion of the central section 1115 has been removed as shown in FIG. 57, the peel strength resistance increases because of the lateral stiffening section 1117 and adhesive layer 1116. The thicker section (i.e., the lateral stiffening section 1117 and adhesive layer 1116) may increase the peel strength resistance by (i) requiring a peel angle that is closer to a 90 degree peel than to the 180 degree peel in the thinner section and/or (ii) increasing the area of the lateral portion of the central section 1115 that must be peeled away from the receiving surface 1112 at the same time.

A varied peel strength resistance such as this can be achieved using a variety of techniques. For example, rather than stacking sections of removable covering (e.g., as shown on the left half of FIG. 61), the thickness of a portion of the removable covering may be increased or decreased. The variation in thickness may be gradual, stepped, or abrupt to provide a range of smooth to sharp changes in resistance. Furthermore, the location along the receiving surface at which the resistance change occurs may vary. For example, the resistance change may occur due to a thickness change in the middle of the portion of the removable covering that is adhered to the receiving surface (e.g., as shown on the right half of FIG. 61).

In this regard, exemplary embodiments of the present invention embrace a removable covering that provides a change in resistance to covering removal along a force vector by means of a change in flexibility of the removable covering. In phase 1 (e.g., FIG. 56), the central section of the removable covering is peeled away at a 90 to 180 degree peel angle as the package is separated if the lateral edge of the removable covering is more rigid, the peeling angle is momentarily lower and more resistance to peeling is present.

As previously noted with respect to FIG. 34, a varied peel strength resistance can be achieved by varying the texture of the removable covering. Exemplary removable coverings may also achieved varied peel strength resistance by including a varied release coating (e.g., to provide a varied resistance to adhesion). For example, FIG. 59 depicts a perspective view of an exemplary object 1123, adhesive layer 1122, and two exemplary removable coverings 1121A and 1121B. The exemplary removable coverings 1121A and 1121B each include a primary tab 1124 (e.g., a central terminus or free section) and a central section 1125. The shading identifies areas of more or less release coating: darker areas indicate more release coating and lighter areas indicate less release coating.

Accordingly, as the removable covering 1121A is removed by pulling the primary tab 1124, initially there is a low peel strength resistance, followed by a medium peel strength resistance, and finally a high peel strength resistance. In other words, it requires an increasingly greater force to remove the removable covering 1121A during the removal process.

As the removable covering 1121B is removed by pulling the primary tab 1124, initially there is a high peel strength resistance, followed by a low peel strength resistance, then a medium peel strength resistance, then a high peel strength resistance, and finally a low peel strength resistance.

As previously noted, FIG. 61 depicts a side view of a two exemplary removable coverings and an object illustrating configurations capable of achieving varied resistance by stacking layers of backing and changing the location of increased resistance.

The left-side graph of FIG. 60 graphically depicts the force required to remove the left-side removable coverings of FIGS. 59 and 61 as a function of distance from the midpoint of the adhesive layer. The right-side graph of FIG. 60 graphically depicts the force required to remove the right-side removable covering of FIG. 61 as a function of distance from the midpoint of the adhesive layer. The units on the x-axis of both graphs are arbitrary.

Yet another technique for varying a removable covering's resistance to removal employs loops such as those described with respect to FIGS. 11-22. In particular, increasing the length of a given loop will increase resistance to removal by increasing the percentage of the resistance that is a shear peel strength resistance. Conversely, decreasing the length of a given loop will decrease resistance to removal by decreasing the percentage of the resistance that is a shear peel strength resistance.

Still another technique for varying a removable covering's resistance to removal employs folds such as those described with respect to, for example, FIGS. 1-10. In particular, increasing the length of a given fold will increase resistance to removal by increasing the percentage of the resistance that is a shear peel strength resistance. Conversely, decreasing the length of a given fold will decrease resistance to removal by decreasing the percentage of the resistance that is a shear peel strength resistance.

The interaction between a removable covering and a packaging system may also achieve a varied resistance to removal. For example, FIG. 62 depicts an overhead view of an exemplary packaging system. The packaging system has a top surface and a bottom surface that are adhesed to each other at the outer edges as indicated by the textured area. The white space and dotted lines indicate the free inner space between the top and bottom surfaces. As shown, the free space tapers from a width W near the left and right edges to a width t near the midline. The left and right portions (i.e., as separated by the midline) may or may not be adhesed to each other at the midline.

FIG. 63 depicts an overhead view of an exemplary removable covering and/or object. The left and right halves of the removable covering and/or object are different to illustrate the varied resistance that may be achieved.

FIG. 64 graphically depicts the force required to remove the packaging system of FIG. 62 from the removable covering of FIG. 63 for the left and ride sides of the removable covering of FIG. 63 as a function of distance from the midpoint of the packaging system. As shown, the shape of the removable covering and/or object as it interacts with the tapered width of the free space within the packaging system varies the resistance to removal.

In this regard, exemplary embodiments of the present invention embrace a removable covering that provides a change in resistance to covering removal along a force vector by means of varying the texture of the removable covering or the receiving object in gradual or stepped changes. Zones of more coarse texture are less adherent due to reduced adhesive surface area, and, in contrast, smoother zones are more adherent.

FIG. 65 depicts an overhead view of an exemplary removable covering and/or object within an exemplary packaging system. As in FIG. 62, the packaging system has a top surface and a bottom surface that are adhesed to each other at the outer edges as indicated by the textured area. The removable covering and/or object is shown in the free inner space between the top and bottom surfaces. In this depicted embodiment, there is less variation in resistance and the variation is less abrupt than in FIGS. 62-64 because the packaging system and the removable covering and/or object have (i) a reduced width variation and (ii) matched contours (i.e., of the adhesed edges of the packaging system and the width of the removable covering and/or object).

Figure 66:
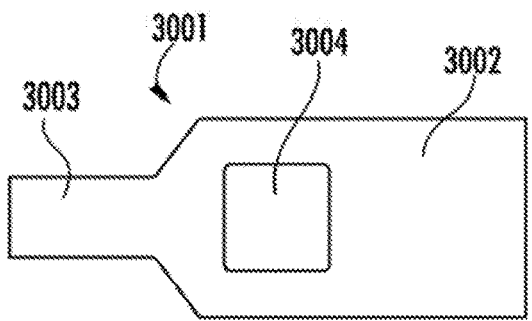
FIG. 66 depicts an overhead view of an exemplary removable covering.
Figure 67:
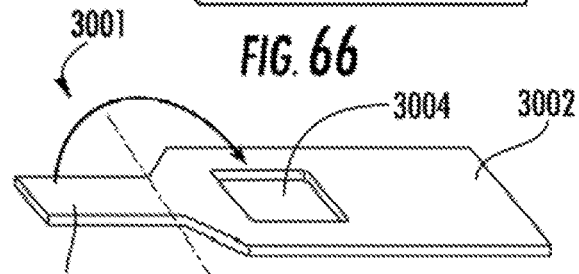
FIG. 67 depicts a perspective view of the exemplary removable covering of FIG. 66.

FIG. 66 depicts an overhead view of an exemplary removable covering 3001 that includes a body section 3002, a secondary pull tab 3003, and an opening 3004 in the body section 3002. FIG. 67 depicts a perspective view of the exemplary removable covering 3001 of FIG. 66 with an initial fold axis.

Figure 68:
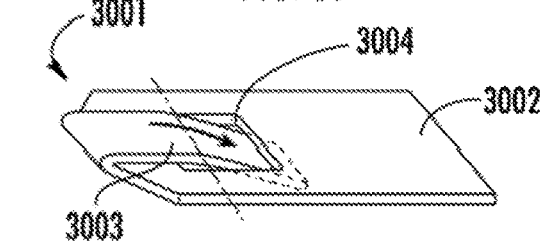
FIG. 68 depicts a perspective view of the exemplary removable covering of FIG. 66 in a phase of manufacturing.

FIG. 68 depicts a perspective view of the exemplary removable covering 3001 after the secondary pull tab 3003 has been folded over the initial fold axis shown in FIG. 67. The end of the secondary pull tab 3003 is passed through the opening 3004 in the body section 3002. FIG. 68 also shows the second fold axis.

Figure 69:
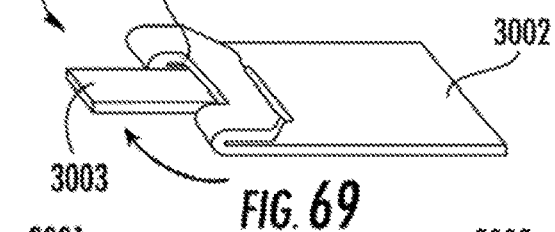
FIG. 69 depicts a perspective view of the exemplary removable covering of FIG. 66 in a phase of manufacturing.

FIG. 69 depicts a perspective view of the exemplary removable covering 3001 after the left portion of the body section 3002, the opening 3004, and the secondary pull tab 3003 have been folded over the second fold axis. As depicted, the secondary pull tab 3003 extends outward to the left of the removable covering 3001.

Figure 70A:
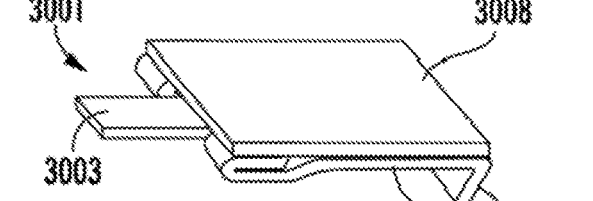
FIG. 70A depicts a perspective view of the exemplary removable covering of FIG. 66 as manufactured in the phases depicted in FIGS. 67-69 and an object.

FIG. 70A depicts a perspective view of the exemplary removable covering 3001 as manufactured in the phases depicted in FIGS. 67-69 and an object 3008. The object 3008 may be adhesed to the removable covering 3001 (e.g., via an adhesive layer). The right portion of the body section 3002 has been folded downward to form a primary pull tab 3005.

Figure 70B:
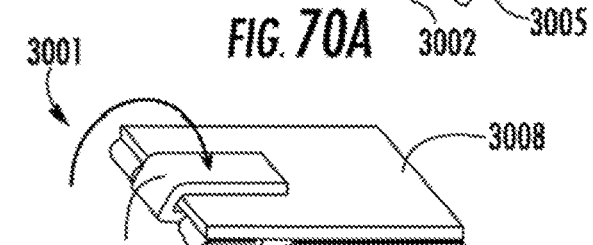
FIG. 70B depicts a perspective view of the exemplary removable covering and object of FIG. 70A in another phase of manufacturing.

FIG. 70B depicts a perspective view of the exemplary removable covering 3001 and object 3008 of FIG. 70A after the secondary pull tab 3003 has been folded around the outer edge of the object 3008. The secondary pull tab 3003 may be adhesed to the object 3008 (e.g., via an adhesive layer) and may include another tab (not shown) that is not adhesed to the object 3008.

Figure 71:
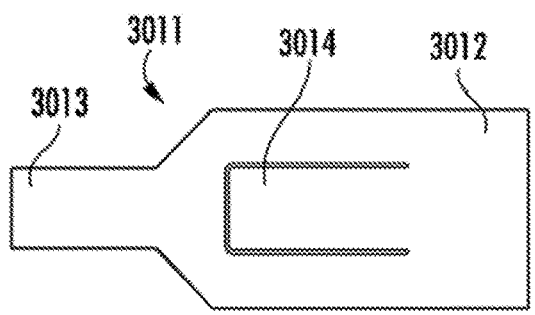
FIG. 71 depicts an overhead view of an exemplary removable covering.
Figure 72:
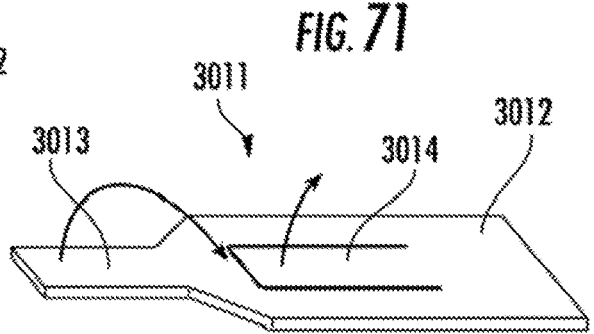
FIG. 72 depicts a perspective view of the exemplary removable covering of FIG. 71.

FIG. 71 depicts an overhead view of an exemplary removable covering 3011 that includes a body section 3012, a secondary pull tab 3013, and a flap section 3014 formed in the body section 3002 by three linear openings. FIG. 72 depicts a perspective view of the exemplary removable covering 3011 of FIG. 71 with two initial fold movements.

Figure 73:
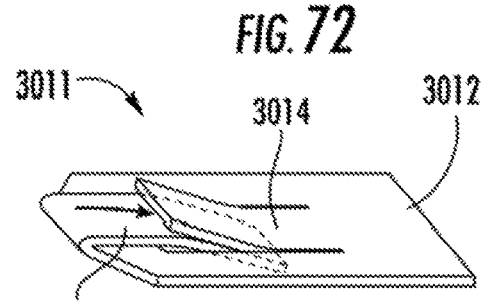
FIG. 73 depicts a perspective view of the exemplary removable covering of FIG. 71 in a phase of manufacturing.
Figure 74:
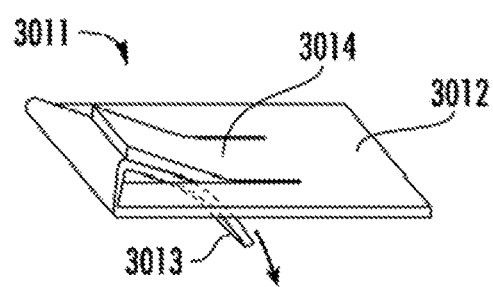
FIG. 74 depicts a perspective view of the exemplary removable covering of FIG. 71 in a phase of manufacturing.

FIG. 73 depicts a perspective view of the removable covering 3011 after the secondary pull tab 3013 has been folded under the flap section 3014. As shown in FIG. 74, the secondary pull tab 3013 is pulled further and the left portion of the body section 3012 is folded under the flap section 3014.

Figure 75:
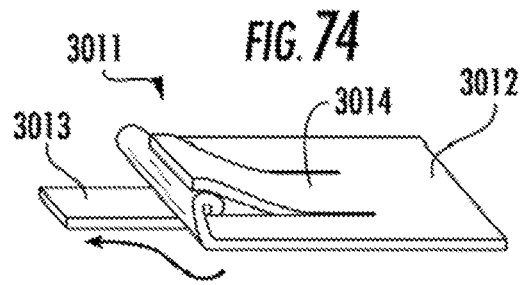
FIG. 75 depicts a perspective view of the exemplary removable covering of FIG. 71 in a phase of manufacturing.

FIG. 75 depicts a perspective view of the removable covering 3011 after the secondary pull tab 3013 has been folded back on itself around the left portion of the body section 3012. As depicted, the secondary pull tab 3003 extends outward to the left of the removable covering 3001. An object may be placed on top of the body section 3012 and flap section 3014, the secondary pull tab may be folded around the outer edge of the object, and/or the right portion of the body section 3012 may be folded downward to form a primary pull tab (not shown).

Figure 76:
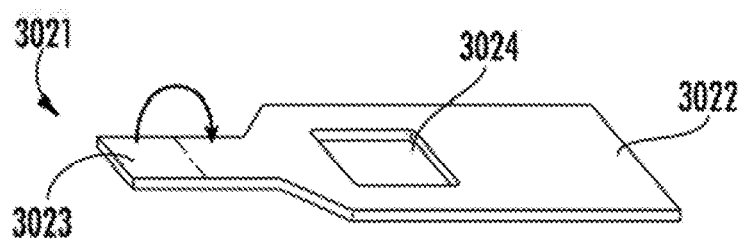
FIG. 76 depicts a perspective view of a portion of an exemplary removable covering.

FIG. 76 depicts a perspective view of the central section 3021 of an exemplary removable covering. The central section 3021 includes an attachment section 3023, a body section 3022, and an opening 3024 in the body section 3022. As shown, the attachment section 3023 is folded over an initial fold axis.

Figure 77:
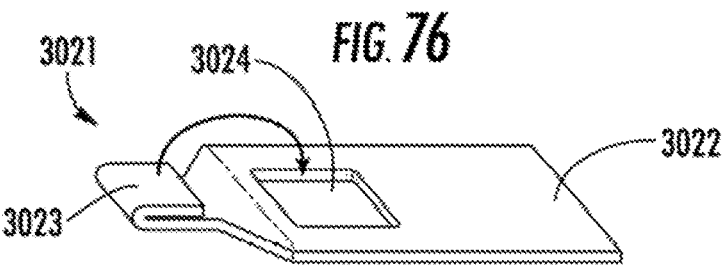
FIG. 77 depicts a perspective view of the exemplary removable covering of FIG. 76 in a phase of manufacturing.

FIG. 77 depicts a perspective view of the central section 3021 after the attachment section 3023 has been folded over the initial fold axis shown in FIG. 76. FIG. 77 also shows the second fold axis.

Figure 78:
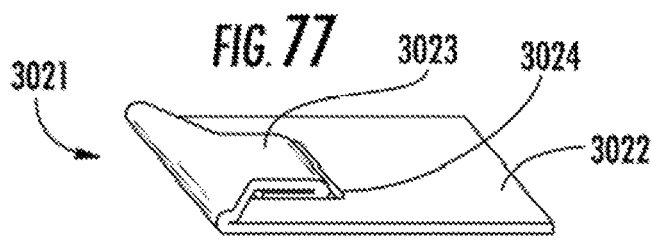
FIG. 78 depicts a perspective view of the exemplary removable covering of FIG. 76 in a phase of manufacturing.

FIG. 78 depicts a perspective view of the central section 3021 after the attachment section 3023 has been folded over the second fold axis shown in FIG. 77. As shown, a portion of the attachment section 3023 is positioned in the opening 3024.

Figure 79:
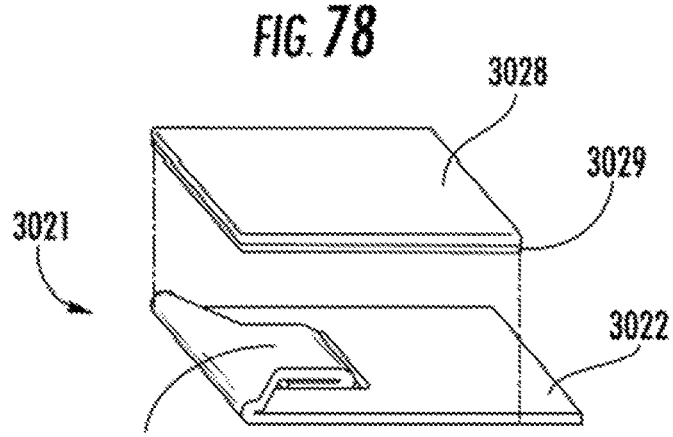
FIG. 79 depicts a perspective view of the exemplary removable covering of FIG. 76 and an object in a phase of manufacturing.

FIG. 79 depicts a perspective view of the central section 3021 and an object 3028 with a receiving surface 3029 (e.g., an adhesive layer).

Figure 80:
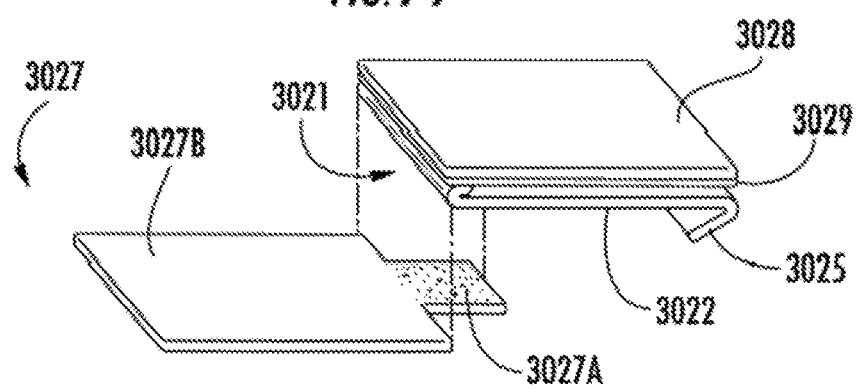
FIG. 80 depicts a perspective view of the exemplary removable covering and object of FIG. 79.

FIG. 80 depicts a perspective view of the central section 3021, the object 3028, and an extension section 3027. As shown, the object 3028 and receiving surface 3029 are positioned on the central section's attachment section 3023 and body section 3022. The object 3028 may be adhesed to the central section 302 (e.g., via an adhesive layer). The right portion of the body section 3022 has been folded downward to form a primary pull tab 3025.

The extension section 3027 includes an extension body 3027B and an extension attachment 3027A. The extension attachment 3027A is typically adhesed to the portion of the attachment section 3023 positioned in the opening 3024. The extension section 3027 may be folded around the edge of the object 3028 and may also be adhesed to the top surface of the object 3028 (e.g., via an adhesive layer).

In FIGS. 76-80, the central section 3021 and extension section 3027 can function together as an exemplary removable covering. As shown, the exemplary removable covering can be applied to an object. That said, two removable coverings in accordance with FIGS. 76-80 can be used together, one in the orientation shown in FIGS. 76-80 and one rotated 180 degrees in the same plane around the right edge of the body section 3022. In this regard, a single, larger removable covering having the same left and right sides can be used on a larger object.

Figure 81:
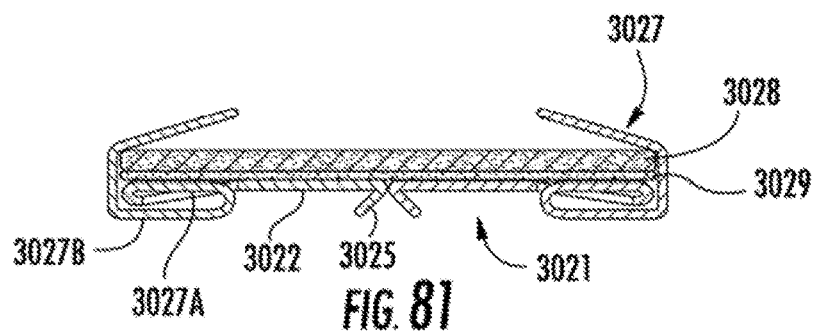
FIG. 81 depicts a side view of an exemplary removable covering and object.

For example, FIG. 81 depicts a side view of such a removable covering and an object 3028 having a receiving surface 3029 (e.g., an adhesive layer). In other words, the left and right sides of the removable covering each include a central section 3021 and an extension section 3027. The central section 3021 includes an attachment section (not shown), a body section 3022, an opening (not shown) in the body section 3022, and a primary pull tab 3025. The extension section 3027 includes an extension body 3027B and an extension attachment 3027A. As shown in FIG. 81, the extension section 3027 is folded around the edge of the object 3028.

Figure 82:
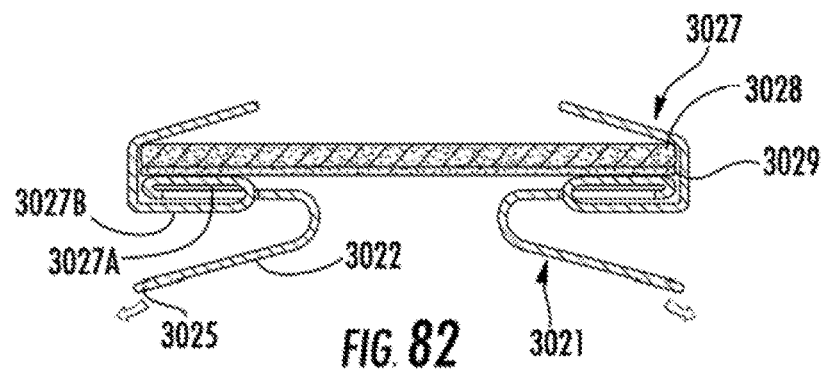
FIG. 82 depicts a side view of the exemplary removable covering and object of FIG. 81 in a phase of removal.

FIG. 82 depicts a side view of the exemplary removable covering and object 3028 of FIG. 81 in a phase of removal. In particular, the central section's primary pull tab 3025 has been pulled with a force to overcome a 180 degree peel strength resistance and the central section's body section 3022 has been removed from the receiving surface 3029.

Figure 83:
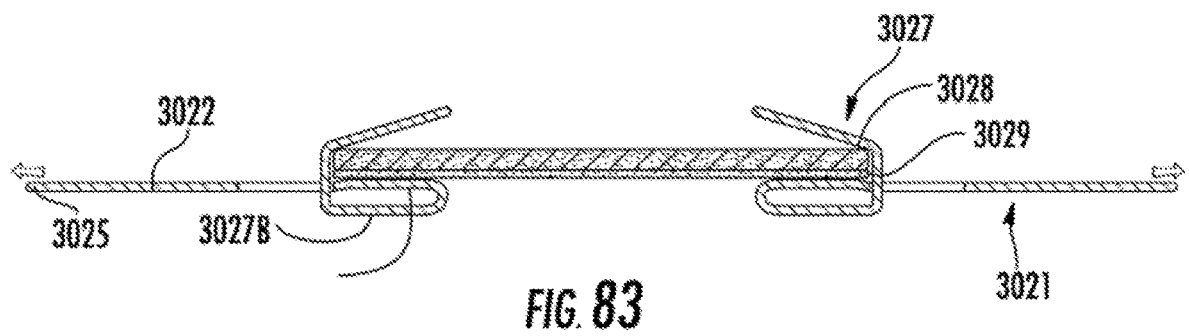
FIG. 83 depicts a side view of the exemplary removable covering and object of FIG. 81 in a phase of removal.

FIG. 83 depicts a side view of the exemplary removable covering and object 3028 of FIG. 81 in a further phase of removal. In particular, the central section's primary pull tab 3025 has been pulled to its full extension leaving the portion of the attachment section 3023 that was folded over the second fold axis (See FIGS. 77 and 78) adhesed to the receiving surface 3029. In this position, there is a shear peel strength resistance to a force pulling on the ends of the central section 3021.

Figure 84:
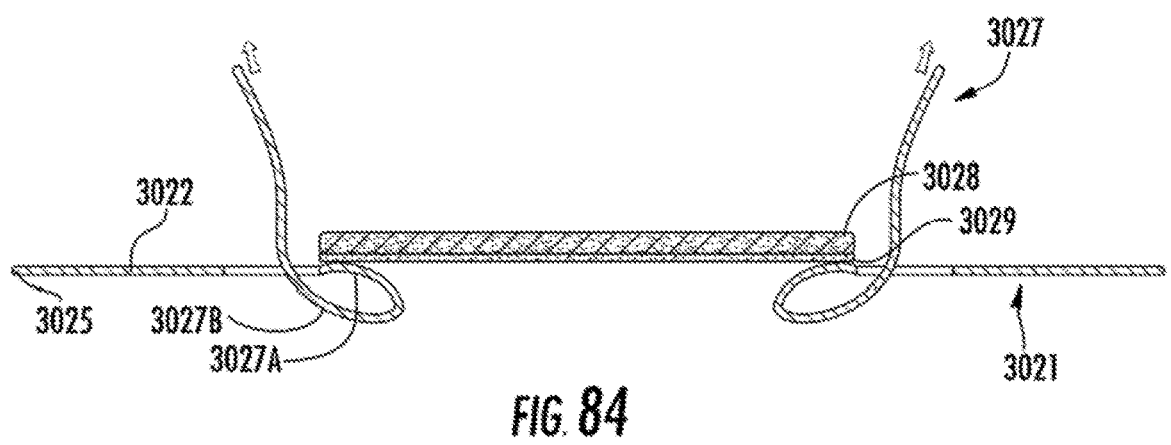
FIG. 84 depicts a side view of the exemplary removable covering and object of FIG. 81 in a phase of removal.
Figure 89:
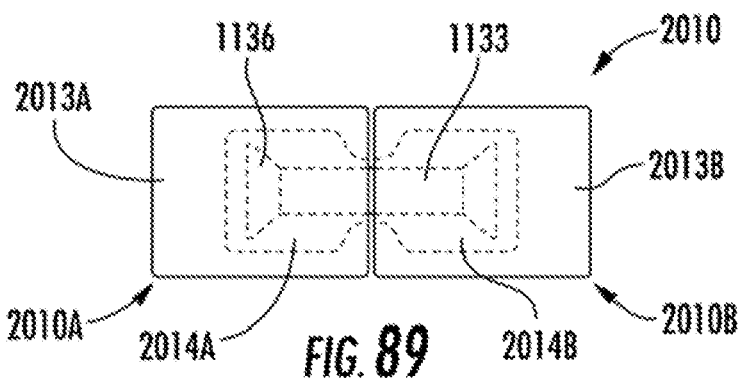
FIG. 89 depicts an overhead view of the exemplary packaging system, removable covering, and object of FIG. 86 in a phase of removal.
Figure 90:
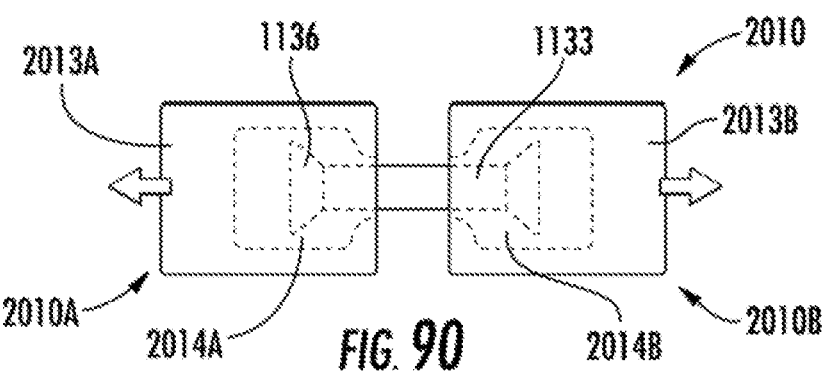
FIG. 90 depicts an overhead view of the exemplary packaging system, removable covering, and object of FIG. 86 in the same phase of removal as shown in FIG. 86.

FIG. 84 depicts a side view of the exemplary removable covering and object of FIG. 81 in a further phase of removal. In particular, the extension section 3027 has been engaged by pulling the portion of the extension body 3027B that has been folder over the object 3028. Because of the folded configuration around the attachment of the central section 3021 and the extension section 3027, the force required to remove the removable covering must overcome a 180 degree peel strength resistance.

In this regard, exemplary embodiments of the present invention embrace a removable covering that provides a change in resistance to covering removal along a force vector by means of a pass-through construction that varies the peel resistance on difference surfaces of the object to which the covering attaches.

FIG. 85 depicts a side view of an exemplary packaging system 2010, removable covering 1131, and object 1133 having a receiving surface 1132 (e.g., an adhesive layer). Each side (i.e., the left and right sides) of the exemplary removable covering 1131 includes a primary tab 1134 (e.g., a central terminus or free section) and an extension section 1136 that are not adhered to the receiving surface 1132 of the object 1133. The removable covering 1131 also includes a central section 1135 (e.g., an adhered section) that is adhered to the receiving surface 1132.

As shown, the extension section 1136 extends beyond the outer edge of the object 1133. The extension section 1136 interacts with the packaging system 2010 to provide additional resistance to complete removal and may have a variety of shapes (as viewed from overhead).

The packaging system 2010 includes two pieces, a left-side sleeve 2010A and a right-side sleeve 2010B, that may or may not be joined by an adhesive layer 2011. The sleeves 2010A and 2010B each include a top side 2013A and 2013B and a bottom side 2012A and 2012B, respectively.

The exemplary removable covering 1131 and packaging system 2010 function together to facilitate placement of the object 1133 and its receiving surface 1132. In this regard, each primary tab 1134 (i.e., on the left and right portions of the removable covering 1131) is typically adhered to each respective bottom side 2012A or 2012B of the packaging system 2010 (e.g., via the adhesive layer 1138 as shown).

FIGS. 86-88 depict side views of the exemplary removable covering 1131, object 1133, and packaging system 2010 of FIG. 85 in different phases of removal. As shown in FIG. 86, when a user pulls the left and right side sleeves 2010A and 2010B away from each other the removable covering 1131 is removed as well. Initially, there is a 180 degree peel strength resistance as the central section 1135 is removed from the receiving surface 1132. As discussed, the extension section 1136 interacts with the packaging system 2010 to provide additional resistance to complete removal. FIG. 87 depicts the moment at which the extension section 1136 begins to interact with the packaging system 2010 in this exemplary embodiment. In particular, the extension section 1136 gets caught in the packaging system 2010, thereby increasing the resistance to removal, before the central section 1135 is removed from the receiving surface 1132. By increasing the resistance to removal at this phase of removal, a user may more easily apply the object to a surface before completely removing the removable covering 1131 and packaging system 2010.

FIGS. 89-92 depict overhead views of the exemplary packaging system 2010, removable covering 1131, and object 1133 in the different phases of removal depicted in FIGS. 85-88, respectively. In this regard, the packaging system 2010 including the left-side sleeve 2010A and the right-side sleeve 2010B with their respective top sides 2013A and 2013B is shown. The outermost dotted lines indicate the free space 2014A and 2014B within the adhered portion of the packaging system 2010 between a given sleeve's top side and bottom side (See also FIGS. 85-88). Beyond the dotted lines, the top and bottom sides of the sleeves are adhered to each other. The interior dotted lines indicate the location of the extension section 1136 and the object 1133. The other components of the removable covering 1131 (e.g., the central section 1135 and the primary tab 1134) are below the object 1133 and, therefore, are not shown in FIG. 89 or 90.

Figure 91:
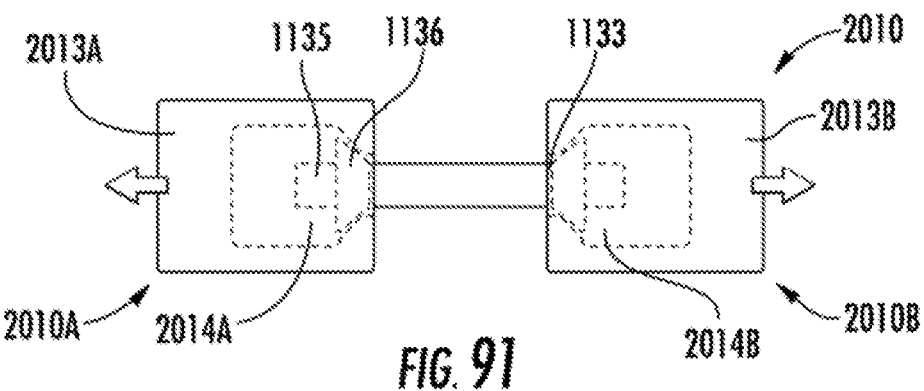
FIG. 91 depicts an overhead view of the exemplary packaging system, removable covering, and object of FIG. 86 in the same phase of removal as shown in FIG. 87.

As shown, the extension sections 1136 have a tapered shape and the free space 2014A and 2014B tapers in width near the central edge of each sleeve 2010A and 2010B. As shown in FIG. 91, when a user pulls the left and right side sleeves 2010A and 2010B away from each other, the extension section 1136 meets the tapered portion of the free space 2014A and 2014B within the packaging system 2010. In FIG. 91, a portion of the central section 1135 is shown extending outside of the extension section 1136. As discussed, this interaction of the extension section 1136 and the packaging system 2010 increases the resistance to removal and facilitates the user's placement and application of the object 1133. The resistance to removal between the extension section 1136 at this point is equivalent to a shear peel strength resistance, whereas the resistance to removal between the central section 1135 and the receiving surface 1132 is a weaker 180 degree peel strength resistance.

Figure 92:
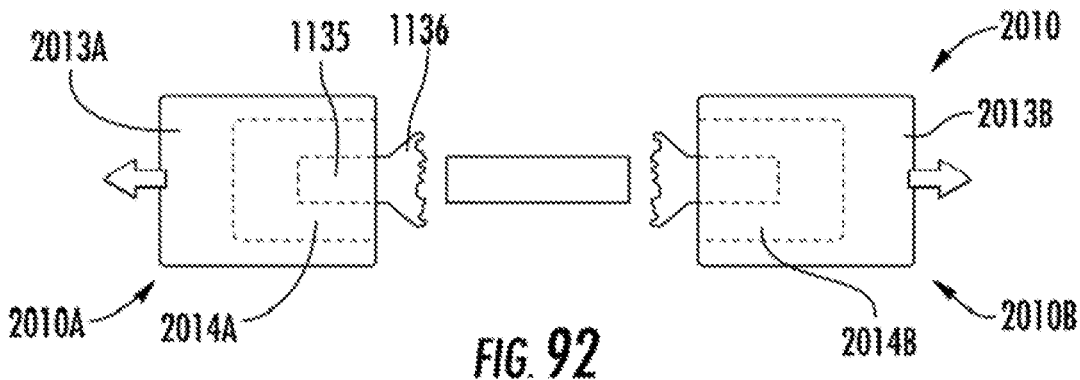
FIG. 92 depicts an overhead view of the exemplary packaging system, removable covering, and object of FIG. 86 in the same phase of removal as shown in FIG. 88.

As shown in FIG. 92, the extension section 1136 may force open the tapered portion of the free space 2014A and 2014B within the packaging system 2010 or the extension section 1136 may deform to pass through the central edge of the packaging system 2010.

Figure 93:
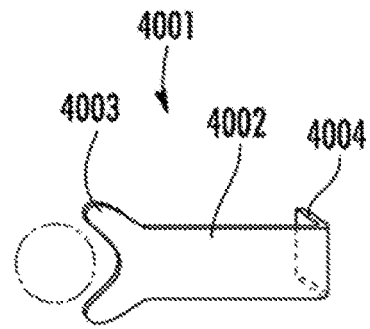
FIG. 93 depicts a perspective view of an exemplary extension section.
Figure 94:
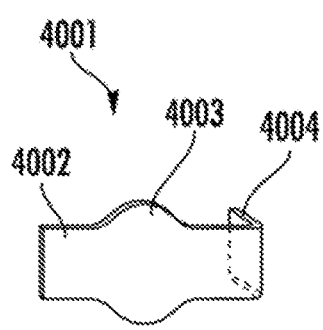
FIG. 94 depicts a perspective view of another exemplary extension section.

Extension sections that interact with a packaging system can have a variety of shapes to provide varying removal resistances and may be adhered to the top of an object. For example, FIGS. 93 and 94 depict perspective views of exemplary extension sections 4001. As shown, the extension sections 4001 include body section 4002, a resistance feature 4003, and a pull tab 4004. The extension section's resistance feature 4003 in FIG. 93 is shaped to accommodate grasping (i.e., within the circle) of the packaging with which it interacts. The extension section's resistance feature 4003 in FIG. 94 is located in the middle of the body section 4002 to provide resistance earlier in the removal process as compared to the extension section's resistance feature 4003 in FIG. 93. Alternatively, the length of the body section 4002 may be increased or decreased or the placement of the extension section 4001 on the object or removable covering may be varied to achieve increased resistance at a given phase of the removal process.

Figure 95:
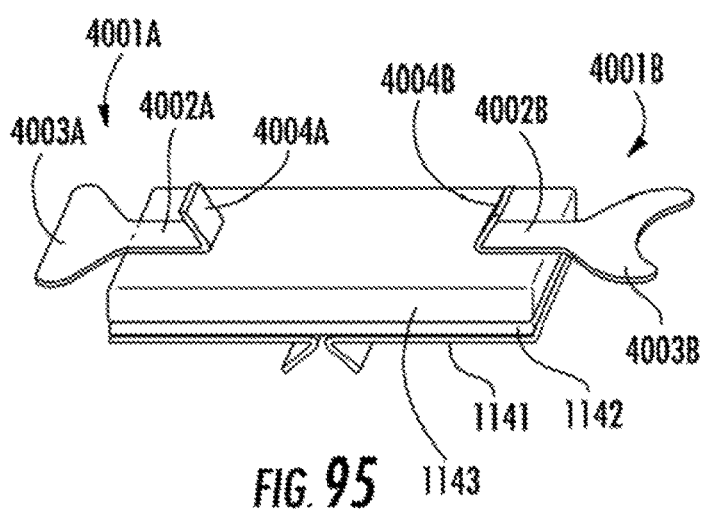
FIG. 95 depicts a perspective view of two exemplary extension sections adhered to an object and an exemplary removable covering.

FIG. 95 depicts a perspective view of two exemplary extension sections 4001A and 4001B adhered to the top surface of an object 1143 having a receiving surface 1142 adhered to an exemplary removable covering 1141. As shown, the extension sections 4001A and 4001B each include a body section 4002A and 4002B, a resistance feature 4003A and 4003B, and a pull tab 4004A and 4004B. The pull tabs 4004A and 4004B may be engaged to remove the extension sections 4001A and 4001B from the object 1143. Alternatively, the pull tabs 4004A and 4004B may be adhered to packaging in such a way that the extension sections 4001A and 4001B are removed as the packaging is pulled by the user.

Figure 96:
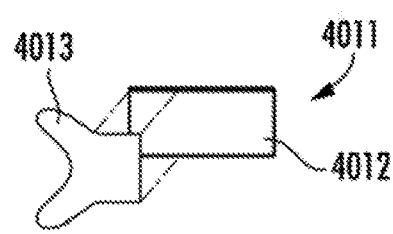
FIG. 96 depicts an exemplary two-piece extension section in a phase of manufacture.
Figure 97:
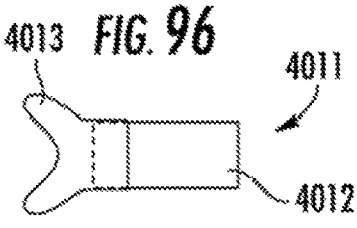
FIG. 97 depicts the exemplary two-piece extension section of FIG. 96 as manufactured.

FIGS. 96-97 depict an exemplary two-piece extension section 4011 that includes a body section 4012 and a resistance feature 4013. As shown, the resistance feature 4013 may be adhered to the body section 4012 creating a two-layer zone shown in FIG. 97.

Figure 98:
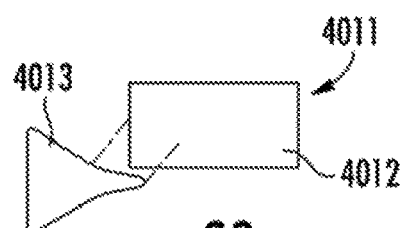
FIG. 98 depicts another exemplary two-piece extension section in a phase of manufacture.
Figure 99:
FIG. 99 depicts the exemplary two-piece extension section of FIG. 98 as manufactured.

FIGS. 98-99 depict another exemplary two-piece extension section 4011 that includes a body section 4012 and a different resistance feature 4013. As shown, the resistance feature 4013 may be adhered to the body section 4012 creating a two-layer zone shown in FIG. 99. As compared to the two-layer zone in FIG. 97, the two-layer zone in FIG. 99 is smaller, which may provide manufacturing advantages or improved functionality.

Figure 100:
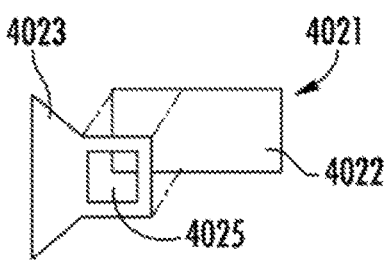
FIG. 100 depicts another exemplary two-piece extension section in a phase of manufacture.
Figure 101:
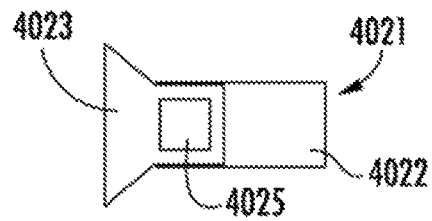
FIG. 101 depicts the exemplary two-piece extension section of FIG. 100 as manufactured.

FIGS. 100-101 depict another exemplary two-piece extension section 4021 that includes a body section 4022 and a resistance feature 4023 that further includes an opening 4025. The opening 4025 provides a smaller two-layer zone, which may provide manufacturing advantages or improved functionality.

FIG. 102 depicts a side view of an exemplary removable covering 1151, exemplary extension sections 4031, and an object 1153 having a receiving surface 1152 (e.g., an adhesive layer). Each side (i.e., the left and right sides) of the exemplary removable covering 1151 has the same components. The removable covering 1151 includes a primary tab 1154 that is not adhered to the receiving surface 1152 and a first adhered section 1155 that is adhered to the receiving surface (e.g., via an adhesive layer). As shown, the primary tab 1154 is adhered to a stiffening section 1159 via an adhesive layer 1158. The stiffening section 1159 may not be included in some exemplary embodiments.

The exemplary extension sections 4031 are adhered to the lateral portion of each side of the removable covering 1151 (i.e., the removable covering's first adhered section 1155) via an adhesive layer 1156. In this regard, the overlapped and adhered portions of the removable covering's first adhered section 1155 and the extension section 4031 form a two-layer backing, which affects the removable covering's resistance to removal.

FIG. 103 depicts the exemplary removable covering 1151, exemplary extension sections 4031, and object 1153 of FIG. 102 within a packaging system 2020. The packaging system 2020 includes two pieces, a left-side sleeve 2020A and a right-side sleeve 2020B, that may or may not be joined by an adhesive layer 2021. The sleeves 2020A and 2020B each include a top side 2023A and 2023B and a bottom side 2022A and 2022B, respectively.

The exemplary removable covering 1151, exemplary extension sections 4031, and packaging system 2020 function together to facilitate placement of the object 1153 and its receiving surface 1152. In this regard, each stiffening section 1159 (i.e., on the left and right portions of the removable covering 1151) is typically adhered to each respective bottom side 2022A or 2022B of the packaging system 2020. In alternative embodiments, each primary tab 1154 is adhered to each respective bottom side 2022A or 2022B of the packaging system 2020.

FIGS. 104-106 depict side views of the exemplary removable covering 1151, object 1153, exemplary extension sections 4031, and packaging system 2020 of FIG. 102 in different phases of removal, while FIG. 107 graphically depicts the application force or resistance necessary to remove the exemplary removable covering 1151 from the object 1153 as a function of time. In FIG. 107, "Phase 0" corresponds to FIGS. 102 and 103; "Phase 1" corresponds to FIG. 104; and "Phase 2" corresponds to FIG. 105.

As shown in FIG. 104, when a user pulls the left and right side sleeves 2020A and 2020B away from each other the removable covering 1151 is removed as well. Phase 0 is followed by the pulling apart of the left and right side sleeves 2020A and 2020B which requires the application of a middle opening force. Phase 1 requires a force to overcome a 180 degree peel strength resistance.

In Phase 2, the required force transitions from the force required to overcome the 180 degree peel strength resistance to a force capable of overcoming (i) a constriction resistance and (ii) an increased 180 degree peel strength resistance. The constriction resistance is a result of the interaction between the extension sections 4031 and the packaging system 2020 described with respect to FIGS. 62-65 and 85-101. In this regard, the constriction resistance depends on the shape of the extension sections 4031 and the free space within and construction of the left and right side sleeves 2020A. Accordingly, the extension sections 4031 and the left and right side sleeves 2020A may be designed to achieve a particular constriction force.

As noted, Phase 2 requires a force capable of overcoming (i) the constriction resistance and (ii) an increased 180 degree peel strength resistance. The increased 180 peel strength resistance is a result of the two-layer backing formed by the overlapped and adhered portions of the removable covering's first adhered section 1155 and the extension section 4031. See e.g., FIG. 105. After Phase 2, the constriction resistance and increased 180 degree peel strength resistance are overcome.

Figure 108:
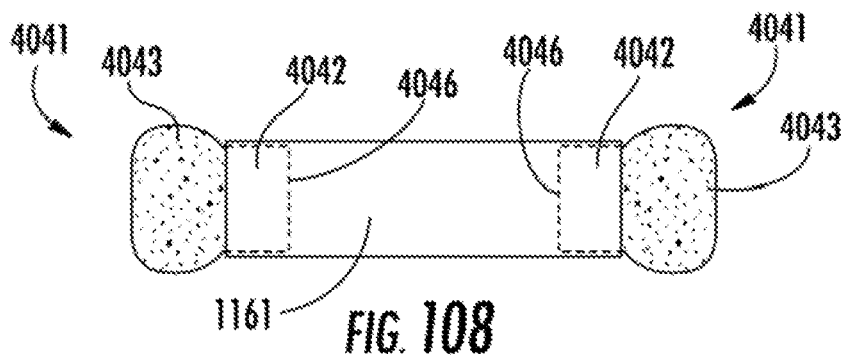
FIG. 108 depicts an overhead view of the exemplary removable covering, exemplary extension sections, and object of FIG. 102.

FIGS. 108-112 depict overhead views of exemplary extension sections 4041 and exemplary removable coverings 1161. The depicted extension sections 4041 include a body section 4042 and a resistance feature 4043. As shown in FIG. 108, when an extension section 4041 is applied to a removable covering 1161, at least a portion of the body section 4042 overlaps with the removable covering 1161 to form an overlap zone 4046. Because the overlap zone is thicker, it is stiffer or less deformable than the removable covering 1161 or resistance feature 4043. Varying the shape of the overlap zone 4046, therefore, can also vary the resistance to removal as the removable covering 1161 and/or extension sections 4041 interact with a packaging to create a constriction resistance.

Figures 109, 110, 111:
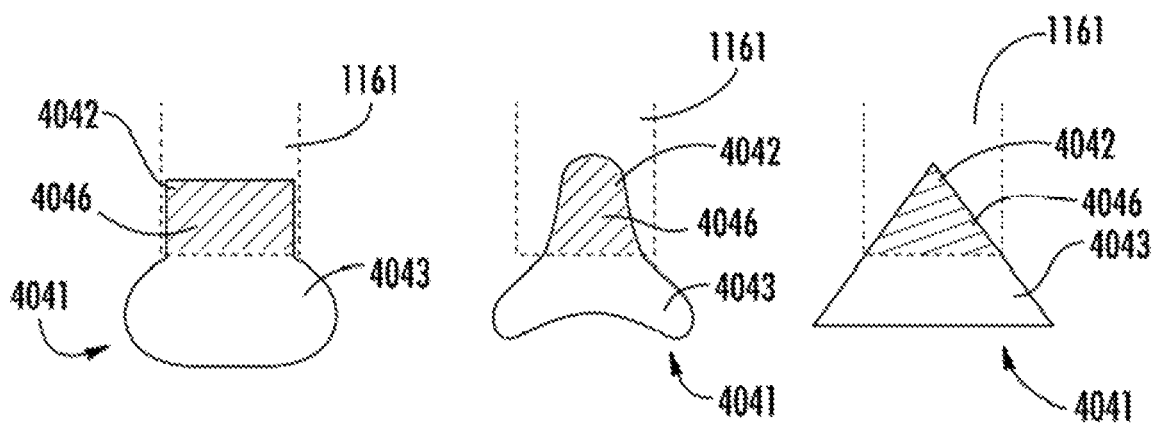
FIG. 109 depicts an overhead view of an exemplary extension section.
FIG. 110 depicts an overhead view of another exemplary extension section.
FIG. 111 depicts an overhead view of yet another exemplary extension section.

For example, the overlap zone 4046 in FIG. 109 is wider than the overlap zone in FIG. 110. Accordingly, for a given width at a packaging constriction point, the extension section 4041 and removable covering 1161 of FIG. 109 would provide more constriction resistance than the extension section 4041 and removable covering 1161 of FIG. 109.

Furthermore, the rate at which the constriction resistance increases can also be varied using the shape of the overlap zone 4046. For example, the overlap zone 4046 of FIG. 109 will cause an abrupt increase in constriction resistance as the overlap zone 4046 reaches the constriction point. In contrast, the overlap zone 4046 of FIG. 111 will provide a gradual increase in constriction resistance as more of the overlap zone 4046 passes through the constriction point (i.e., from top to bottom). Finally, the overlap zone 4046 of FIG. 110 will provide a gentle gradual increase in constriction resistance (i.e., less increase in constriction resistance per distance pulled as compared to FIG. 111).

Figure 112:
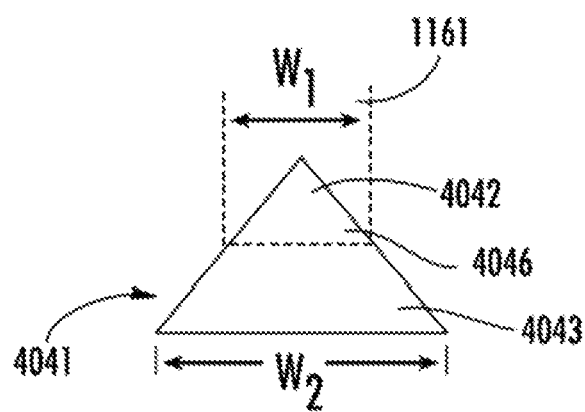
FIG. 112 depicts an overhead view of yet another exemplary extension section.

As shown in FIG. 112, the variation in constriction resistance created by the shape of the extension section 4041 and its resistance feature 4043 can be assessed by comparing the width $W_1$ of the removable covering 1161 and the maximum width $W_2$ of the extension section's resistance feature 4043. Typically, a greater difference between the resistance feature's width $W_2$ and the removable covering's width $W_1$ will results in a greater constriction resistance.

Figure 113:
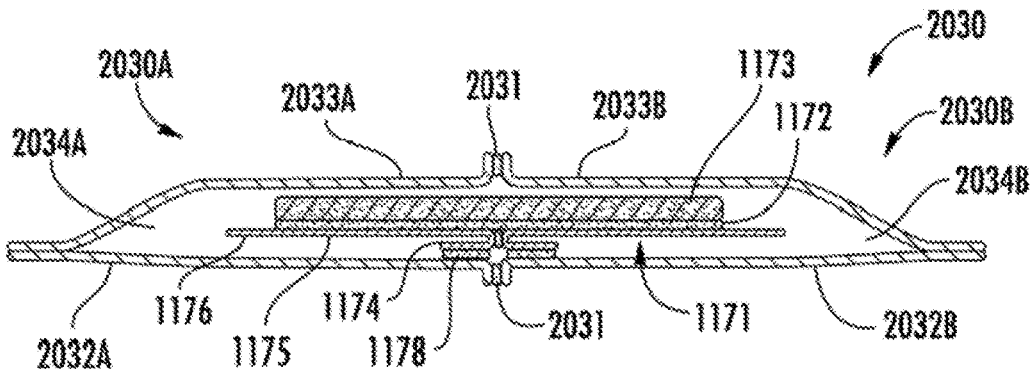
FIG. 113 depicts a side view of an exemplary removable covering that includes extension sections and an object within an exemplary packaging system.

FIG. 113 depicts a side view of an exemplary packaging system 2030, removable covering 1171, and object 1173 having a receiving surface 1172 (e.g., an adhesive layer). Each side (i.e., the left and right sides) of the exemplary removable covering 1171 includes a primary tab 1174 (e.g., a central terminus or free section) and an extension section 1176 that are not adhered to the receiving surface 1172 of the object 1173. The removable covering 1171 also includes a central section 1175 (e.g., an adhered section) that is adhered to the receiving surface 1172.

As shown, the extension section 1176 extends beyond the outer edge of the object 1173. The extension section 1176 interacts with the packaging system 2030 to provide additional resistance to complete removal and may have a variety of shapes (as viewed from overhead).

The packaging system 2030 includes two pieces, a left-side sleeve 2030A and a right-side sleeve 2030B, that may or may not be joined by an adhesive layer 2031. The sleeves 2030A and 2030B each include a top side 2033A and 2033B and a bottom side 2032A and 2032B, respectively. The sleeves 2030A and 2030B also each include a free space 2034A and 2034B between the respective top and bottom sides.

The exemplary removable covering 1171 and packaging system 2030 function together to facilitate placement of the object 1173 and its receiving surface 1172. In this regard, each primary tab 1174 (i.e., on the left and right portions of the removable covering 1171) is typically adhered to each respective bottom side 2032A or 2032B of the packaging system 2030 (e.g., via the adhesive layer 1178 as shown).

Figure 114:
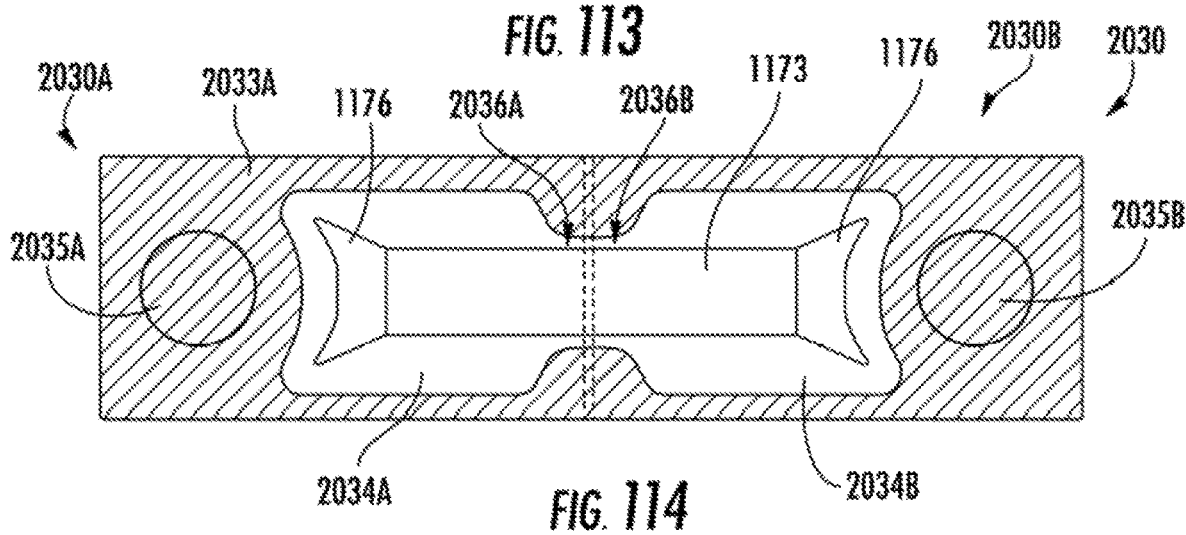
FIG. 114 depicts an overhead view of the exemplary removable covering, object, and an exemplary packaging system of FIG. 113.

FIG. 114 depicts an overhead view of the exemplary packaging system 2030, removable covering 1171, and object 1173. As shown, the sleeves 2030A and 2030B also each include a grasping section 2035A and 2035B and a constriction point 2036A and 2036B. Each constriction point is created by adhering the top and bottom side of a given sleeve such that the fee space is narrower near the center or midline of the packaging system 2030.

Figure 115:
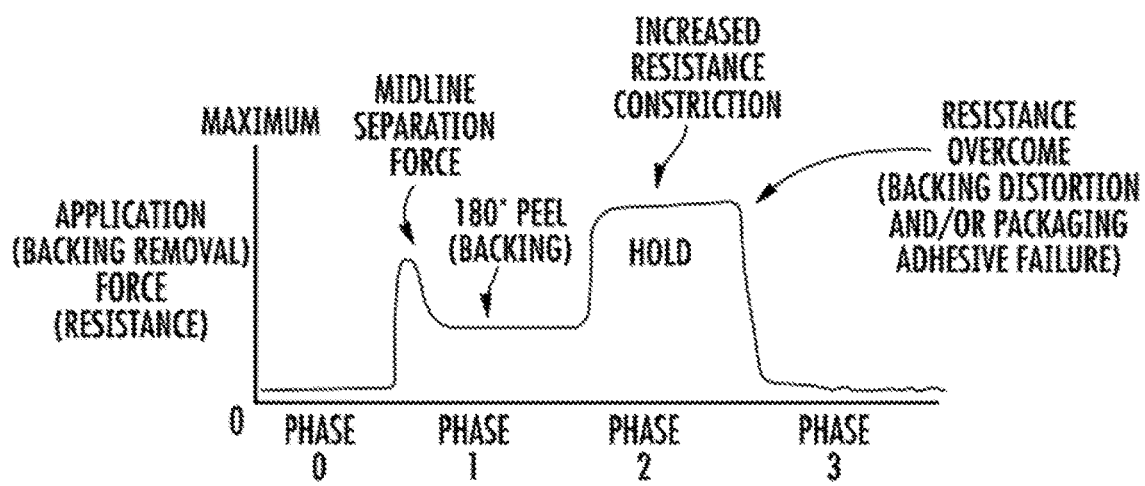
FIG. 115 graphically depicts the application force or resistance necessary to remove the packaging system and exemplary removable covering of FIG. 113 from the object as a function of time.

FIG. 115 graphically depicts the application force or resistance necessary to remove the exemplary removable covering 1171 from the object 1173 as a function of time. In FIG. 115, "Phase 0" corresponds to FIGS. 113 and 1114.

When a user pulls (e.g., via the grasping sections 2035A and 2035B) the left and right side sleeves 2030A and 2030B away from each other the removable covering 1171 is removed as well. Phase 0 is followed by the pulling apart of the left and right side sleeves 2030A and 2030B which requires the application of a midline separation force. Phase 1 requires a force to overcome a 180 degree peel strength resistance as the central section 1175 is peeled away from the receiving surface 1172.

In Phase 2, the required force increases from the force required to overcome the 180 degree peel strength resistance to a force capable of overcoming a constriction resistance. The constriction resistance is a result of the interaction between the extension sections 1176 and the packaging system 2030 described with respect to FIGS. 62-65 and 85-112. In this regard, the constriction resistance depends on the shape of the extension sections 1176, the free spaces 2034A and 2034B, and the constriction points 2036A and 2036B. For example, as shown in FIG. 114, the maximum width of the extension sections 1176 is greater than the width of the constriction points 2036A and 2036B. Thus, when the sleeves 2030A and 2030B have been pulled far enough away from each other that the extension sections 1176 meet the constriction points 2036A and 2036B, a constriction resistance will impede further pulling of the sleeves. During Phase 2, most, if not all, of the object 1173 and its receiving surface 1172 will be out of the packaging system 2030, and the user may hold the packaging system 2030 and place the object 1173 and its receiving surface 1172 in a desired location (e.g., on another surface).

During Phase 3, the user pulls the sleeves 2030A and 2030B with sufficient force to overcome the constriction resistance. The constriction resistance may be overcome by distortion of the extension sections 1176 or failure of the adhesive between the top and bottom sides of the sleeves at the constriction points 2036A and 2036B.

In this regard, exemplary embodiments of the present invention embrace a removable covering that provides a change in resistance to covering removal along a force vector by means of a constriction mechanism that varies the amount of resistance exhibited by the packaging and therefore the peel resistance of the backing. In embodiments in which removing the packaging also peels the removable covering, the peel resistance can be adjusted by incorporating a plugging feature that restricts the ability of the removable covering to slide through a passageway in the packaging.

Figure 116:
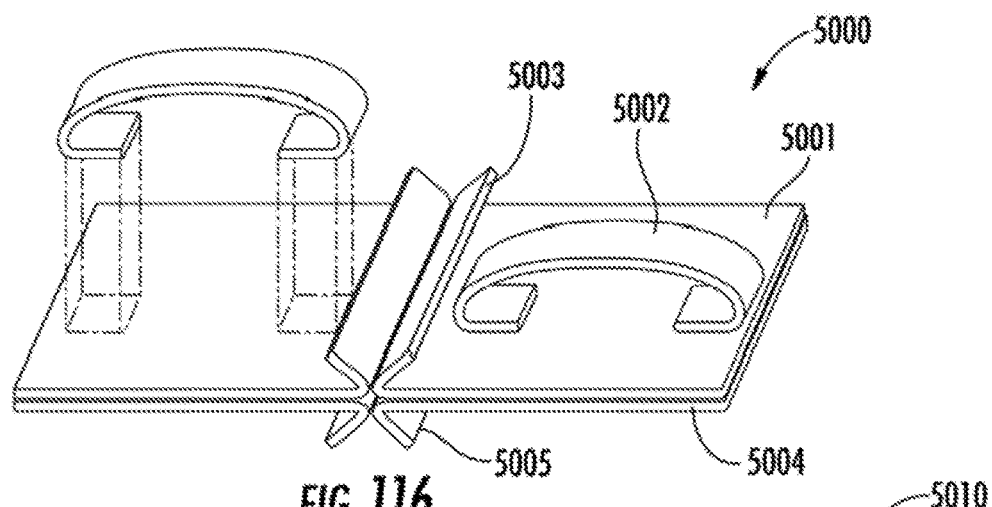
FIG. 116 depicts a perspective view of an exemplary packaging system in a phase of manufacture.

FIG. 116 depicts a perspective view of an exemplary packaging system 5000 that includes left and right sleeves having the same components. In particular, each sleeve includes a top side 5001, a handle element 5002, a top tab 5003, a bottom side 5004, and a bottom tab 5005. The handle element 5002 is a strip having ends adhered to the top side 5001. In use, a user can place two fingers from the same hand in each handle element 5002 and expose an object within the sleeves by spreading the two fingers apart.

Figure 117:
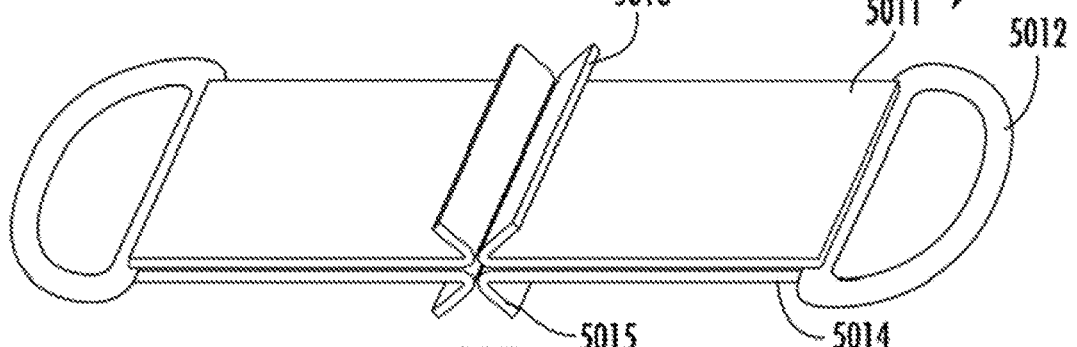
FIG. 117 depicts a perspective view of another exemplary packaging system.

FIG. 117 depicts a perspective view of another exemplary packaging system 5010 that includes left and right sleeves having the same components. In particular, each sleeve includes a top side 5011, a handle element 5012, a top tab 5013, a bottom side 5014, and a bottom tab 5015. The handle element 5012 is a D-shaped ring having a flat portion adhered to the outer edge of each sleeve. Again, in use, a user can place two fingers from the same hand in each handle element 5012 and expose an object within the sleeves by spreading the two fingers apart.

Figure 118:
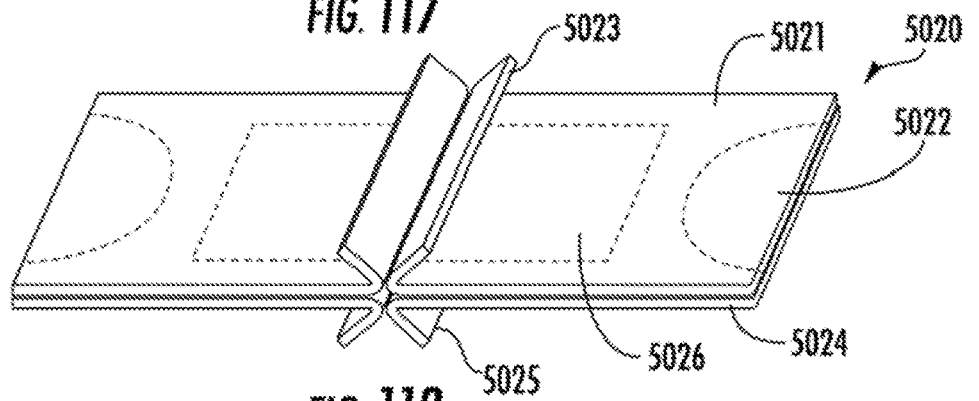
FIG. 118 depicts a perspective view of yet another exemplary packaging system.

FIG. 118 depicts a perspective view of yet another exemplary packaging system 5020 that includes left and right sleeves having the same components. In particular, each sleeve includes a top side 5021, a handle element 5022, a top tab 5023, a bottom side 5024, and a bottom tab 5025. The handle element 5022 is created by an arc-shaped perforation at the outer edge of each sleeve. As shown, the arc-shaped perforation does not overlap the object 5026 within the sleeves. The arc-shaped perforations may or may not extend to the outer edges of the sleeves. In use, a user can break the perforation on each sleeve, place two fingers from the same hand in each handle element 5022, and expose an object within the sleeves by spreading the two fingers apart.

Figure 119:
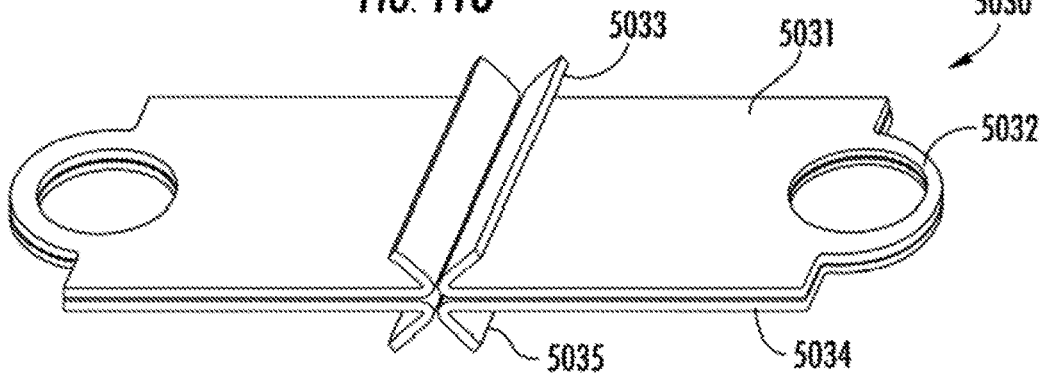
Figure 120:
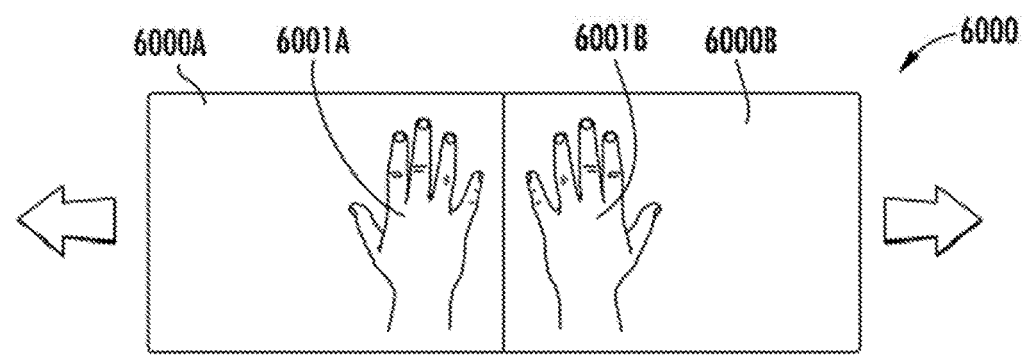

FIG. 119 depicts a perspective view of yet another exemplary packaging system 5030 that includes left and right sleeves having the same components. In particular, each sleeve includes a top side 5031, a handle element 5032, a top tab 5033, a bottom side 5034, and a bottom tab 5035. The handle element 5032 is a circular opening formed by an arc of packaging material extending from the outer edge of each sleeve and a cutout from the outer edge of each sleeve. Again, in use, a user can place two fingers from the same hand in each circular opening and expose an object within the sleeves by spreading the two fingers apart.

In this regard, exemplary embodiments of the present invention embrace a removable covering that provides a change in resistance to covering removal along a force vector by means of a change in direction of the removable covering resulting from manually extending the packaging via attached or integral handles (e.g., handle elements). The user separates the packaging via the handles or tabs, and the packaging provides a first peeling force vector at a first peel resistance and peeling angle. The user can then complete the peeling by accessing secondary tabs (e.g., top tabs and/or bottom tabs) that are peeled at a peeling angle between 90 and 180 degrees.

Figure 121:
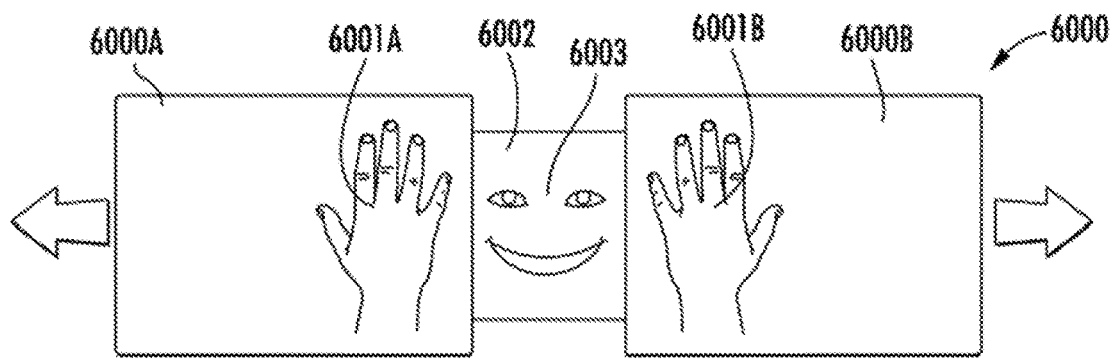
Figure 122:
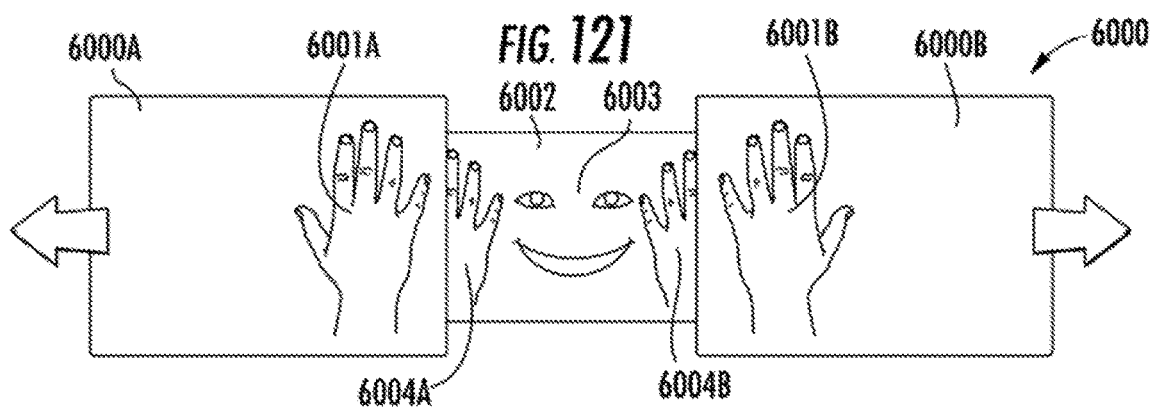
Figure 123:
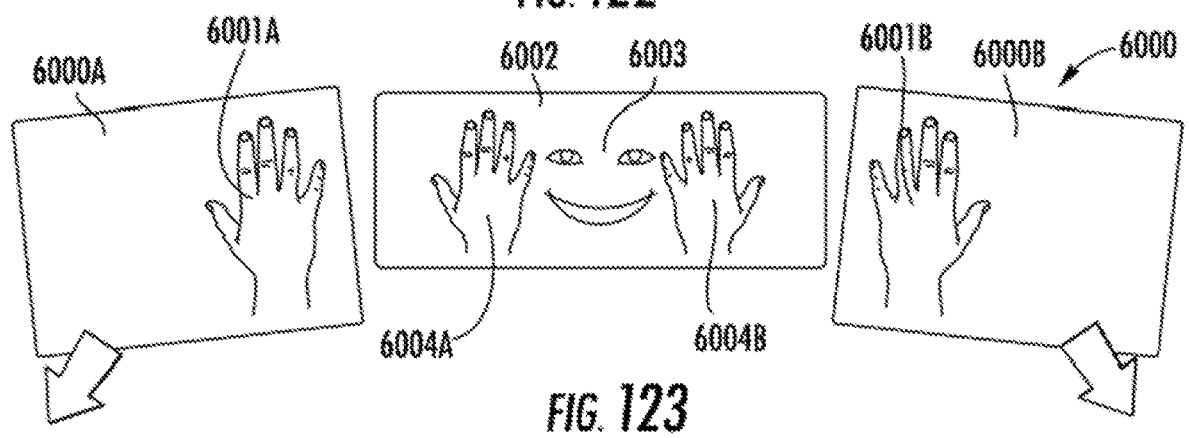

FIGS. 120-123 depict overhead views of an exemplary packaging system 6000 and object 6002. The packaging system 6000 includes a left sleeve 6000A and a right sleeve 6000B each including a visible design element 6001A and 6001B (e.g., an image of a hand). As shown in FIG. 123, the object 6002 bears a centrally-positioned visible design element 6003 (e.g., an image of a face), a left-side visible design element 6004A (e.g., an image of a hand) and a right-side visible design element 6004B (e.g., an image of a hand). In the depicted exemplary embodiment, the visible design elements 6001A and 6001B are the same as the left-side visible design element 6004A and right-side visible design element 6004B, although the size of the elements may be different. Furthermore, the depicted exemplary design elements are related in such a way as to convey a story as the sleeves 6000A and 6000B of the packaging system 6000 is removed from the object 6002.

As shown in FIG. 121, during a first phase of removal, the centrally-positioned design element 6003 becomes visible as the sleeves 6000A and 6000B are separated. As depicted, the story conveyed shows a face, originally hidden behind two hands, being revealed as the two hands move outward to the left and right.

During a second phase of removal depicted in FIG. 122, the left-side visible design element 6004A and right-side visible design element 6004B on the object 6002 become partially visible as the sleeves 6000A and 6000B are separated even further. As depicted, the story conveyed shows that the face is still visible and the two hands appear to be ceasing movement further from either side of the face.

During the final phase of removal depicted in FIG. 123, the left-side visible design element 6004A and right-side visible design element 6004B on the object 6002 are fully visible and the sleeves 6000A and 6000B have been completely removed from the object 6002. As depicted, the story conveyed shows that face is still visible and the two hands have stopped movement and are positioned on either side of the face.

Figure 124:
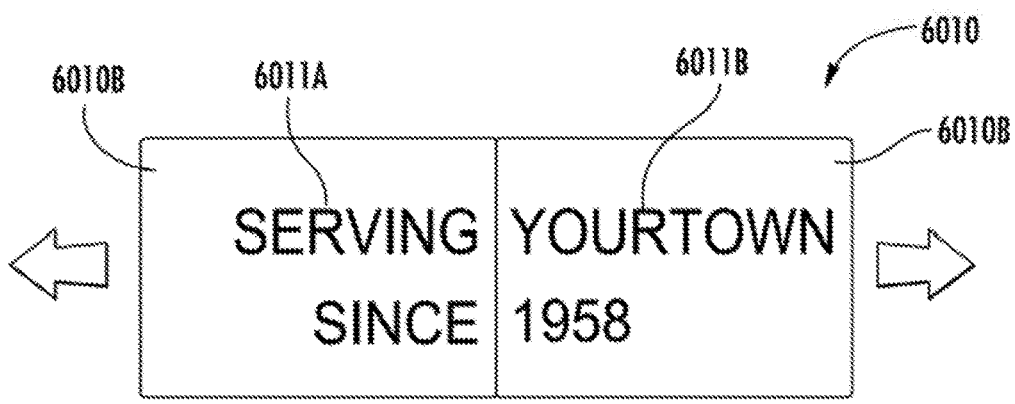
Figure 125:
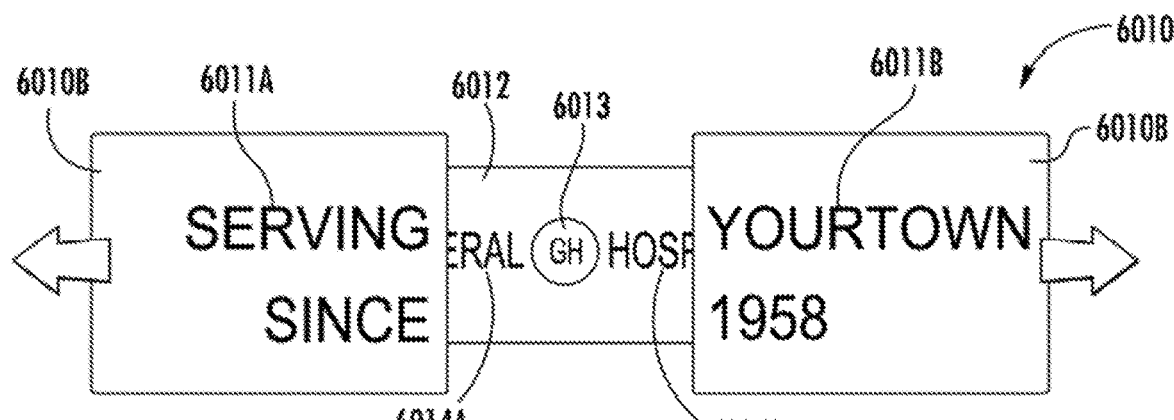
Figure 126:
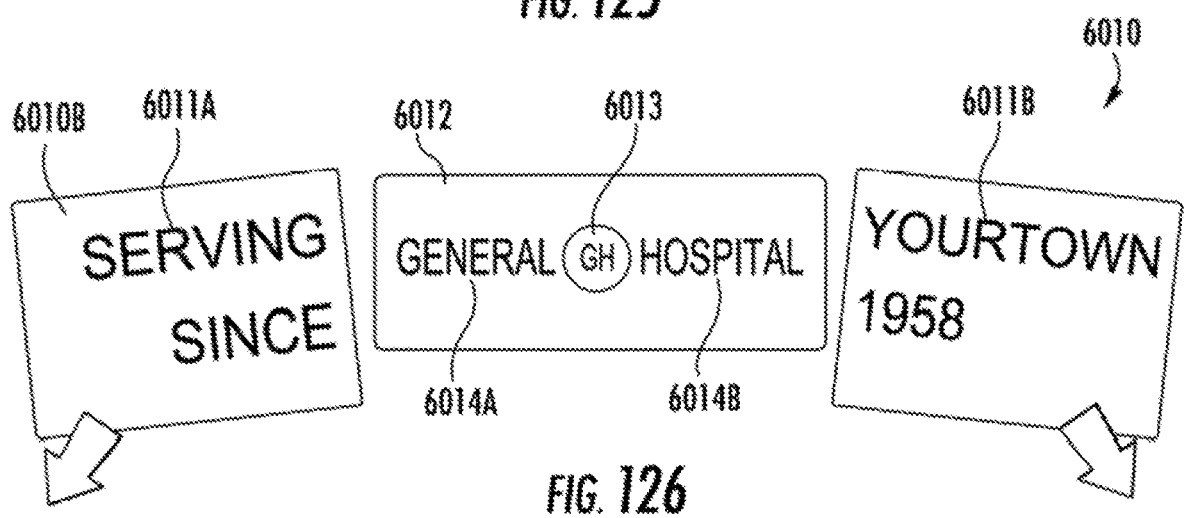

FIGS. 124-126 depict overhead views of another exemplary packaging system 6010 and object 6012. The packaging system 6010 includes a left sleeve 6010A and a right sleeve 6010B each including a visible design element 6011A and 6011B (e.g., text, a slogan, a logo, a trademark, a part of a trademark, a name, a part of name, and/or abbreviation). The visible design elements 6011A and 6011B may be related, as shown in FIG. 124, to convey a message or present an image. As shown in FIGS. 125-126, the object 6002 bears a centrally-positioned visible design element 6013 (e.g., text, a slogan, a logo, a trademark, a part of a trademark, a name, a part of name, and/or abbreviation), a left-side visible design element 6014A (e.g., text, a slogan, a logo, a trademark, a part of a trademark, a name, a part of name, and/or abbreviation) and a right-side visible design element 6014B (e.g., text, a slogan, a logo, a trademark, a part of a trademark, a name, a part of name, and/or abbreviation). The depicted exemplary design elements are related in such a way as to convey a message as the sleeves 6010A and 6010B of the packaging system 6010 is removed from the object 6012. As shown, the visible design elements 6011A and 6011B on the packaging system's sleeves 6010A and 6010B present a message or information about the visible design elements 6013, 6014A, 6014B.

During a first phase of removal, the centrally-positioned design element 6013 becomes visible as the sleeves 6010A and 6010B are separated. During a second phase of removal depicted in FIG. 125, the left-side visible design element 6014A and right-side visible design element 6014B on the object 6012 become partially visible as the sleeves 6010A and 6010B are separated even further. During the final phase of removal depicted in FIG. 126, the left-side visible design element 6014A and right-side visible design element 6014B on the object 6012 are fully visible and the sleeves 6010A and 6010B have been completely removed from the object 6012. In this regard, the packaging system and object and the visible design element's they bear convey a message or information that can be used as a marketing tool.

Figure 127:
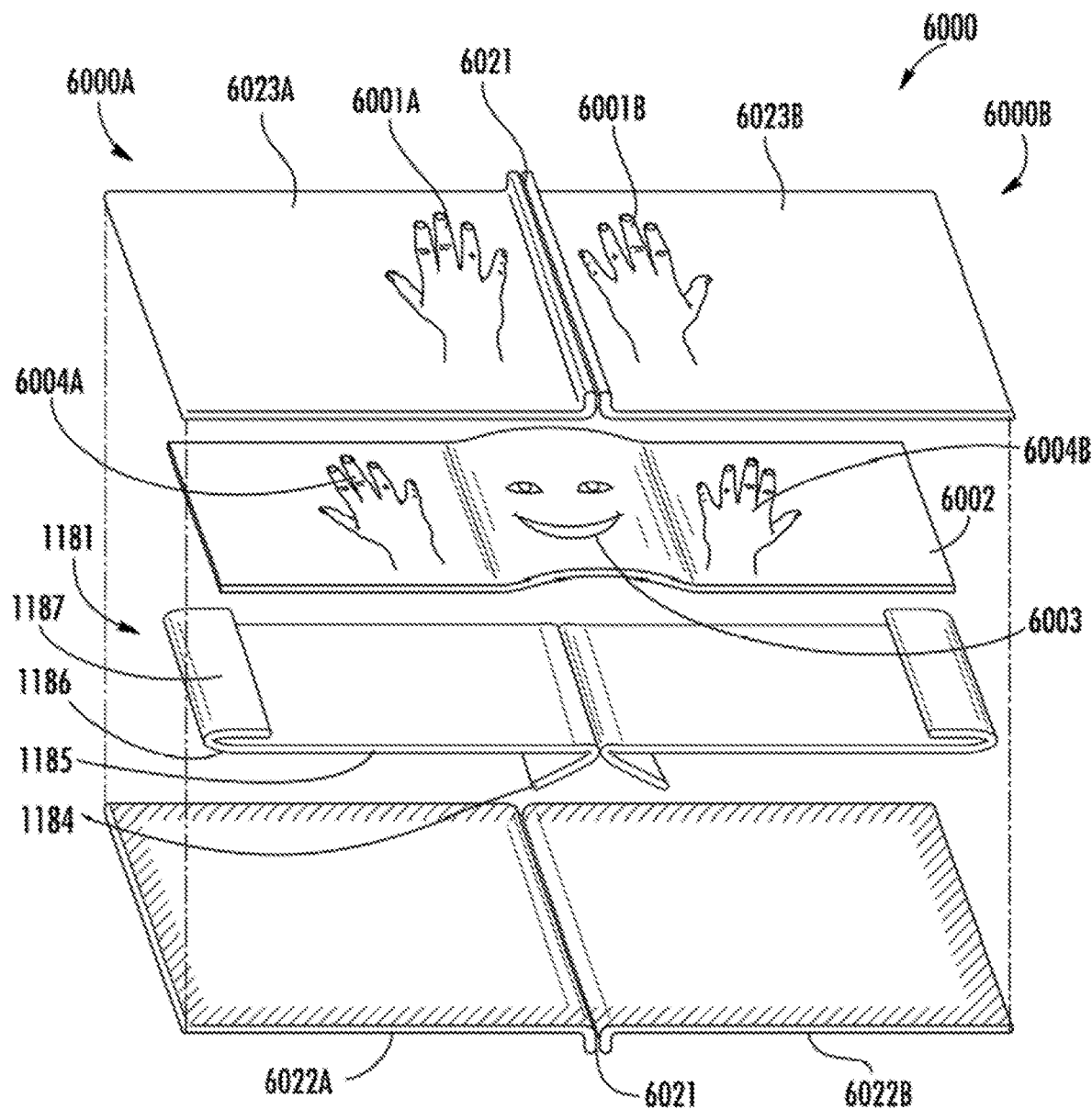

FIG. 127 depicts a perspective view of the exemplary packaging system 6000 and object 6002 of FIGS. 120-123 as well as an exemplary removable covering in a phase of manufacturing. The packaging system 6000 includes two pieces, a left-side sleeve 6000A and a right-side sleeve 6000B, that may or may not be joined by an adhesive layer 6021. The sleeves 6000A and 6000B each include a top side 6023A and 6023B and a bottom side 6022A and 6022B, respectively. The top sides 6023A and 6023B each include a visible design element 6001A and 6001B (e.g., an image of a hand).

The object 6002 bears a centrally-positioned visible design element 6003 (e.g., an image of a face), a left-side visible design element 6004A (e.g., an image of a hand) and a right-side visible design element 6004B (e.g., an image of a hand). In the depicted exemplary embodiment, the visible design elements 6001A and 6001B are the same as the left-side visible design element 6004A and right-side visible design element 6004B, although the size of the elements may be different.

Each side (i.e., the left and right sides) of the exemplary removable covering 1181 includes a primary tab 1184 (e.g., a central terminus or free section) and a lateral free section 1185 that are not adhered to the bottom surface of the object 6002. The removable covering 1181 also includes a central section 1185 (e.g., an adhered section) and a lateral adhered section 1186 that is adhered to the bottom surface of the object 6002.

The exemplary removable covering 1181 and packaging system 6000 may function together to facilitate placement of the object 6002 and its receiving surface (e.g., bottom surface). In this regard, each primary tab 1184 (i.e., on the left and right portions of the removable covering 1181) may be adhered to each respective bottom side 6022A or 6022B of the packaging system 6000 (e.g., via an adhesive layer).

In this regard, exemplary embodiments of the present invention embrace a removable covering that provides at least two step changes in resistance to covering removal along a force vector directed to associated packaging, wherein the first step change reveals a first portion of an image on the receiving surface, and the second step change reveals the remainder of the image on the receiving surface.

Figure 128:
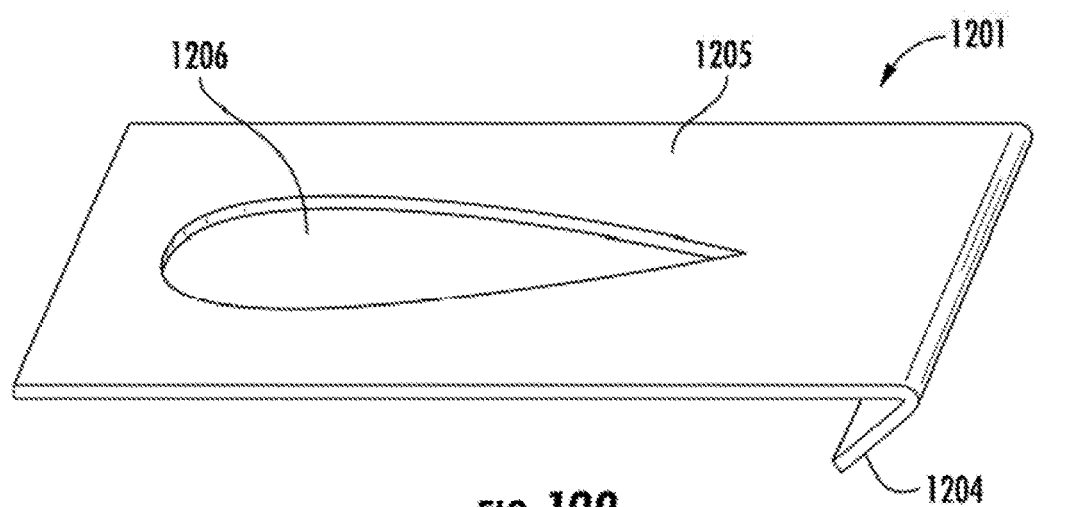
Figure 129:
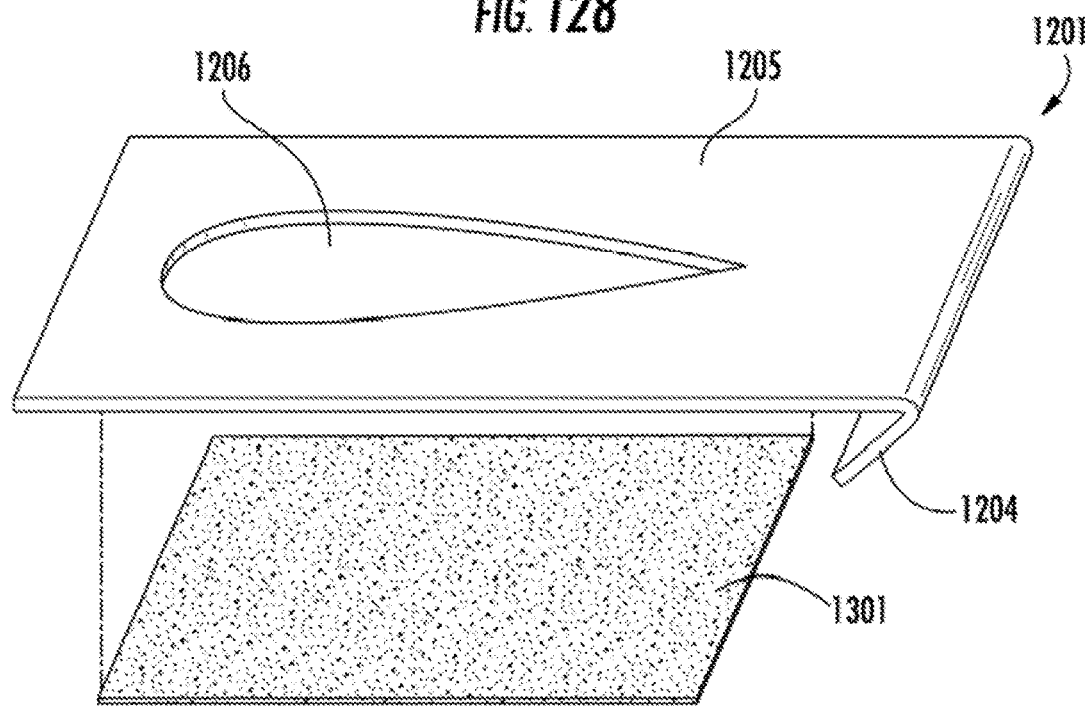
Figure 130:
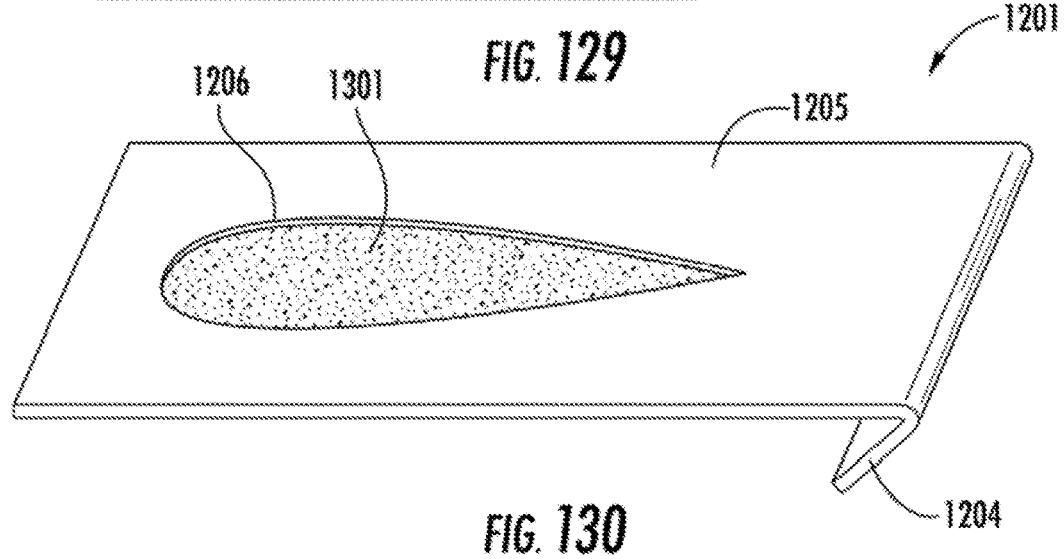

FIGS. 128-130 depict perspective views of another exemplary removable covering 1201 that achieves a varied resistance to removal. The removable covering 1201 includes a primary tab 1204 (e.g., a central terminus or free section) and a body section 1205 (e.g., a central section or adhered section) having an opening 1206. An adhesive layer 1301 is applied to the bottom surface of the body section 1205 and is exposed to objects on the top surface of the removable covering 1201 through the opening 1206.

During removal, as a user grasps the primary tab 1204 and pulls the removable covering 1201 away from an object, initially the resistance to removal is determined by the interaction between the body section 1205 and the surface of the object, which may be an adhesive layer. At a later phase of removal, the right-side of the opening 1206 and adhesive layer 1301 and their interaction with the surface of the object will affect the resistance to removal. Typically, the resistance to removal will increase because the adhesive layer 1301 will provide greater resistance. As more of the removable covering 1201 is pulled away from the object (i.e., from right to left as depicted), the progressively larger width-wise section of the opening 1206 and exposed adhesive layer 1301 will increase the resistance to removal.

In this exemplary embodiment, the shape of the opening 1206 will affect the manner in which the resistance to removal varies during the removal process. In particular, the percentage of the removable covering's width that the opening 1206 encompasses at a given cross-section taken at an angle that is 90 degrees to the axis along which the removable covering is removed (e.g., the width-wise cross-section as depicted) will affect the resistance to removal at a given phase of removal. Thus, the depicted tear-drop-shaped opening 1206 will provide a resistance to removal that gradually increases during the removal process and then, towards the end, decreases somewhat quickly. It is within the scope of the present invention to employ other shapes of openings to achieve a desired variation in resistance to removal.

FIG. 131 depicts a perspective view of another exemplary removable covering 1211 that achieves a varied resistance to removal. The removable covering 1211 includes a primary tab 1214 and a body section 1215. As shown, a shaped-adhesive strip 1311 may be applied to the body section 1215. The upper surface of the body section 1215 and the shaped-adhesive strip 1311 are typically placed on a receiving surface (e.g., an adhesive layer) of an object.

During removal, as a user grasps the primary tab 1214 and pulls the removable covering 1211 away from an object, initially the resistance to removal is determined by the interaction between the body section 1215 and the surface of the object, which may be an adhesive layer. At a later phase of removal, the shaped-adhesive strip 1311 and its interaction with the surface of the object will affect the resistance to removal. Typically, the resistance to removal will increase because the shaped-adhesive strip 1311 will provide greater resistance. As more of the removable covering 1211 is pulled away from the object (i.e., from right to left as depicted), the progressively larger width-wise section of the shaped-adhesive strip 1311 will increase the resistance to removal.

In this exemplary embodiment, the shape of the adhesive strip 1311 will affect the manner in which the resistance to removal varies during the removal process. In particular, the percentage of the removable covering's width that the shaped-adhesive strip 1311 encompasses at a given cross-section taken at an angle that is 90 degrees to the axis along which the removable covering is removed (e.g., the width-wise cross-section as depicted) will affect the resistance to removal at a given phase of removal. Thus, the depicted tear-drop-shaped adhesive strip 1311 will provide a resistance to removal that gradually increases during the removal process and then, towards the end, decreases somewhat quickly. It is within the scope of the present invention to employ other shapes of adhesive strips to achieve a desired variation in resistance to removal.

FIG. 132 depicts a perspective view of yet another exemplary removable covering 1221 that achieves a varied resistance to removal. The removable covering 1221 includes a primary tab 1224 and a body section 1225. As shown, the body section 1225 may include a shaped-coating zone 1226. The upper surface of the body section 1225 and the shaped-coating zone 1226 are typically placed on a receiving surface (e.g., an adhesive layer) of an object. As depicted, the body section 1225 may have a different coating than the shaped-coating zone 1226. The coatings may be release coatings (e.g., a siliconized coating), but, in this exemplary embodiment, the coatings are different and provide two different resistances to removal when combined with an adhesive layer on an object.

During removal, as a user grasps the primary tab 1224 and pulls the removable covering 1221 away from an object, initially the resistance to removal is determined by the interaction between the body section 1225 and the surface of the object, which may be an adhesive layer. At a later phase of removal, the shaped-coating zone 1226 and its interaction with the surface of the object will affect the resistance to removal. Typically, the resistance to removal will increase because the shaped-coating zone 1226 will provide greater resistance. As more of the removable covering 1211 is pulled away from the object (i.e., from right to left as depicted), the progressively larger width-wise section of the shaped-coating zone 1226 will increase the resistance to removal.

In this exemplary embodiment, the shape of the coating zone 1226 will affect the manner in which the resistance to removal varies during the removal process. In particular, the percentage of the removable covering's width that the shaped-coating zone 1226 encompasses at a given cross-section taken at an angle that is 90 degrees to the axis along which the removable covering is removed (e.g., the width-wise cross-section as depicted) will affect the resistance to removal at a given phase of removal. Thus, the depicted tear-drop-shaped-coating zone 1226 will provide a resistance to removal that gradually increases during the removal process and then, towards the end, decreases somewhat quickly. It is within the scope of the present invention to employ other shapes of coating zones to achieve a desired variation in resistance to removal.

FIG. 133 depicts an overhead view of an exemplary removable covering 1231 that achieves a varied resistance to removal. The removable covering 1231 includes a body section 1235 and a shaped-coating zone 1236 having a higher resistance to removal than the body section 1235 (e.g., via adhesive differences and/or coating release agent differences). During removal, the top end of the removable covering 1231 is initially removed from an object.

The application force necessary to remove the exemplary removable covering 1231 from an object at a given cross-section taken at an angle that is 90 degrees to the axis along which the removable covering is removed (e.g., the width-wise cross-section as depicted) may be determined by (i) measuring the widths A, B, and C of the cross-sectional segments of body section and shaped-coating zone, (ii) multiplying the measured widths by a relative resistance factor, and (iii) adding them. For example, assuming the shaped-coating zone 1236 has a resistance to removal that is twice the resistance to removal provided by the body section 1235, the application force necessary to remove the exemplary removable covering 1231 from an object at a given cross-section is given by: F=1A+2B+1C.

In this regard, FIG. 134 graphically depicts the application force or resistance necessary to remove the exemplary removable covering 1231 from an object as a function of distance along the peel-axis (i.e., the axis along which the removable covering is removed). As shown, initially the resistance increases gradually, and then decreases briefly at the lower, narrow section of the shaped-coating zone 1236. The brief decrease in resistance warns or signals to a user that the removable covering 1231 is near complete removal. The resistance then increases at the end of the removal process to facilitate placement of the object.

FIG. 135 depicts an overhead view of another exemplary removable covering 1241 that achieves a varied resistance to removal. The removable covering 1241 includes a body section 1245 and a shaped-coating zone 1246 having a lower resistance to removal than the body section 1245 (e.g., via adhesive differences and/or coating release agent differences). During removal, the top end of the removable covering 1241 is initially removed from an object.

The application force necessary to remove the exemplary removable covering 1241 from an object at a given cross-section taken at an angle that is 90 degrees to the axis along which the removable covering is removed (e.g., the widthwise cross-section as depicted) may be determined by (i) measuring the widths A, B, and C of the cross-sectional segments of body section and shaped-coating zone, (ii) multiplying the measured widths by a relative resistance factor, and (iii) adding them. For example, assuming the shaped-coating zone 1246 has a resistance to removal that is one third of the resistance to removal provided by the body section 1245, the application force necessary to remove the exemplary removable covering 1241 from an object at a given cross-section is given by: F=3A+1B+3C.

In this regard, FIG. 136 graphically depicts the application force or resistance necessary to remove the exemplary removable covering 1241 from an object as a function of distance along the peel-axis (i.e., the axis along which the removable covering is removed). As shown, the resistance increases gradually, and then sharply decreases at the rapidly widening section of the shaped-coating zone 1246 at the end of the removable covering 1241. The decrease in resistance at the end of removal may facilitate placement of the object.

FIGS. 137-140 depict perspective views of an exemplary removable covering 1251 during different phases of removal. The exemplary removable covering 1251 includes a primary tab 1254, a body section 1255, and a varied-adhesion zone 1256. The varied-adhesion zone has a different resistance to removal than the body section 1255, which may be achieved via an increase or decrease in adhesive strength, different release coatings, or a change in texture. FIG. 137 depicts the removable covering 1251 as it would be applied to an object.

FIG. 138 depicts the removable covering 1251 in an early phase of removal. As shown, a first portion of the varied-adhesion zone 1256 has been pulled away and extends downward from the adhesion edge 1259 with the portion of the removable covering 1251 that has been removed. The adhesion edge 1259 effectively defines the boundary between the section of the removable covering 1251 that has been removed and the section of the removable covering 1251 that is still adhered to an object. The adhesion edge 1259 is typically a cross-section taken at an angle that is 90 degrees to the axis along which the removable covering is removed. The adhesion edge 1259 may not be exactly perpendicular to the axis along which the removable covering is removed because of non-exact removal by a user.

FIG. 139 depicts the removable covering 1251 in a further phase of removal. As shown, a greater portion of the varied-adhesion zone 1256 has been pulled away and extends downward from the adhesion edge 1259 with the portion of the removable covering 1251 that has been removed. Because the adhesion edge 1259 in FIG. 139 includes a greater percentage of the varied-adhesion zone 1256 than the adhesion edge 1259 in FIG. 138, the phase of removal shown in FIG. 139 has a different resistance to removal than the phase of removal shown in FIG. 138 (i.e., increased or decreased resistance to removal depending on the relative resistances to removal between the body section 1255 and the varied-adhesion zone 1256).

FIG. 140 depicts the removable covering 1251 in yet another phase of removal. As shown, an even greater portion of the varied-adhesion zone 1256 has been pulled away and extends downward from the adhesion edge 1259 with the portion of the removable covering 1251 that has been removed. Because the adhesion edge 1259 in FIG. 140 includes a different percentage of the varied-adhesion zone 1256 than the adhesion edge 1259 in FIG. 139, the phase of removal shown in FIG. 140 has a different resistance to removal than the phase of removal shown in FIG. 139 (i.e., increased or decreased resistance to removal depending on the relative resistances to removal between the body section 1255 and the varied-adhesion zone 1256).

FIGS. 141-144 depict perspective views of an exemplary removable covering 1261 during different phases of removal from an exemplary object 1263. The exemplary removable covering 1261 includes a primary tab 1264 and a body section 1265. The exemplary removable object 1263 includes a receiving surface 1262 (e.g., an adhesive layer) bearing a varied-adhesion zone 1266. The varied-adhesion zone 1266 has a different resistance to removal than the receiving surface 1262, which may be achieved via an increase or decrease in adhesive strength, different release coatings, or a change in texture.

FIG. 141 depicts the exemplary removable covering 1261 and exemplary object before the two are adhered as shown in FIG. 142. FIG. 143 depicts the removable covering 1261 in a phase of removal. As shown, a first portion of the body section 1265 has been pulled away from the object's receiving surface 1262 and extends downward from the adhesion edge 1269. The adhesion edge 1269 effectively defines the boundary between the section of the removable covering 1261 that has been removed and the section of the removable covering 1261 that is still adhered to the object 1263. The adhesion edge 1269 is typically a cross-section taken at an angle that is 90 degrees to the axis along which the removable covering is removed. The adhesion edge 1269 may not be exactly perpendicular to the axis along which the removable covering is removed because of non-exact removal by a user.

FIG. 144 depicts the removable covering 1261 in a further phase of removal. As shown, a smaller portion of the body section 1265 is in contact with the varied-adhesion zone 1266 and most of the body section 1265 extends downward from the adhesion edge 1269. Because the adhesion edge 1269 in FIG. 143 includes a greater percentage of the varied-adhesion zone 1266 than the adhesion edge 1269 in FIG. 144, the phase of removal shown in FIG. 143 has a different resistance to removal than the phase of removal shown in FIG. 144 (i.e., increased or decreased resistance to removal depending on the relative resistances to removal between the body section 1265 and the varied-adhesion zone 1256).

A comparison of the exemplary embodiments in FIGS. 137-140 and FIGS. 141-144 shows that the variation in resistance to removal can be achieved using a varied-adhesion zone on a removable covering (i.e., as in FIGS. 137-140) or on an object (i.e., as in FIGS. 141-144). Furthermore, combinations of these two exemplary embodiments (i.e., varied-adhesion zones on both the removable covering and the object) may also be employed to achieve a desired variation in resistance to removal.

FIG. 145 depicts an overhead view of an exemplary removable covering and an object 110, and FIG. 146 depicts a side view of the exemplary removable covering and object 110. The object includes a body portion 111, a central zone 112 (e.g., a central pad), and two end portions 114 and 116 on either side of the central zone 112. Portions of the removable covering are below the object 110 and, therefore, are shown by dotted lines in the overhead view of FIG. 145. The removable covering includes a first adhered section 120 and a second adhered section 122 that are adhered to the object 110 (e.g., via adhesive layers 117 and 118 as shown in FIG. 146). The removable covering also includes two handles 140 and 141 that are respectively connected to the first adhered section 120 and second adhered section 122 at their central ends (i.e., central with respect to the object 110). The two handles 140 and 141 extend upward from the underside of the object 110 and around the object 110. As depicted, the handles 140 and 141 are positioned around the central zone 112 of the object. That said, the handles 140 and 141 may be positioned anywhere along the length of the removable covering and/or object 110. The handles 140 and 141 facilitate removal of the removable covering from the object 110. For example, the handles 140 and 141 may be pulled in the direction of the arrows shown in FIG. 146. Furthermore, the handles 140 and 141 permit a user to remove the removable covering from the object 110 and apply the object 110 to a surface without accessing or manipulating the side of the object 110 that will be adhered to the surface. To facilitate the description, some of the components of the exemplary removable covering and object 110 are not shown in FIGS. 147-149.

In this regard, FIG. 147 depicts a side view of the exemplary removable covering of FIGS. 145 and 146 in a phase of removal from the object 110. As depicted, the handles 140 and 141 may be pulled outwardly. Initially, the resistance to removal is relatively low as the handles 140 and 141 pull the first adhered section 120 and second adhered section 121 away from the central zone 112, which typically does not include an adhesive layer. The resistance to removal then increases as the handles 140 and 141 pull the first adhered section 120 and second adhered section 121 away from the adhesive layers 117 and 118 (shown in FIG. 146 but not FIG. 147). Thus, the central zone 112 is exposed and may be applied to a surface (e.g., the skin of a patient) as shown in FIG. 148.

FIG. 148 depicts a side view of the exemplary removable covering of FIGS. 145 and 146 in a phase of removal from an object 110 and a phase of applying the object to a surface 129. As depicted, the handles 140 and 141 pull the first adhered section 120 and second adhered section 121 further away from the adhesive layers 117 and 118 (shown in FIG. 146 but not FIG. 148) and the object 110 is applied to a surface 129.

As depicted in FIG. 149 the handles 140 and 141 may be pulled further to remove the removable covering from the object 110, and the adhesive layers 117 and 118 (shown in FIG. 146 but not FIG. 149) may adhere to the surface 129 holding the object 110 in position. Any of the previously described mechanisms from creating a change or variation in resistance may be employed in conjunction with this exemplary embodiment.

FIG. 150 depicts an overhead view of an exemplary removable covering and an object 210, and FIG. 151 depicts a side view of the exemplary removable covering and the object 210. The object 201 includes a body section 211, a central zone 212, two end sections 214 and 216, and a central bridge 205. The removable covering includes a first adhered section 220 and a section adhered section 222 that are adhered to the object 210 (e.g., via an adhesive layer). The first adhered section 220 and the section adhered section 222 each include a tab on their respective ends nearest the center of the object 210 that facilitates removal from the object 210. Other exemplary embodiments, however, may not include these tabs. Alternatively, other interlocking tab mechanisms (e.g., adhesive layers, pin and hole mechanism, slot and tab mechanism) may be utilized. Typically, the ends of the first adhered section 220 and the section adhered section 222 that are nearest the center of the object 210 are not adhered to the object 210.

The removable covering also includes interlocking extension sections 242 and 243. As shown, the interlocking extension sections 242 and 243 include complimentary notches that interlock. The interlocking nature of the interlocking extension sections 242 and 243 may be achieved using other features or designs that provide different or varying degrees of pre-tensioning of the object 210 consistently before application to a surface (e.g., a wound). To facilitate the description, some of the components of the exemplary removable covering and object 210 are not shown in FIGS. 152-154.

FIG. 152 depicts a side view of the exemplary removable covering of FIGS. 150 and 151 in a phase of preparing the removable covering and object 210 for application to a surface. As shown, the ends of the removable covering and object 210 have been bent upward (i.e., away from the side of the object to be applied to a surface). The first adhered section 220 and the section adhered section 222 have been pulled away from the central bridge 205. In FIG. 153, the ends of the removable covering and object 210 have been bent further upward and the interlocking extension sections 242 and 243 have been interlocked. After interlocking the interlocking extension sections 242 and 243, the user may position the object 210 including the central bridge 205 over the surface (e.g., including a wound as shown). The first adhered section 220 and the section adhered section 222 have been pulled away from the object 210 even more so than in FIG. 152 contemporaneously exposing a larger section of an adhesive layer.

FIG. 154 depicts the object 210 including the central bridge 205 as applied to the surface. The interlocking extension sections 242 and 243 have been released from each other, and the bridge 205 provides tension across the surface. Typically, an adhesive on the object 210 and/or bridge 205 adheres the object 201 to the surface. The first adhered section 220 and the section adhered section 222 may be removed from the object 210, and the two end sections 214 and 216 may be adhered to the surface (e.g., via an adhesive layer). The sections of the first adhered section 220 and the section adhered section 222 that have been pulled away from the object 210 as a result of application process as depicted in FIGS. 152-154 may function as a tab for subsequent complete removal of first adhered section 220 and the section adhered section 222 from the object 210.

In the specification and/or figures, typical embodiments of the invention have been disclosed. The present invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

Exemplary Claim Embodiments

For the Backing

B1. A removable covering that is temporarily adhered to an object (adhesive on backing, object, or both) that has different zones of resistance to removal when subjected to a constant speed (or force) or direction of removal.

B2. A removable covering having different zones of resistance to removal from an object that can stabilize, orient, help apply, etc. an object because the different zones of resistance allow the object to be held by means of the backing.

B3. A removable covering according to B1 and/or B2 wherein mechanisms of varied resistance comprise:
a fold within the backing;
a loop within the backing;
different textures in covering or object (alters adhesive strength);
different amounts or strengths of the adhesives in different zones (covering or object);
two interactive layers to the covering (like pivot or hinge);
two separate layers to the backing;
adhering the covering to more than one surface of the object;
a tear away portion of the object itself;
temporary folds within the object itself;
a shift in direction of the backing; and/or
expandability (different between object and backing).

B4. A removable covering as in B1-B3 wherein accessory tabs, loops, folds, and/or other shapes help with final removal of the covering after an initial removal phase. (two steps)

B5. A removable covering as in B1-B3 which can be removed in a single step.

For the Envelope (Packaging System)

E1. An envelope which is removed coaxially by a force applied to opposite ends where the envelope has surfaces (e.g. folds) to accommodate the backing.

E2. An envelope which functions to assist in removal of a backing.

For the System (Envelope Plus Covering)

S1. A system where opposite coaxial force vectors applied to the envelope are transmitted to a section or sections of the backing.

S2. A system where such forces on the envelope lead to a partial removal of the covering which is followed by an increase in resistance to removal.

S3. A system where the increase in resistance can be overcome by continued increase in force going in the same direction.

S4. A system where the increase in resistance can be overcome by releasing a secondary force point (e.g. second tab or pull loop).

S5. A system where the increase in resistance stabilizes, orients, and/or prepares the object for placement.

S6. A system that allows the object to be partially exposed (activated) prior to complete covering removal. (without touching the device itself)

S7. A system that allows the object to be fully exposed (activated) prior to complete package removal. (without touching the device itself)

S8. A system that aligns the two halves to an equal degree of release from the envelope/covering by virtue of the increase in resistance.

S9. A system where the increase in resistance is created by inner lumen constriction between the protected device and the envelope.

S10. A system where the appearance of designs on the wrapping changes as the device is opened.

S11. A system that looks like hands moving away from a face (Peek-A-Boo-Boo).

D1. A device comprising:
a removable protective planar covering that can be adhered to portions of an object (protected object);
said removable protective covering having at least one section or structural feature not in direct contact with said object;
said device being of sufficient flexibility to allow at least partial removal from said protected device by application of a peel force vector applied to a section or structural feature of the backing;
so configured, applied to, and interacting with said object that the force required to remove the covering from said protected object varies at different zones of attachment between the removable covering and the object to which it is attached when a removal force vector is applied.

D2. A device comprising:
a removable protective planar covering that can be adhered to portions of an object (protected object);
said removable protective covering having at least one section or structural feature not in direct contact with said object;
said device being of sufficient flexibility to allow at least partial removal from said protected device by application of a peel force vector applied to a section or structural feature of the backing;
so configured, applied to, and interacting with said object that resistance to be overcome to remove the covering from said protected object varies at different zones of attachment between the removable covering and the object to which it is attached when a removal force vector is applied.

D3. A device comprising:
a packaging envelope constructed of two or more sections;
wherein said sections are adhesed to each other with an adhesive of such strength that they can be separated by the application of oppositely directed force vectors applied to opposing sides of packaging device itself;
wherein said packaging envelope has an attachment to a section of a protective covering.

A device as in D3 wherein the adhesive connection zones between opposing sides is oriented at 180 degrees to the axis of force applied to the opposing sides of the packaging device itself.

A device as in D3 wherein the adhesive connection zones between opposing sides is oriented at an angle between zero and 180 degrees.

A device as in D3 wherein the adhesive connection zones between opposing sides has a non-rectangular shape so as to facilitate separation of the opposing sections upon application of a force to the packaging device.

A device as in D3 where the adhesed sections are mirror images of each other.

A device as in D3 where the adhesed sections are not mirror images of each other.

A device as in D3 where the internal pocket dimensions of the packaging device exceed the dimensions of the contained object for which it is designed such that application of a compressing force to a section of the packaging device does not transmit pressure to the protected device.

A device as in D3 where the opposing sections to be separated may demonstrate loops, tabs, linear elements, strings, or other features to facilitate the application of a separating force.

A device as in D3 where the opposing sections can be fully separated by a single hand.

A device as in D3 where design elements such as a figure, character, logo, words or other features are visible on the surface of the device to aid in alignment or to create a change in appearance as the segments are separated.

D4. A system comprising:
a packaging device as in D3 with opposing sections that can be separated by the application of opposing forces to opposite sides of the opposing sections; and
a removable protective covering as in D1 and/or D2 which has been affixed to an object wherein the affixed object and removable covering are contained within the packaging device;
wherein a zone of the removable covering device is affixed to a zone of the packaging device such that the separation of the opposing sections of the packaging device transmits a separating force to the removable covering device which subsequently separates the removable covering device from the exposed object.

D5. A system comprising:
a packaging device as in D3 with opposing sections that can be separated by the application of opposing forces to opposite sides of the opposing sections; and
a removable protective covering as in D1 and D2 which has been affixed to an object wherein the affixed object and removable covering are contained within the packaging device;
wherein a zone of the removable covering device is affixed to a zone of the packaging device such that the separation of the opposing sections of the packaging device transmits a separating force to the removable covering device which subsequently separates the removable covering device from the exposed object at which point the interacting packaging system and removable covering exhibit an increase in resistance to an opening force.

D6. A system comprising:
a packaging device as in D3 with opposing sections that can be separated by the application of opposing forces to opposite sides of the opposing sections; and
a removable protective covering as in D1 and D2 which has been affixed to an object wherein the affixed object and removable covering are contained within the packaging device;
wherein the removable covering exhibits areas of varied width such that an increase in resistance to an opening force as applied to the packaging device occurs during removal of the packaging device and contained protective covering from the protected device.

D7. A system comprising:
a packaging device as in D3 with opposing sections that can be separated by the application of opposing forces to opposite sides of the opposing sections; and
a removable protective covering as in D1 and D2 which has been affixed to an object wherein the affixed object and removable covering are contained within the packaging device;
wherein the internal space width within a section of the packaging device exhibits areas of varied magnitude such that an increase in resistance to an opening force as applied to the packaging device occurs during removal of the packaging device and contained protective covering from the protected device.

D8. A system comprising:
a packaging device as in D3 with opposing sections that can be separated by the application of opposing forces to opposite sides of the opposing sections and where the width between the inside margins of the packing device is non-uniform;
an object enclosed within the packaging device which is of a non-uniform width or cross-sectional area;
so constructed such that as the opposing sections of said packaging device are separated by an opening force that an increase in resistance of packaging removal is created by the compression of a wider section of said enclosed object and a narrower inside within of the packaging system.

A system as in D4, D5, D6, D7 and/or D8 wherein a change in the resistance of removal of the protective packaging device assists in configuring the system such that the amount of the removable covering that is removed is limited at the point of increased resistance.

A system as in D4, D5, D6, D7 and/or D8 wherein a change in the resistance of removal of the protective packaging device assists in stabilizing, activating, preparing and orienting the contained object for application, deployment, activation or utilization.

A system as in D4, D5, D6, D7 and/or D8 wherein a change in the resistance during removal of the protective packaging device allows transmission of a distracting or distorting force to the contained object.

A system as in D4, D5, D6, D7 and/or D8 wherein after partial removal of the packaging device that an increase in applied opening force overcomes the increase in resistance to an opening force and removes the remainder of the packaging device from the protected device.

A system as in D4, D5, D6, D7 and/or D8 wherein after partial removal of the packaging device that an increase in applied opening force overcomes the increase in resistance to an opening force and removes the remainder of the packaging device and the removable covering from the protected device.

A system as in D4, D5, D6, D7 and/or D8 wherein after partial removal of the packaging device and attached removable covering that the remainder of the packaging device and removable covering are removed from the protected device by the application of an opening force to a secondary point on the packaging device or removable covering.

A system as in D7 and/or D8 wherein after partial removal of the packaging device up to the point of increased opening resistance that the remainder of the packaging device can be removed from the protected device by the application of an opening force to a secondary point on the packaging device.

A system as in D4, D5, D6, D7 and/or D8 wherein a design element such as a figure, character, logo, words or other features are visible on the surface of the packaging device such that the application of opening forces separates said design elements on the segments of the packaging system creating a change in appearance of the system.

A system as in D4, D5, D6, D7 and/or D8 wherein a design element such as a figure, character, logo, words or other features are visible on the surface of the packaging device and where a design element such as a figure, character, logo, words or other features are present on the surface of the contained protected device;

where said design element present on the surface of the contained protected device is not visible while said protected device remains within an unopened packaging device; and where the application of opening forces separates said design elements on the segments of the packaging device and simultaneously exposes the design element on said protected device.

The invention claimed is:

1. A substantially planar removable covering for an object having a receiving surface, wherein the removable covering comprises:
   a central tab;
   a central section that is adhered to the receiving surface of the object;
   a first adhered section that is adhered to the receiving surface of the object;
   a tab section that is not adhered to the receiving surface of the object;
   a first free section that is not adhered to the receiving surface of the object; and
   a second free section that is not adhered to the receiving surface of the object;
   wherein said first free section and said second free section are connected to (i) opposite ends of said first adhered section and (ii) the same end of said tab section such that the first free section, second free section, and the first adhered section form a loop connected to said tab section; and
   wherein said tab section and said central tab are connected to opposite ends of said central section; and
   wherein the removable covering is sufficiently flexible to allow at least partial removal of said first adhered section from the object by application of a force to the removable covering.

2. The removable covering according to claim 1, wherein the force required to remove the removable covering from the object varies at different zones of attachment between the removable covering and the object.

3. The removable covering according to claim 2, wherein the force required to remove the removable covering from the object is greatest at the second a second to last zone of attachment.

4. The removable covering according to claim 1, wherein the removable covering is adhered to the object such that resistance to removal of the removable covering from the object varies at different zones of attachment between the removable covering and the object.

5. The removable covering according to claim 4, wherein the removable covering is adhered to the object such that resistance to removal of the removable covering from the object is greatest at a second to last zone of attachment.

6. The removable covering according to claim 1, wherein:
   a left side of the removable covering covers one half of the object's receiving surface;
   a right side of the removable covering covers the other half of the object's receiving surface; and
   the removable covering's left side comprises the same components as the removable covering's right side.

7. The removable covering according to claim 1, wherein said first adhered section has a surface of varying textures that faces the object such that the removable covering's resistance to removal from the object varies.

8. The removable covering according to claim 1, wherein said first adhered section has a surface comprising a varied release coating that faces the object such that the removable covering's resistance to removal from the object varies.

9. The removable covering according to claim 1, wherein the removable covering is less elastic than the object.

10. The removable covering according to claim 1, wherein the thickness of the removable covering varies along the surface of the object such that the removable covering's resistance to removal from the object varies.

11. A system, comprising:
    an object; and
    a removable covering comprising:
       a first adhered section that is adhered to the object;
       a first interlocking extension section integrated with the first adhered section;
       a second adhered section that is adhered to the object; and
       a second interlocking extension section integrated with the second adhered section;
    wherein the first interlocking extension section and the second interlocking extension section comprise features for interlocking the first interlocking extension section and the second interlocking extension section before application of the object to a surface, wherein the system is configured so that interlocking the first interlocking extension section and the second interlocking extension section results in tensioning of the object.

12. The system of claim 11, wherein the object comprises:
    a first end section;
    a first adhesive layer adhering the first adhered section to the first end section;
    a second end section;
    a second adhesive layer adhering the second adhered section to the second end section; and
    a central bridge.

13. The system of claim 12, wherein the system is configured so that, after application of the object to a surface and release of the interlocking of the first interlocking extension section and the second interlocking extension section, the central bridge provides tension across the surface.

14. The system of claim 11, wherein the system is configured so that, when the first interlocking extension section and the second interlocking extension section are interlocked, the first adhered section and the second adhered section expose a larger section of a central zone of the object than is exposed before interlocking.

15. The system of claim 14, wherein the system is configured so that interlocking the first interlocking extension and the second interlocking extension before application of the object to a surface results in shear stress in the first and second adhesive layers.

16. The system of claim 11, wherein the features comprise complimentary interlocking notches.

17. The system of claim 11, wherein the removable covering comprises:
    an end of the first adhered section nearest the center of the object that is not adhered to the object; and
    an end of the second adhered section nearest the center of the object that is not adhered to the object.

18. The system of claim 11, wherein:
    the first adhered section comprises a first tab on its end nearest the center of the object; and the second adhered section comprises a second tab on its end nearest the center of the object that is not adhered to the object.

19. The system of claim 11, wherein the system is configured so that, when the first interlocking extension section and the second interlocking extension section are interlocked, the first adhered section and the second adhered section pull away from a central zone of the object.

20. The system of claim 11, wherein:
the object comprises:
a first end section,
a first adhesive layer adhering the first end section to the first adhered section of the removable covering,
a second end section, and
a second adhesive layer adhering the second end section to the second adhered section of the removable covering; and
the system is configured so that interlocking the first interlocking extension and the second interlocking extension before application of the object to a surface results in:
tensioning of the first and second extensions of the removable covering, and
shear stress in at least a portion of the system.

21. A substantially planar removable covering for an object, comprising:
a first adhered section that is adhered to the object;
a tab section that is not adhered to the object;
a first free section that is not adhered to the object; and
a second free section that is not adhered to the object;
wherein said first free section and said second free section are connected to (i) opposite ends of said first adhered section and (ii) the same end of said tab section so that said first and second free sections and said first adhered section form a loop that
is connected to said tab section, and
does not circumscribe the object; and
wherein the removable covering is sufficiently flexible to allow at least partial removal of said first adhered section from the object by application of a force to the removable covering.

22. The removable covering according to claim 1, wherein the force required to remove the removable covering from the object by way of said tab section varies at different zones of attachment between the removable covering and the object.

23. The removable covering according to claim 2, wherein the force required to remove the removable covering from the object is greatest at the second a second to last zone of attachment.

24. The removable covering according to claim 1, wherein the removable covering is adhered to the object such that resistance to removal of the removable covering from the object by way of said tab section varies at different zones of attachment between the removable covering and the object.

25. The removable covering according to claim 4, wherein the removable covering is adhered to the object such that resistance to removal of the removable covering from the object is greatest at a second to last zone of attachment.

26. The removable covering according to claim 1, wherein:
the object comprises a receiving surface; and
the removable covering comprises (i) a left side that covers one half of the object's receiving surface and (ii) a right side that covers the other half of the object's receiving surface;
wherein the removable covering's left side comprises the same components as the removable covering's right side.

27. The removable covering according to claim 21, wherein the removable covering is less elastic than the object.

28. A system, comprising:
an object comprising:
a central section positioned between and connected to first and second end sections of the object,
adhesive on the first end section for adhering the first end section to a surface, and
adhesive on the second end section for adhering the second end section to the surface; and
a removable covering comprising:
a first adhered section adhesively bonded to the first end section of the object by the adhesive on the first end section,
a second adhered section adhesively bonded to the second end section of the object by the adhesive on the second end section,
a first extension section extending from the first adhered section, and
a second extension section extending from the second adhered section;
wherein at least one feature of the system is configured for connecting the first extension section and the second extension section to one another before application of the object to a surface, and wherein the system is configured so that connecting the first extension section and the second extension section to one another with the at least one feature results in tensioning of the object.

29. The system of claim 15, wherein the central section of the object comprises an arcuate central bridge.

30. The system of claim 15, wherein the system is configured so that connecting the first extension section and the second extension section to one another with the at least one feature results in outwardly-convex bending of the object.

31. The system of claim 15, wherein the system is configured so that connecting the first extension section and the second extension section to one another with the at least one feature results in:
the adhesive bond between the first end section and the first adhered section being in shear stress, and
the adhesive bond between the second end section and the second adhered section being in shear stress.

32. A substantially planar removable covering for an object, comprising:
a first adhered section that is adhered to the object
a tab section that is not adhered to the object
a first free section that is not adhered to the object and
a second free section that is not adhered to the object
wherein said first free section and said second free section are connected to (i) opposite ends of said first adhered section and (ii) the same end of said tab section;
wherein the removable covering is sufficiently flexible to allow at least partial removal of said first adhered section from the object by application of a force to the removable covering; and wherein said first adhered section has a surface of varying textures that faces the object such that the removable covering's resistance to removal from the object varies.

33. A substantially planar removable covering for an object, comprising:
a first adhered section that is adhered to the object
a tab section that is not adhered to the object
a first free section that is not adhered to the object and
a second free section that is not adhered to the object
wherein said first free section and said second free section are connected to (i) opposite ends of said first adhered section and (ii) the same end of said tab section;
wherein the removable covering is sufficiently flexible to allow at least partial removal of said first adhered section from the object by application of a force to the removable covering; and
wherein said first adhered section has a surface comprising a varied release coating that faces the object such that the removable covering's resistance to removal from the object varies.

34. A substantially planar removable covering for an object, comprising:
a first adhered section that is adhered to the object
a tab section that is not adhered to the object
a first free section that is not adhered to the object and
a second free section that is not adhered to the object
wherein said first free section and said second free section are connected to (i) opposite ends of said first adhered section and (ii) the same end of said tab section;
wherein the removable covering is sufficiently flexible to allow at least partial removal of said first adhered section from the object by application of a force to the removable covering; and
wherein the thickness of the removable covering varies along a surface of the object such that the removable covering's resistance to removal from the object varies.

* * * * *

UNITED STATES PATENT AND TRADEMARK OFFICE
CERTIFICATE OF CORRECTION

PATENT NO. : 11,229,555 B2
APPLICATION NO. : 16/153340
DATED : January 25, 2022
INVENTOR(S) : Felmont F. Eaves et al.

It is certified that error appears in the above-identified patent and that said Letters Patent is hereby corrected as shown below:

In the Claims

Column 43, Claim 3 delete Line 48 and insert: -- the object is greatest at a second to last zone of --

Column 45, Claim 22 delete Line 44 and insert: -- The removable covering according to claim 21, --

Column 45, Claim 23 delete Line 49 and insert: -- The removable covering according to claim 22, --

Column 45, Claim 23 delete Line 52 and insert: -- ing from the object is greatest at a second to last --

Column 45, Claim 24 delete Line 54 and insert: -- The removable covering according to claim 21, --

Column 45, Claim 25 delete Line 60 and insert: -- The removable covering according to claim 24, --

Column 46, Claim 29 delete Line 40 and insert: -- The system of claim 28, wherein the central section of --

Column 46, Claim 30 delete Line 42 and insert: -- The system of claim 28, wherein the system is --

Column 46, Claim 31 delete Line 47 and insert: -- The system of claim 28, wherein the system is --

Column 47, Claim 33 delete Lines 6-9 and insert: -- a first adhered section that is adhered to the object; a tab section that is not adhered to the object; a first free section that is not adhered to the object; and a second free section that is not adhered to the object; --

Column 48, Claim 34 delete Lines 4-7 and insert: -- a first adhered section that is adhered to the object; a tab section that is not adhered to the object; a first free section that is not adhered to the object; and a second free section that is not adhered to the object; --

Signed and Sealed this
Fourth Day of March, 2025

Coke Morgan Stewart
*Acting Director of the United States Patent and Trademark Office*